United States Patent
Zhang et al.

(10) Patent No.: US 9,974,762 B2
(45) Date of Patent: May 22, 2018

(54) NECROSIS INHIBITORS

(71) Applicant: National Institute of Biological Sciences, Beijing, Beijing (CN)

(72) Inventors: Zhiyuan Zhang, Beijing (CN); Xiaodong Wang, Beijing (CN); Xiaoguang Lei, Beijing (CN); Yaning Su, Beijing (CN); Sudan He, Beijing (CN); Hanying Ruan, Beijing (CN); Liming Sun, Beijing (CN)

(73) Assignee: National Institute of Biological Sciences, Beijing, Beijing (CN)

( * ) Notice: Subject to any disclaimer, the term of this patent is extended or adjusted under 35 U.S.C. 154(b) by 0 days. days.

(21) Appl. No.: 15/632,412

(22) Filed: Jun. 26, 2017

(65) Prior Publication Data

US 2017/0290790 A1 Oct. 12, 2017

Related U.S. Application Data

(63) Continuation of application No. PCT/CN2015/098367, filed on Dec. 23, 2015, which is a continuation of application No. PCT/CN2014/094735, filed on Dec. 24, 2014.

(51) Int. Cl.
| | |
|---|---|
| *A61K 31/165* | (2006.01) |
| *A61K 31/10* | (2006.01) |
| *C07C 25/13* | (2006.01) |
| *C07C 25/02* | (2006.01) |
| *C07C 233/05* | (2006.01) |
| *C07C 233/01* | (2006.01) |

(52) U.S. Cl.
CPC ............ *A61K 31/165* (2013.01); *A61K 31/10* (2013.01); *C07C 25/02* (2013.01); *C07C 25/13* (2013.01); *C07C 233/01* (2013.01); *C07C 233/05* (2013.01)

(58) Field of Classification Search
USPC .......................................................... 514/613
See application file for complete search history.

(56) References Cited

U.S. PATENT DOCUMENTS

| | | | | |
|---|---|---|---|---|
| 4,977,188 A | * | 12/1990 | Kneen ...................... | A01N 3/00 514/507 |
| 9,643,977 B2 | * | 5/2017 | Yuan ..................... | C07D 495/04 |
| 9,725,452 B2 | * | 8/2017 | Yuan ..................... | C07D 487/04 |

OTHER PUBLICATIONS

ISR-WO PCT/CN2015/098367.

\* cited by examiner

*Primary Examiner* — Sun Jae Yoo
(74) *Attorney, Agent, or Firm* — Richard Aron Osman

(57) ABSTRACT

The invention provides amides that inhibit cellular necrosis and/or human receptor interacting protein 1 kinase (RIP1), including corresponding sulfonamides, and pharmaceutically acceptable salts, hydrides and stereoisomers thereof. The compounds are employed in pharmaceutical compositions, and methods of making and use, including treating a person in need thereof with an effective amount of the compound or composition, and detecting a resultant improvement in the person's health or condition.

20 Claims, No Drawings

NECROSIS INHIBITORS

INTRODUCTION

Tumor necrosis factor alpha (TNF-α)-induced NF-κB activation plays a central role in the immune system and inflammatory responses. Receptor-interacting protein 1 (RIP1) is a multi-functional signal transducer involved in mediating nuclear factor κB (NF-κB) activation, apoptosis, and necroptosis. The kinase activity of RIP1 is critically involved in mediating necroptosis, a caspase-independent pathway of necrotic cell death. Holler et al. Nat Immunol 2000; 1: 489-495; Degterev et al. Nat Chem Biol 2008; 4: 313-321.

Necroptosis plays a role in various pathological forms of cell death, including ischemic brain injury, neurodegenerative diseases and viral infections. Dunai, et al., December 2011, Pathol. Oncol. Res.: POR 17 (4): 791-800. Necrostatin-1 (Nec-1), a small molecule inhibitor of RIP1 kinase activity, can block necroptosis. Degterev et al. Nat Chem Biol 2005; 1: 112-119.

Related patent publications include: U.S. Pat. No. 6,756,394, U.S. Pat. No. 8,278,344, US2012122889, US2009099242, US2010317701, US2011144169, US20030083386, US20120309795, WO2009023272, WO2010075290, WO2010075561, WO2012125544

SUMMARY OF THE INVENTION

The invention provides an inhibitor of cellular necrosis and/or human receptor interacting protein 1 kinase (RIP1), that is an amide compound of formula:

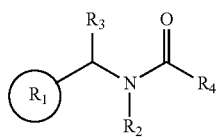

wherein:

R1 is a C3-C14 cyclic or hetero-cyclic moiety, particularly substituted or unsubstituted, 0-3 heteroatom C3-C9 cycloalkyl, cycloalkenyl, cycloalkynyl; or substituted or unsubstituted, 0-3 heteroatom C5-C14 aryl;

R2-R4 are independently: H, substituted or unsubstituted heteroatom, substituted or unsubstituted, 0-3 heteroatom C1-C9 alkyl, substituted or unsubstituted, 0-3 heteroatom C2-C9 alkenyl, substituted or unsubstituted, 0-3 heteroatom C2-C9 alkynyl, and substituted or unsubstituted, 0-3 heteroatom C5-C14 aryl, wherein each heteroatom is independently oxygen, phosphorus, sulfur or nitrogen; or a corresponding sulfonamide of the amide compound, or a pharmaceutically acceptable salt, hydride or stereoisomer the compound;

with the proviso that if R1 is phenyl, R3 is H, and R4 is 1,1-dimethylpropyl, then R2 is other than H, preferably substituted or unsubstituted heteroatom, substituted or unsubstituted, 0-3 heteroatom C1-C9 alkyl, substituted or unsubstituted, 0-3 heteroatom C2-C9 alkenyl, substituted or unsubstituted, 0-3 heteroatom C2-C9 alkynyl, and substituted or unsubstituted, 0-3 heteroatom C5-C14 aryl, wherein each heteroatom is independently oxygen, phosphorus, sulfur or nitrogen.

The invention also provides the corresponding sulfonamides of all the generally and specifically disclosed amides, e.g.

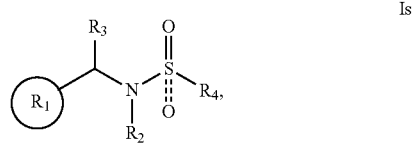

wherein S may be double bond to one or two O atoms, or a pharmaceutically acceptable salt, hydride or stereoisomer thereof, wherein the R moieties are as described herein, or a pharmaceutically acceptable salt, hydride or stereoisomer thereof.

The invention provides pharmaceutical compositions comprising the subject compounds, and methods of making and using the subject compounds, including methods of inhibiting cellular necrosis and/or human RIP1. The compositions may comprise a pharmaceutically-acceptable excipient, be in effective, unit dosage form, and/or comprise another, different therapeutic agents for the targeted disease or condition. In embodiments, the invention provides methods of treating a person in need thereof with an effective amount of the subject compound or pharmaceutical composition, and optionally, detecting a resultant improvement in the person's health or condition. The methods may also optionally include the antecedent step of determining that the person, particularly diagnosing and applicable disease or condition (herein).

The invention encompasses all combination of the particular embodiments recited herein.

DESCRIPTION OF PARTICULAR EMBODIMENTS OF THE INVENTION

The following descriptions of particular embodiments and examples are provided by way of illustration and not by way of limitation. Those skilled in the art will readily recognize a variety of noncritical parameters that could be changed or modified to yield essentially similar results. The invention provides myriad embodiments.

1. The invention provides amide inhibitors of cellular necrosis and/or human receptor interacting protein 1 kinase (RIP1).

2. In particular embodiments the subject compounds are of formula:

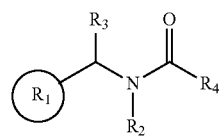

wherein:

R1 is a C3-C14 cyclic or hetero-cyclic moiety, preferably substituted or unsubstituted, 0-3 heteroatom C3-C9 cycloalkyl, cycloalkenyl, cycloalkynyl; or substituted or unsubstituted, 0-3 heteroatom C5-C14 aryl;

R2-R4 are independently: H, substituted or unsubstituted heteroatom, substituted or unsubstituted, 0-3 heteroatom C1-C9 alkyl, substituted or unsubstituted, 0-3 heteroatom C2-C9 alkenyl, substituted or unsubstituted, 0-3 heteroatom C2-C9 alkynyl, and substituted or unsubstituted, 0-3 heteroatom C5-C14 aryl, wherein each heteroatom is independently oxygen, phosphorus, sulfur or nitrogen; or a corresponding sulfonamide of the amide compound, or a pharmaceutically acceptable salt, hydride or stereoisomer the compound.

Excluded from the scope of the invention is an initial compound library screening hit of structure:

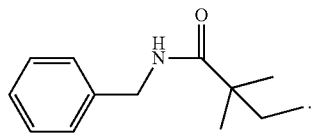

For example, compounds of formula I include the proviso that if R1 is phenyl, R3 is H, and R4 is 1,1-dimethylpropyl, then R2 is other than H, i.e. is substituted or unsubstituted heteroatom, substituted or unsubstituted, 0-3 heteroatom C1-C9 alkyl, substituted or unsubstituted, 0-3 heteroatom C2-C9 alkenyl, substituted or unsubstituted, 0-3 heteroatom C2-C9 alkynyl, and substituted or unsubstituted, 0-3 heteroatom C5-C14 aryl, wherein each heteroatom is independently oxygen, phosphorus, sulfur or nitrogen.

2. In particular aspects:

$R_1$ is (a) substituted or unsubstituted phenyl;

(b) substituted or unsubstituted 2-, 3- or 4-pyridine;

(c) substituted or unsubstituted naphthyl or 3-azanaphthyl;

(d) 0-3 heteroatom cyclohexyl, cyclopentyl, such as tetrahydrofuran; or (e) 0-3 heteroatom cyclopentene or cyclopentadiene, such as pyrrole, azole (e.g. pyrazole, imidazole, triazole, tetrazole, pentazole, oxazole, isoxazole, thiazole or isothiazole), furan, dioxole thiophene, dithiole or oxathiole, preferably 2-moieties, such as 2-azole, 2-pyrrole, 2-azole (e.g. 2-pyrazole, 2-imidazole, 2-oxazole, 2-isoxazole, 2-thiozole, or 2-isothiozole), 2-furan, 2-thiophene, 2-oxole, dioxole, or 2-thiole; and/or $R_2$ is H, hydroxyl, C1-C4 alkyl (e.g. methyl, ethyl, propyl), or C1-C4alkoyxl (e.g. methoxyl); and/or $R_3$ is H or methyl, and/or $R_4$ is 1-dimethylpropyl.

All possible combinations are encompassed as though each was expressly recited; hence, the aspects and embodiments include, for example, the combination wherein $R_1$ is substituted or unsubstituted phenyl; $R_2$ is H, hydroxyl, C1-C4 alkyl, or C1-C4alkoyxl, $R_3$ is H or methyl, and $R_4$ is 1-dimethylpropyl.

3. As another example of such a combination, in an aspect the compound is of formula:

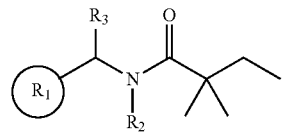

wherein:

$R_1$ is (a) substituted or unsubstituted phenyl, (b) substituted or unsubstituted 2-, 3- or 4-pyridine, or (c) substituted or unsubstituted naphthyl or 3-azanaphthyl;

(d) 0-3 heteroatom cyclohexyl, cyclopentyl, such as tetrahydrofuran;

(e) 0-3 heteroatom cyclopentene or cyclopentadiene, such as pyrrole, azole (particularly pyrazole, imidazole, triazole, tetrazole, pentazole, oxazole, isoxazole, thiazole or isothiazole), furan, dioxole thiophene, dithiole or oxathiole;

$R_2$ is H, hydroxyl, C1-C4 alkyl (e.g. methyl, ethyl, propyl), or C1-C4alkoyxl (e.g. methoxyl); and $R_3$ is H or methyl, or a corresponding sulfonamide of the amide compound, or a pharmaceutically acceptable salt, hydride or stereoisomer the compound.

4. In another aspect, the compound is of formula:

1a wherein:

$R_1$ is substituted or unsubstituted phenyl, and $R_2$ is H, OH or substituted or unsubstituted C1-C9 alkyl, a corresponding sulfonamide of the amide compound, or a pharmaceutically acceptable salt, hydride or stereoisomer the compound.

5. In embodiments R1 and R2 are as follows:

| # | R1 | $R_2$ | # | R1 | $R_2$ |
|---|---|---|---|---|---|
| 1 | 2-F-phenyl | H | 33 | 2-F, 3-OCF$_3$-phenyl | Me |
| 3 | 2-Br-phenyl | H | 48 | 2-F, 4-F, 6-F-phenyl | Me |
| 4 | 2-CF3-phenyl | H | 49 | 2-F, 3-F, 4-F-phenyl | Me |
| 5 | 3-F-phenyl | H | 50 | 2-F, 3-Me, 6-F-phenyl | Me |
| 6 | 3-Br-phenyl | H | 51 | 2-F, 3-F, 5-F, 6-F-phenyl | Me |
| 7 | 2-F, 4-F-phenyl | H | 56 | 2-Br, 5-F-phenyl | Me |
| 8 | 3-F, 4-F-phenyl | H | 57 | 2-CN, 5-F-phenyl | Me |
| 10 | 2-F-phenyl | Et | 63 | 3-F-phenyl | 3-OMe-propyl |
| 11 | 2-F-phenyl | 1-propyne | 64 | 3-F-phenyl | CH2-cyclopropyl |
| 12 | 2-F-phenyl | 3-oxobutyl | 70 | 2-F, 3-F, 5-F-phenyl | H |
| 13 | 2-F-phenyl | Me | 75 | 2-F, 3-F, 5-F-phenyl | Me |
| 14 | 2-Cl-phenyl | Me | 77 | 2-F, 3-F, 5-F-phenyl | EtOH |
| 15 | 2-OMe-phenyl | Me | 90 | phenyl | Me |
| 16 | 3-F-phenyl | Me | 91 | 3-F,4-F-phenyl | Me |
| 17 | 3-CN-phenyl | Me | 92 | phenyl | OH |

-continued

| # | R1 | R₂ | # | R1 | R₂ |
|---|---|---|---|---|---|
| 18 | 3-Cl-phenyl | Me | 93 | 2-F, 3-F, 5-F-phenyl | OH |
| 19 | 3-Br-phenyl | Me | 94 | 4-F-phenyl | OH |
| 20 | 3-OMe-phenyl | Me | 95 | 3-F, 4-F-phenyl | OH |
| 21 | 3-OH-phenyl | Me | 96 | 2-F, 4-F-phenyl | OH |
| 22 | 4-OEtOH-phenyl | Me | 97 | 2-F, 3-F, 4-F-phenyl | OH |
| 23 | 3-COOMe-phenyl | Me | 98 | 2-F, 4-F, 5-F-phenyl | OH |
| 24 | 2-F, 4-F-phenyl | Me | 99 | 3-F, 4-F, 5-F-phenyl | OH |
| 25 | 2-F, 5-F-phenyl | Me | 130 | 4-F-phenyl | OMe |
| 26 | 3-F, 5-F-phenyl | Me | 131 | 2-F, 4-F-phenyl | OMe |
| 27 | 2-F, 4-Cl-phenyl | Me | 132 | 3-F, 4-F-phenyl | OMe |
| 28 | 2-F, 4-OMe-phenyl | Me | 133 | 2-F, 4-F, 5-F-phenyl | OMe |
| 29 | 2-F, 4-F-phenyl | Et | 134 | 3-F, 4-F, 5-F-phenyl | OMe |
| 30 | 3-NO₂, 4-N-pipiridine-phenyl | Me | 135 | 2-F, 3-F, 5-F-phenyl | OMe |
| 31 | 3-Me, 3-Me-phenyl | Me | 151 | phenyl | OMe |
| 32 | 3-Me, 5-Me-phenyl | Me | | | |
| S3 | phenyl | OAcetyl | S4 | phenyl | OMe |
| S7 | 3-F-phenyl | Me | S8 | 2F, 3F-phenyl | Me. |

6. In another aspect the compound is of formula:

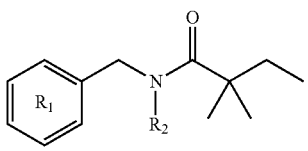

1b wherein

R₁ is substituted or unsubstituted 2-, 3- or 4-pyridine, and

R₂ is H, Me, or a corresponding sulfonamide of the amide compound, or a pharmaceutically acceptable salt, hydride or stereoisomer the compound.

7. In embodiments the R1 is as follows:

| # | R1 | R2 |
|---|---|---|
| 9 | 3-pyridine | H |
| 34 | 4-pyridine | Me |
| 35 | 3-pyridine | Me |
| 36 | 2-F-4-pyridine | Me |
| 37 | 2-OMe-3-pyridine | Me |
| 38 | 4-OMe-3-pyridine. | Me |

8. In another aspect the compound is of formula:

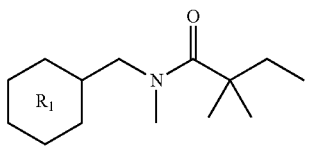

1c wherein

R₁ is substituted or unsubstituted cyclohexyl, or a corresponding sulfonamide of the amide compound, or a pharmaceutically acceptable salt, hydride or stereoisomer the compound.

9. In embodiments R1 is as follows:

| # | R1 | R2 |
|---|---|---|
| 39 | cyclohexyl. | methyl |
| 139 | cyclopentyl | hydroxyl |
| 140 | cyclopentenyl | hydroxyl |
| 141 | cyclohexyl | hydroxyl |
| 142 | tetrahydrofuran | hydroxyl. |

10. In another aspect the compound is of formula:

1d wherein

R₁ is substituted or unsubstituted 2-azole, 2-pyrrole, 2-furan, 2-thiophene, 2-oxole, dioxole, or 2-thiole, preferably wherein the 2-azole is: 2-pyrazole, 2-imidazole, triazole, tetrazole, pentazole, 2-oxazole, 2-isoxazole, 2-thiozole, or 2-isothiozole;

R₂ is Me, OH or OMe, and

R₃ is H or Me, or a corresponding sulfonamide of the amide compound, or a pharmaceutically acceptable salt, hydride or stereoisomer the compound.

11. In embodiments R1, R2 and S/D bond are as follows:

| # | R1 | R2 | Bond |
|---|---|---|---|
| 40 | 2-thiophene | Me | single |
| 41 | 5-Me, 2-thiophene | Me | single |
| 42 | 3-Me, 2-thiophene | Me | single |
| 43 | 2-furan | Me | single |
| 44 | 3-Me, 2-thiozole | Me | single |
| 45 | 3-Me, 2-pyrazole | Me | single |
| 128 | 3 Me, 4-Me, 2 thiophene | Me | single |
| 136 | 2-thiophene | OH | single |
| 137 | 3-Me, 2-thiophene | OH | single |
| 138 | 3 Me, 5-Me, 2 thiophene | OH | single |
| 143 | 2-N-Me, 2-pyrrole | OH | single |
| 144 | 3-N-Me, 3-Me, 2-pyrrole | OH | single |

-continued

| # | R1 | R2 | Bond |
|---|---|---|---|
| 145 | 5-Me, 2-thiophene | OH | double |
| 146 | 3-Me, 5-Me, 2-thiophene | OH | double |

12. In another aspect the compound is of formula:

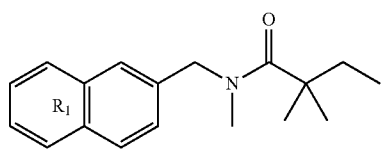

1e wherein
$R_1$ is substituted or unsubstituted naphthyl or 3-azanaphthyl, or
a corresponding sulfonamide of the amide compound, or
a pharmaceutically acceptable salt, hydride or stereoisomer the compound.

13. In embodiments R1 is as follows:

| # | R1 |
|---|---|
| 46 | naphthyl |
| 47 | 3-azanaphthyl. |

14. In another aspect the compound is of formula:

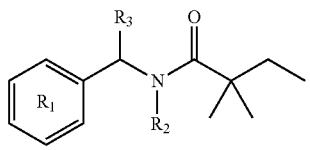

1f wherein
$R_1$ is substituted or unsubstituted phenyl; preferably unsubstituted phenyl,
$R_2$ is H, Me, OH, MeOH, or OMe; and
$R_3$ is H, Me, OH, MeOH, OMe or substituted or unsubstituted C1-C6 alkyl, preferably unsubstituted, or
a corresponding sulfonamide of the amide compound, or
a pharmaceutically acceptable salt, hydride or stereoisomer the compound.

15. In embodiments R1, R2 and R3 are as follows:

| # | R1 | R2 | R3 |
|---|---|---|---|
| 52 | phenyl | H | Me |
| 53 | phenyl | Me | Me |
| 54 | phenyl | H | cyclopropyl |
| 55 | phenyl | Me | cyclopropyl |
| 148 | 2F-phenyl | Me | MeOH |
| 149 | 2F, 3F, 5F phenyl | Me | MeOH |
| 150 | Phenyl | OH | MeOH. |

16. In another aspect the compound is of formula:

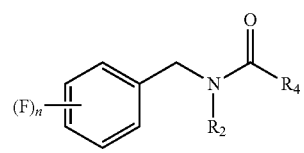

1g wherein
$R_2$ is H, OH or substituted or unsubstituted C1-C6 alkyl, and
$R_4$ is substituted or unsubstituted, 0-3 heteroatom C1-C6 alkyl, substituted or unsubstituted, 0-3 heteroatom C2-C6 alkenyl, substituted or unsubstituted, 0-3 heteroatom C2-C6 alkynyl, and substituted or unsubstituted, 0-3 heteroatom C6-C14 aryl, wherein each heteroatom is independently oxygen, phosphorus, sulfur or nitrogen,
n is 0, 1, 2, 3, 4 or 5, or
a corresponding sulfonamide of the amide compound, or
a pharmaceutically acceptable salt, hydride or stereoisomer the compound.
In embodiments, R4 is 1-dimethylpropyl, or a fluorinated form, such as 1-dimethyl, 2-difluoropropyl.

17. In embodiments (F)n, R2 and R4 are as follows:

| # | (F)n | R2 | R4 |
|---|---|---|---|
| 2 | — | H | C(Me)3 |
| 48 | 2F, 4F, 6F | Me | 1-dimethylpropyl |
| 49 | 2F, 3F, 4F | Me | 1-dimethylpropyl |
| 51 | 2F, 3F, 5F, 6F | Me | 1-dimethylpropyl |
| 59 | 2F | Me | 2-dimethylpropyl |
| 60 | 2F | Me | cyclohexyl |
| 61 | 2F | Me | phenyl |
| 62 | 2F | Me | cyclopropyl |
| 63 | 3F | CH2CH2CH2OMe | 1-dimethylpropyl |
| 64 | 3F | CH2-cyclopropyl | 1-dimethylpropyl |
| 65 | 2F, 3F, 5F | Me | 1-methyl cyclohexyl |
| 66 | 3F, 4F, 5F | Me | C(Me)2MeOH |
| 67 | 2F, 3F, 5F | Me | C(Me)2OMe |
| 68 | 3F, 4F, 5F | Me | C(Me)2CH2NHMe |
| 69 | 3F, 4F, 5F | Me | t-butyl |
| 70 | 2F, 3F, 5F | H | 1-dimethylpropyl |
| 71 | 3F, 4F, 5F | Me | C(CH3)2CH2OMe |
| 72 | 3F, 4F, 5F | Me | C(Me)(Et)2 |
| 73 | 3F, 4F, 5F | H | C(Me)(Et)2 |
| 74 | 2F, 3F, 5F | Et | cyclohexyl |
| 75 | 2F, 3F, 5F | Me | 1-dimethylpropyl |
| 76 | 2F, 3F, 5F | Me | CO-adamanthanyl |
| 77 | 2F, 3F, 5F | EtOH | 1-dimethylpropyl |

-continued

| # | (F)n | R2 | R4 |
|---|---|---|---|
| 78-S | 2F, 3F, 5F | Me | t-butyl |
| 79-S | 2F, 3F, 5F | Me | cyclohexyl |
| 80 | 2F, 3F, 5F | Me | 1-methyl cyclopropyl |
| 81 | 3F, 4F, 5F | Me | 2,3-(dimethyl)cyclopropyl |
| 82 | 2F, 3F, 5F | Me | 1-phenyl cyclopropyl |
| 83 | 2F, 3F, 5F | Me | cyclobutyl |
| 84 | 2F, 3F, 5F | Me | 1-CF3 cyclobutyl |
| 85 | 2F, 4F, 5F | Me | cyclopentyl |
| 86 | 2F, 3F, 5F | Me | 1-CF3 cyclopentyl |
| 87 | 2F, 3F, 5F | Me | 1-phenyl cyclopentyl |
| 88 | 3F, 4F, 5F | Me | 1-ethyl cyclobutyl |
| 89 | 3F, 4F, 5F | Me | 1-ethyl cyclopentyl |
| 92 | — | OH | 1-dimethylpropyl |
| 93 | 2F, 3F, 5F | OH | 1-dimethylpropyl |
| 94 | 4F | OH | 1-dimethylpropyl |
| 95 | 2F, 4F | OH | 1-dimethylpropyl |
| 96 | 2F, 4F | OH | 1-dimethylpropyl |
| 97 | 2F, 3F, 4F | OH | 1-dimethylpropyl |
| 98 | 2F, 4F, 5F | OH | 1-dimethylpropyl |
| 99 | 3F, 4F, 5F | OH | 1-dimethylpropyl |
| 126 | — | CH2CH2CH2OMe | 1-dimethylpropyl |
| 129 | 3F, 4F, 5F | Me | 2-Cl, 6-Cl phenyl. |
| 130 | 4-F | OMe | 1-dimethylpropyl |
| 131 | 2-F, 4-F | OMe | 1-dimethylpropyl |
| 132 | 4-F, 5-F | OMe | 1-dimethylpropyl |
| 133 | 2-F, 4-F, 5-F | OMe | 1-dimethylpropyl |
| 134 | 3-F, 4-F, 5-F | OMe | 1-dimethylpropyl |
| 135 | 2-F, 3-F, 5-F-223 | OMe | 1-dimethylpropyl |
| 147 | 2-F | Me | 1-dimethylprop-2-enyl |
| 151 | — | OMe | 1-dimethylpropyl |
| S1 | 2-F, 3-F, 5-F | H | t-butyl |
| S2 | 2-F, 3-F, 5-F | Me | t-butyl |
| S5 | 2-F, 3-F, 5-F | Me | 1-dimethyl, 2-difluoropropyl |
| S6 | — | OH | 1-dimethyl, 2-difluoropropyl |
| S9 | 4-F | OH | 1-dimethyl, 2-difluoropropyl |
| S10 | 2-F, 4-F | OH | 1-dimethyl, 2-difluoropropyl |
| S11 | 3-F, 4-F | OH | 1-dimethyl, 2-difluoropropyl |
| S12 | 2-F, 4-F, 5-F | OH | 1-dimethyl, 2-difluoropropyl |
| S13 | 3-F, 4-F, 5-F | OH | 1-dimethyl, 2-difluoropropyl |
| S14 | 2-F, 3-F, 5-F | OH | 1-dimethyl, 2-difluoropropyl |
| S15 | 4-F | OMe | 1-dimethyl, 2-difluoropropyl |
| S16 | 2-F, 4-F | OMe | 1-dimethyl, 2-difluoropropyl |
| S17 | 3-F, 4-F | OMe | 1-dimethyl, 2-difluoropropyl |
| S18 | 2-F, 4-F, 5-F | OMe | 1-dimethyl, 2-difluoropropyl |
| S19 | 3-F, 4-F, 5-F | OMe | 1-dimethyl, 2-difluoropropyl |
| S20 | 2-F, 3-F, 5-F | OMe | 1-dimethyl, 2-difluoropropyl. |

18. In another aspect the compound is of formula:

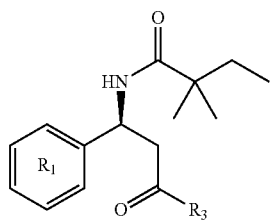

1h wherein $R_1$ is substituted or unsubstituted phenyl; and $R_3$ is substituted or unsubstituted heteroatom and substituted or unsubstituted, 0-3 heteroatom C1-C6 alkyl, wherein each heteroatom is independently oxygen, phosphorus, sulfur or nitrogen, or a corresponding sulfonamide of the amide compound, or a pharmaceutically acceptable salt, hydride or stereoisomer the compound.

19. In embodiments R1 and R3 are as follows:

| # | $R_1$ | $R_3$ |
|---|---|---|
| 100 | phenyl | OCH3 |
| 101 | phenyl | NHCH3 |
| 102 | phenyl | NHCH2CH2OCH2CH2OCH3 |
| 103 | phenyl | NHCH2CH3 |
| 104 | phenyl | NH-cyclohexyl |
| 105 | phenyl | N-piperidinyl |
| 106 | phenyl | NH-phenyl |
| 107 | phenyl | NH-benzyl |
| 108 | phenyl | NHCH2-benzyl. |
| 126 | phenyl | NHCH2CH2-phenoxy |

20. In another aspect the compound is of formula:

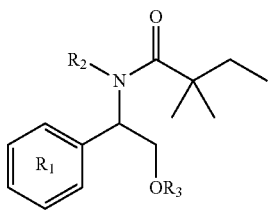

1i wherein
R₁ is substituted or unsubstituted phenyl;
R₂ is H or methyl; and
R₃ is H or methyl, or
a corresponding sulfonamide of the amide compound, or
a pharmaceutically acceptable salt, hydride or stereoisomer the compound.

21. In embodiments R1, R2 and R3 are as follows:

| # | R1 | R2 | R3 |
|---|---|---|---|
| 109 | phenyl | H | H |
| 110 | phenyl | H | H |
| 111 | phenyl | Me | H |
| 112 | phenyl | Me | Me |

22. In another aspect the compound is of formula:

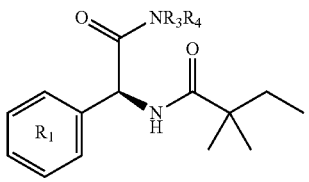

1j wherein
R₁ is substituted or unsubstituted phenyl;
R₃ is H or methyl; and
R₄ is substituted or unsubstituted C1-C6 alkyl, or
a corresponding sulfonamide of the amide compound, or
a pharmaceutically acceptable salt, hydride or stereoisomer the compound.

23. In embodiments R1, R2 and R3 are as follows:

| # | R1 | R3 | R4 |
|---|---|---|---|
| 122 | phenyl | H | Me |
| 123 | phenyl | Me | Me |
| 124 | phenyl | H | benzyl |
| 125 | phenyl | H | phenylethyl |
| 127 | phenyl | H | phenoxyethyl |

24. In another aspect the compound is of formula:

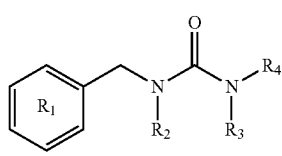

1k wherein
R₁ is substituted or unsubstituted phenyl;
R₂ is H, methyl or ethyl; and
R₃ and R₄ are independently H, lower alkyl and may be joined to form a substituted or unsubstituted C3-C8 cycloalkyl, or
a corresponding sulfonamide of the amide compound, or
a pharmaceutically acceptable salt, hydride or stereoisomer the compound.

25. In embodiments R1, R2, R3 and R4 are as follows:

| # | R₁ | R2 | R3 | R4 |
|---|---|---|---|---|
| 113 | 2F-phenyl | Me | H | cyclohexyl |
| 114 | 2F-phenyl | Me | H | isopropyl |
| 115 | 2F, 3F, 5F-phenyl | Et | Me | isopropyl |
| 116 | 2F, 3F, 5F-phenyl | Me | | 2-ethyl cyclohexyl |
| 117 | 2F, 3F, 5F-phenyl | Me | | 2-methyl cyclohexyl |
| 118 | 2F, 3F, 5F-phenyl | Me | | 3-methyl cyclohexyl |
| 119 | 2F, 3F, 5F-phenyl | Et | ispropyl | isopropyl |
| 120 | 2F, 3F, 5F-phenyl | Me | Isopropyl | methyl |
| 121 | 2F, 3F, 5F-phenyl | Me | | 2-methyl, 5-methyl cyclohexyl. |

26. In embodiments the subject compounds have a formula of Table 1.

27. In embodiments the invention provides pharmaceutical compositions comprising a subject compound and a pharmaceutically-acceptable excipient, in unit dosage.

28. In embodiments the invention provides pharmaceutical compositions comprising a subject compound and a pharmaceutically-acceptable excipient, in unit dosage, and a different therapeutic agent for a necrosis-associated disease or condition.

29. In embodiments the invention provides methods of treating a necrosis-associated disease or condition, comprising administering an effective amount of a subject compound or composition to a patient in need thereof.

30. In embodiments the invention the method of treatment comprise the antecedent step of diagnosing the necrosis-associated disease or condition, or the subsequent step of detecting a resultant amelioration of the necrosis-associated disease or condition.

Applicable diseases or conditions are necrosis- (including necroptosis) associated and include neuro-degenerative disease of the central or peripheral nervous system, endotoxic/septic shock, terminal ileitis, myocarditis, arthritis, atherosclerosis, acute enteritis, ischemic necrosis, pathology resulting from renal failure or cell death, including retinal neuronal, cardiac muscle or immune cell death, such as chemo- or radiation-induced necrosis; liver disease, including drug-induced liver damage or toxicity, acute hepatitis, etc., pancreatic disease, including necrotizing pancreatitis, heart, mesenteric, retinal, hepatic or brain/cerebral ischemic injury, nephritis, ischemic injury during reperfusion or organ storage, head trauma, including traumatic brain injury, stroke, septic shock, coronary heart disease, cardiomyopathy, myocardial infarction, bone avascular necrosis, sickle cell disease, muscle wasting, gastrointestinal disease, tuberculosis, diabetes, pathogenic alteration of blood vessels, muscular dystrophy, graft-versus-host disease, viral, bacterial and fungal infection, Crohn's disease, ulcerative colitis, asthma, etc.

Exemplary applicable viruses are human immunodeficiency virus (HIV), Epstein-Barr virus (EBV), cytomegalovirus (CMV)5 human herpesviruses (HHV), herpes simplex viruses (HSV), human T-Cell leukemia viruses (HTLV)5 Varicella-Zoster virus (VZV), measles virus, papovaviruses (JC and BK), hepatitis viruses, adenovirus, parvoviruses, and human papillomaviruses. Exemplary diseases caused by viral infection include, but are not limited to, chicken pox, Cytomegalovirus infections, genital herpes, Hepatitis B and C, influenza, and shingles.

Exemplary applicable bacteria include, but are not limited to *Campylobacter jejuni, Enterobacter species, Enterococcus faecium, Enterococcus faecalis, Escherichia coli* (e.g., *E. coli* O157:H7), Group A streptococci, *Haemophilus influenzae, Helicobacter pylori, listeria, Mycobacterium tuberculosis, Pseudomonas aeruginosa, S. pneumoniae, Salmonella, Shigella, Staphylococcus aureus*, and *Staphylococcus epidermidis*. Exemplary diseases caused by bacterial infection include, but are not limited to, anthrax, cholera, diphtheria, foodborne illnesses, leprosy, meningitis, peptic ulcer disease, pneumonia, sepsis, tetanus, tuberculosis, typhoid fever, and urinary tract infection.

Exemplary applicable neurodegenerative diseases are Alzheimer's disease, Huntington's disease, Parkinson's disease, amyotrophic lateral sclerosis, HIV-associated dementia, cerebral ischemia, amyotropic lateral sclerosis, multiple sclerosis, Lewy body disease, Menke's disease, Wilson's disease, Creutzfeldt-Jakob disease, and Fahr disease.

Exemplary applicable muscular dystrophies or related diseases are Becker's muscular dystrophy, Duchenne muscular dystrophy, myotonic dystrophy, limb-girdle muscular dystrophy, Landouzy-Dejerine muscular dystrophy, facioscapulohumeral muscular dystrophy (Steinert's disease), myotonia congenita, Thomsen's disease, and Pompe's disease. Muscle wasting can be associated with cancer, AIDS, congestive heart failure, and chronic obstructive pulmonary disease, as well as include necrotizing myopathy of intensive care.

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein. Furthermore, genuses are recited as shorthand for a recitation of all members of the genus; for example, the recitation of (C1-C3) alkyl is shorthand for a recitation of all C1-C3 alkyls: methyl, ethyl and propyl, including isomers thereof.

The term "heteroatom" as used herein generally means any atom other than carbon or hydrogen. Preferred heteroatoms include oxygen (O), phosphorus (P), sulfur (S), nitrogen (N), and halogens, and preferred heteroatom functional groups are haloformyl, hydroxyl, aldehyde, amine, azo, carboxyl, cyanyl, thocyanyl, carbonyl, halo, hydroperoxyl, imine, aldimine, isocyanide, iscyante, nitrate, nitrile, nitrite, nitro, nitroso, phosphate, phosphono, sulfide, sulfonyl, sulfo, and sulfhydryl.

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —CH$_2$—CH$_2$—CH$_2$—CH$_2$—. Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, P, Si and S, wherein the nitrogen, sulfur, and phosphorous atoms may optionally be oxidized and the nitrogen heteroatom may optionally be quaternized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent means a divalent radical derived from heteroalkyl, as exemplified by —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is mean to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl and 1,2,3,4-tetrahydronaphthalene.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", —SR, halogen, —SiR'R"R"', —OC(O)R', —C(O)R', —CO₂R', —CONR'R", —OC(O)NR'R", —NR"C(O)R', —NR'—C(O)NR"R"', —NR'—SO₂NR"', —NR"CO₂R', —NH—C(NH₂)=NH, —NR'C(NH₂)=NH, —NH—C(NH₂)=NR', —S(O)R', —SO₂NR'R", —NR"SO₂R, —CN and —NO₂, in a number ranging from zero to three, with those groups having zero, one or two substituents being particularly preferred. R', R" and R"' each independently refer to hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF₃ and —CH₂CF₃).

Preferred substituents for the alkyl and heteroalkyl radicals are selected from: —OR', =O, —NR'R", —SR', halogen, —SiR'R"R"', —OC(O)R', —C(O)R', —CONR'R", —OC(O)NR'R", —NR"C(O)R', —NR"CO₂R', —NR'—SO₂NR"R"', —S(O)R', —SO2R', —SO₂NR'R", —NR"SO₂R, —CN and —NO₂, where R' and R" are as defined above. Further preferred substituents are selected from: —OR', =O, —NR'R", halogen, —OC(O)R', —CONR'R", —OC(O)NR'R", —NR"C(O)R', —NR"CO₂R', —NR'—SO₂NR"R"', —SO₂NR'R", —NR"SO₂R, —CN and —NO₂.

Similarly, substituents for the aryl and heteroaryl groups are varied and selected from: halogen, —OR', —OC(O)R', —NR'R", —SR', —R', —CN, —NO₂, —CONR'R", —C(O)R', —OC(O)NR'R", —NR"C(O)R', —NR"CO2R', —NR'—C(O)NR"R"', —NR'—SO₂NR"R"', —NH—C(NH2)=NH, —NR'C(NH₂)=NH, —NH—C(NH₂)=NR', —S(O)R', —SO₂R, —SO₂NR'R", —NR"SO₂R, —N₃, —CH(Ph)₂, perfluoro(C1-C4)alko-xy and perfluoro(C1-C4)alkyl, in a number ranging from zero to the total number of open valences on the aromatic ring system; and where R, R" and R"' are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. When the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl". Typically, an aryl or heteroaryl group will have from zero to three substituents, with those groups having two or fewer substituents being preferred in the invention. In one embodiment of the invention, an aryl or heteroaryl group will be unsubstituted or monosubstituted. In another embodiment, an aryl or heteroaryl group will be unsubstituted.

Preferred substituents for aryl and heteroaryl groups are selected from: halogen, —OR', —OC(O)R', —NR'R", —SR', —R, —CN, —NO₂, —CO₂R', —CONR'R", —C(O)

R', —OC(O)NR'R", —NR"C(O)R', —S(O)R', —SO$_2$R', —SO$_2$NR'R", —NR"SO$_2$R, —N$_3$, —CH(Ph)$_2$, perfluoro (C1-C4)alkoxy and perfluoro(C1-C4)alkyl, where R' and R" are as defined above. Further preferred substituents are selected from: halogen, —OR', —OC(O)R', —NR'R", —R', —CN, —NO$_2$, —CO$_2$R', —CONR'R", —NR"C(O)R', —SO$_2$R', —SO$_2$NR'R", —NR"SO$_2$R, perfluoro(C1-C4)alkoxy and perfluoro(C1-C4)alkyl.

The substituent —CO$_2$H, as used herein, includes bio-isosteric replacements therefor; see, e.g., The Practice of Medicinal Chemistry; Wermuth, C. G., Ed.; Academic Press: New York, 1996; p. 203.

Two of the substituents on adjacent atoms of the aryl or heteroaryl ring may optionally be replaced with a substituent of the formula -T-C(O)—(CH$_2$)q-U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH2)r-B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)s-X—(CH$_2$)t-, where s and t are independently integers of from 0 to 3, and X is —O—, —NR'—, —S—, —S(O)—, —S(O)$_2$—, or —S(O)$_2$NR'—. The substituent R in —NR'— and —S(O)$_2$NR'— is selected from hydrogen or unsubstituted (C1-C6)alkyl.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, 0-3 heteroatom C1-C6 alkyl, substituted or unsubstituted, 0-3 heteroatom C2-C6 alkenyl, substituted or unsubstituted, 0-3 heteroatom C2-C6 alkynyl, or substituted or unsubstituted, 0-3 heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3).

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, diastereomers, geometric isomers and individual isomers are all intended to be encompassed within the scope of the invention.

The compounds of the invention may also contain unnatural proportions of atomic isotopes at one or more of the atoms that constitute such compounds. For example, the compounds may be radiolabeled with radioactive isotopes, such as for example tritium CH), iodine-125 ($^{125}$I) or carbon-14 ($^{14}$C). All isotopic variations of the compounds of the invention, whether radioactive or not, are intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat an applicable disease or condition (herein).

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science*, Mack Publishing Co, NJ (1991). In addition, the compounds may be advantageously used in conjunction with other therapeutic agents as described herein or otherwise known in the art, particularly other anti-necrosis agents. Hence the compositions may be administered separately, jointly, or combined in a single dosage unit.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent compounds, microgram (ug) amounts per kilogram of patient may be sufficient, for example, in the range of about 1, 10 or 100 ug/kg to about 0.01, 0.1, 1, 10, or 100 mg/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as compounds potency, severity of the disease being treated. For example, a dosage regimen of the compounds can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

TABLE 1

1. Compound List

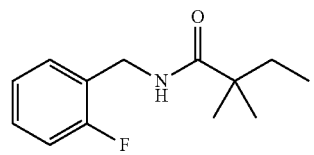 [SMILES: CCC(C)(C)C(=O)NCc1ccccc1F]

1

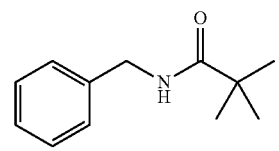

2

TABLE 1-continued
1. Compound List
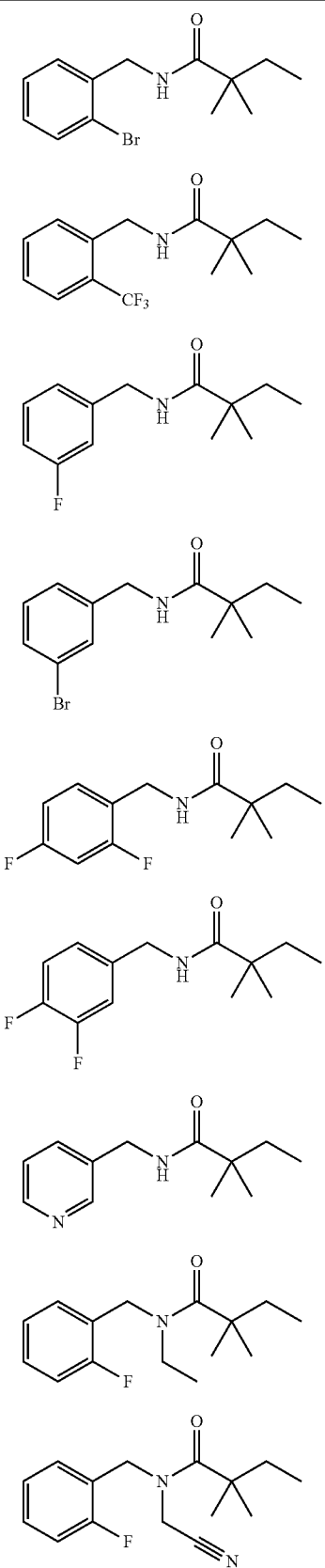
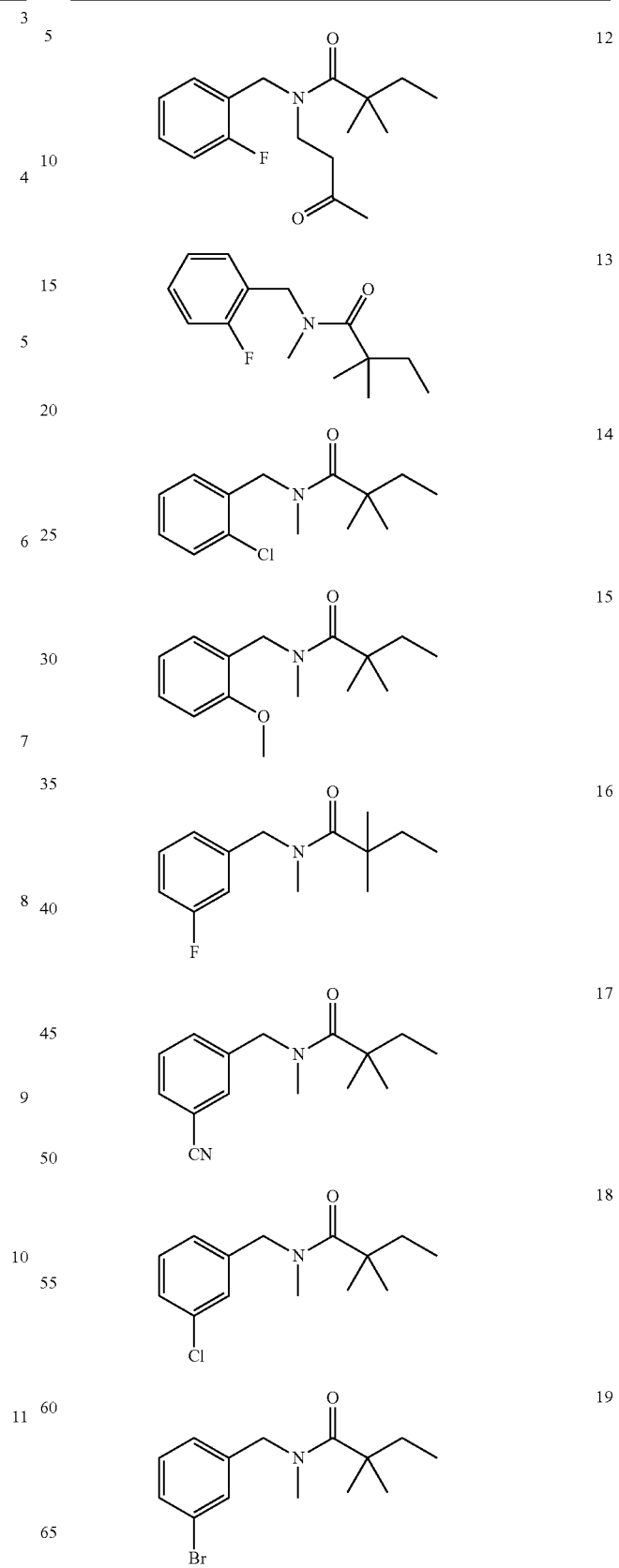

TABLE 1-continued
1. Compound List
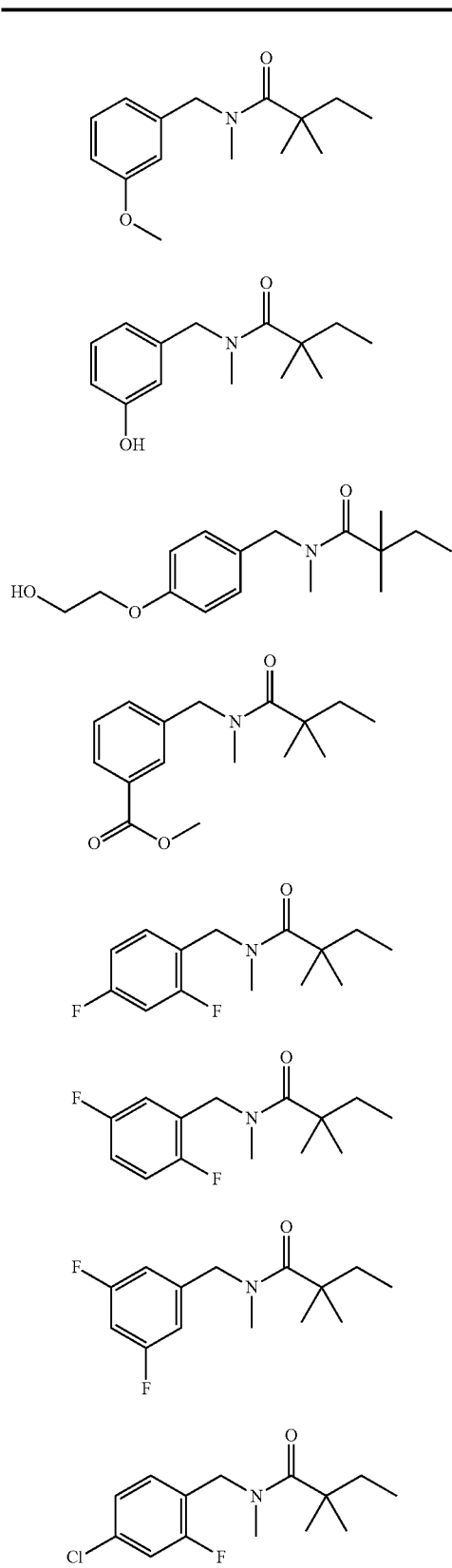
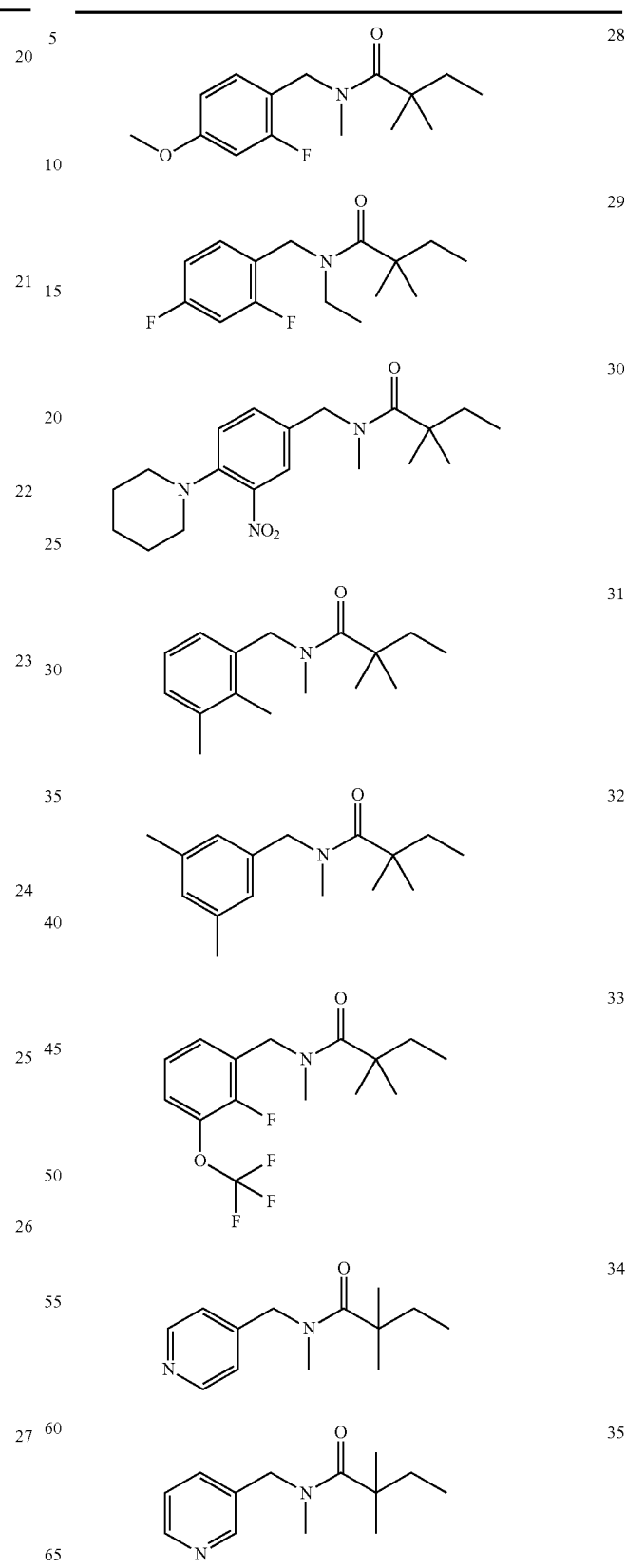

TABLE 1-continued
1. Compound List
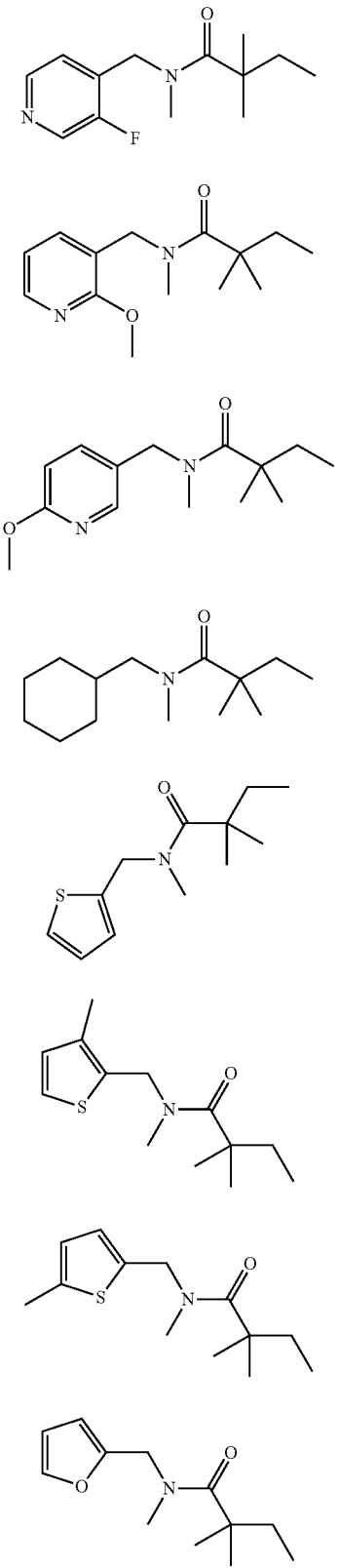
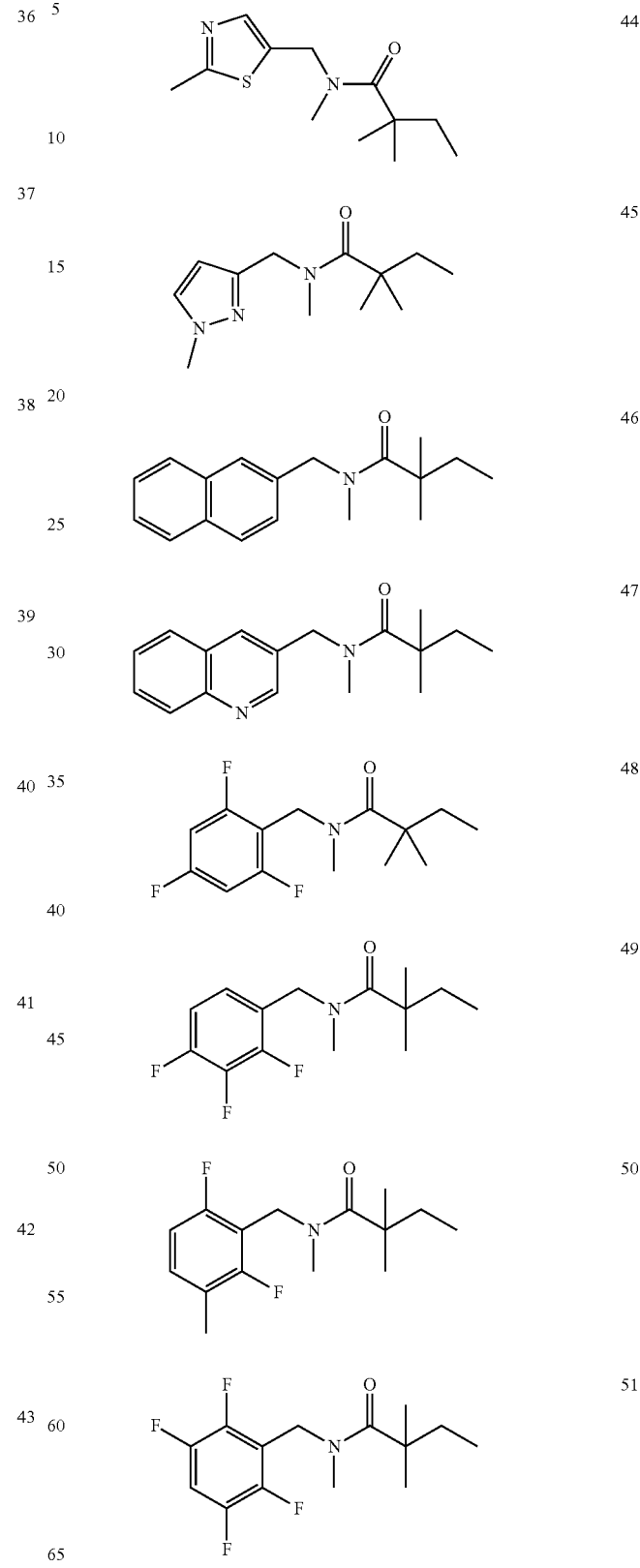

TABLE 1-continued
1. Compound List
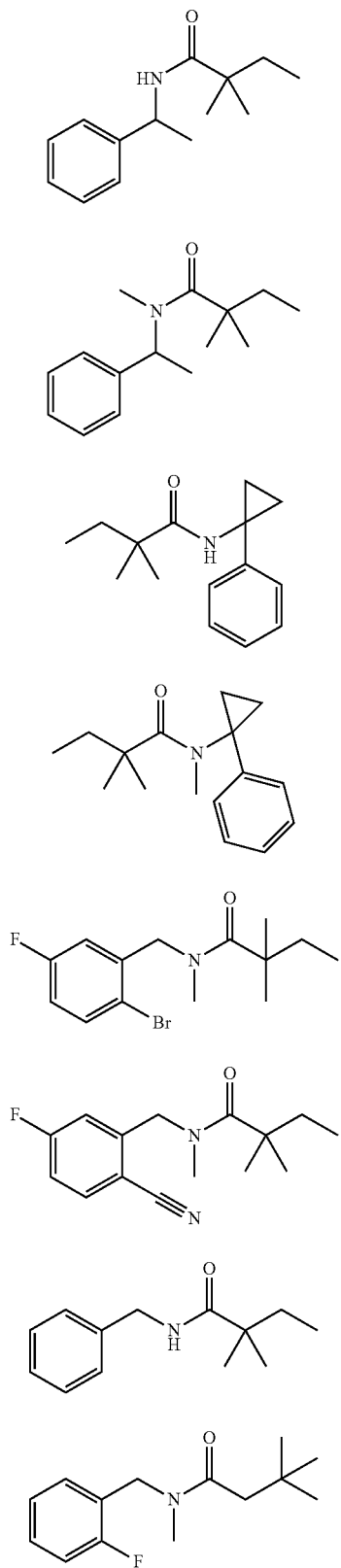
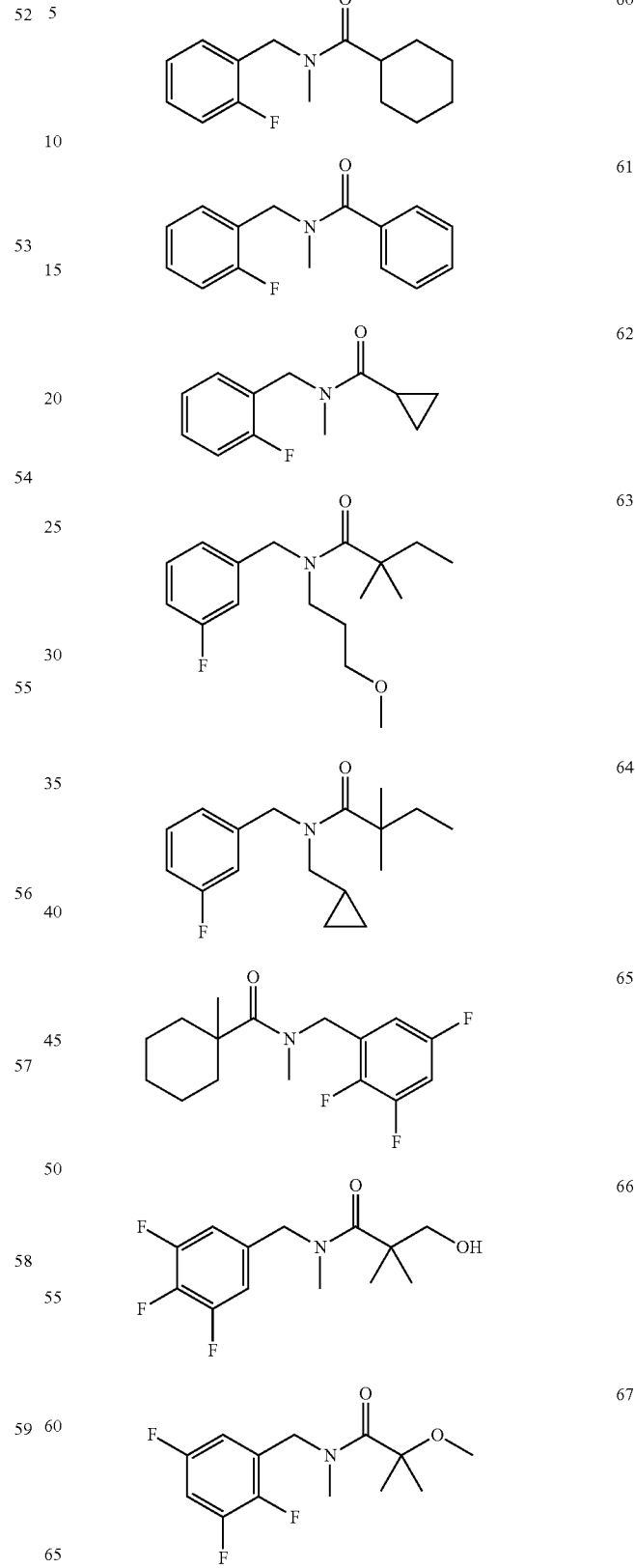

TABLE 1-continued
1. Compound List
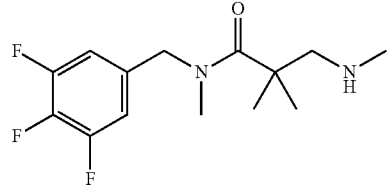 [SMILES: CNCC(C)(C)C(=O)N(C)Cc1cc(F)c(F)c(F)c1] 68
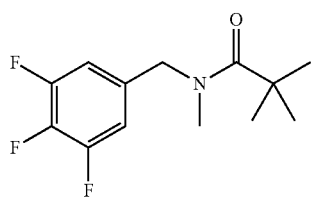 [SMILES: CN(Cc1cc(F)c(F)c(F)c1)C(=O)C(C)(C)C] 69
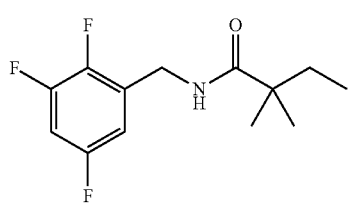 [SMILES: CCC(C)(C)C(=O)NCc1cc(F)cc(F)c1F] 70
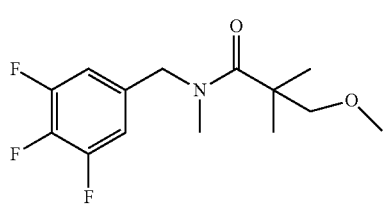 [SMILES: COCC(C)(C)C(=O)N(C)Cc1cc(F)c(F)c(F)c1] 71
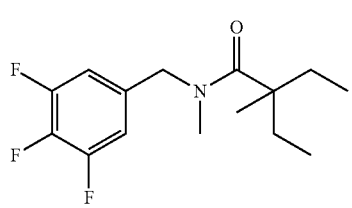 72
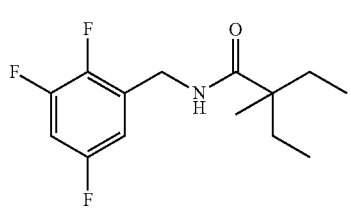 [SMILES: CCC(C)(CC)C(=O)NCc1cc(F)cc(F)c1F] 73
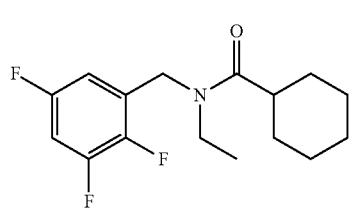 [SMILES: CCN(Cc1cc(F)cc(F)c1F)C(=O)C1CCCCC1] 74
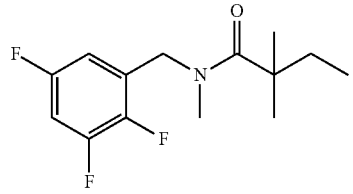 [SMILES: CCC(C)(C)C(=O)N(C)Cc1cc(F)cc(F)c1F] 75
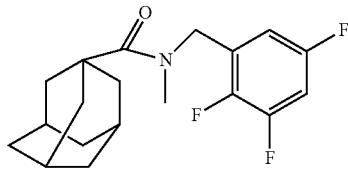 [SMILES: CN(Cc1cc(F)cc(F)c1F)C(=O)C12CC3CC(CC(C3)C1)C2] 76
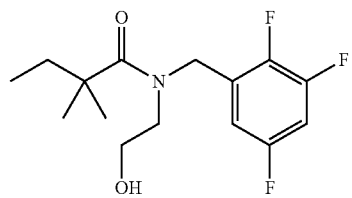 [SMILES: CCC(C)(C)C(=O)N(CCO)Cc1cc(F)cc(F)c1F] 77
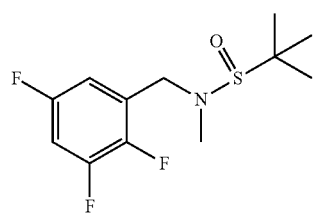 [SMILES: CN(Cc1cc(F)cc(F)c1F)S(=O)C(C)(C)C] 78
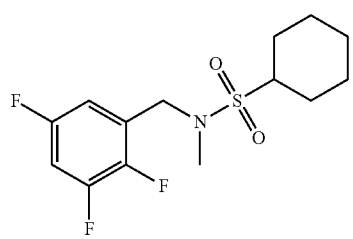 [SMILES: CN(Cc1cc(F)cc(F)c1F)S(=O)(=O)C1CCCCC1] 79
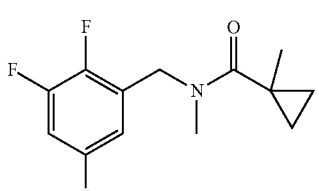 80
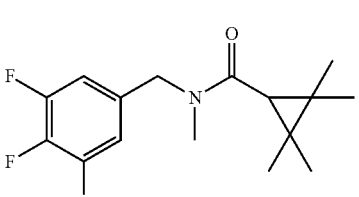 81

TABLE 1-continued
1. Compound List
| | |
|---|---|
| 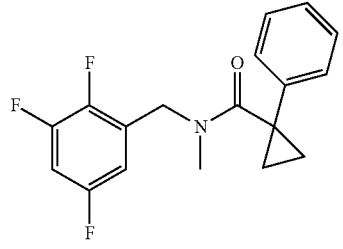 [SMILES: CN(Cc1cc(F)cc(F)c1F)C(=O)C1(c2ccccc2)CC1] | 82 |
| 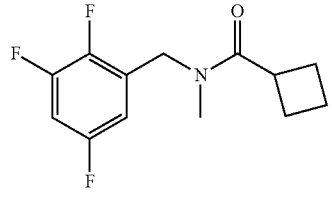 [SMILES: CN(Cc1cc(F)cc(F)c1F)C(=O)C1CCC1] | 83 |
| 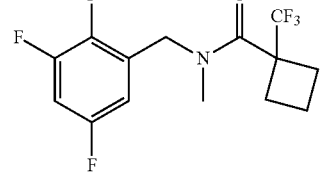 | 84 |
| 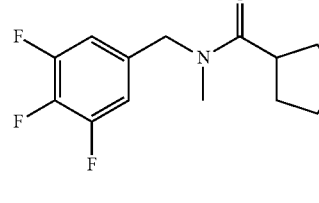 | 85 |
| 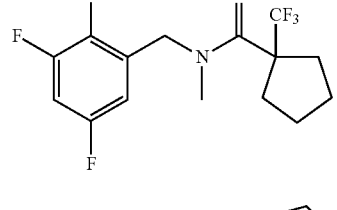 | 86 |
| 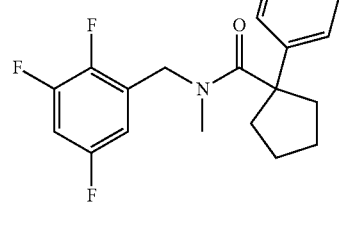 | 87 |
| 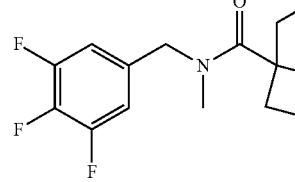 | 88 |
|  | 89 |
|  | 90 |
|  | 91 |
|  | 92 |
| 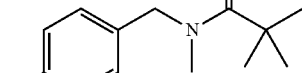 | 93 |
|  | 94 |
|  | 95 |
| 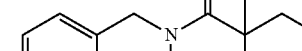 | 96 |
| 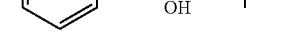 | 97 |

TABLE 1-continued
1. Compound List
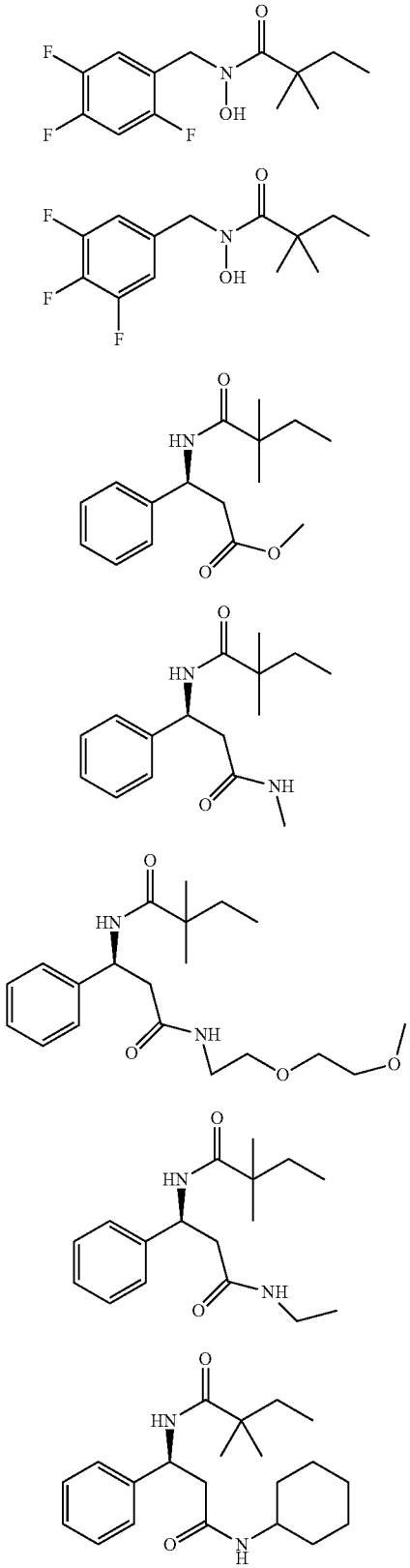
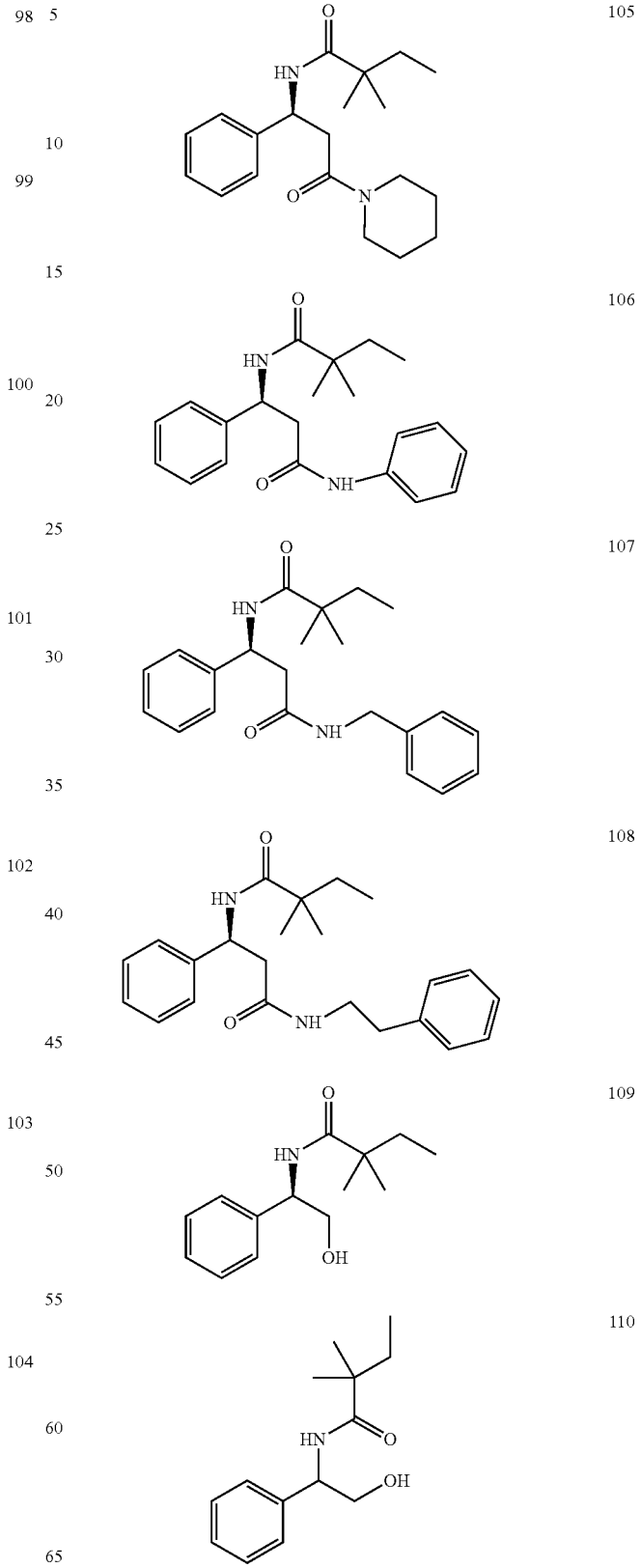

TABLE 1-continued
1. Compound List
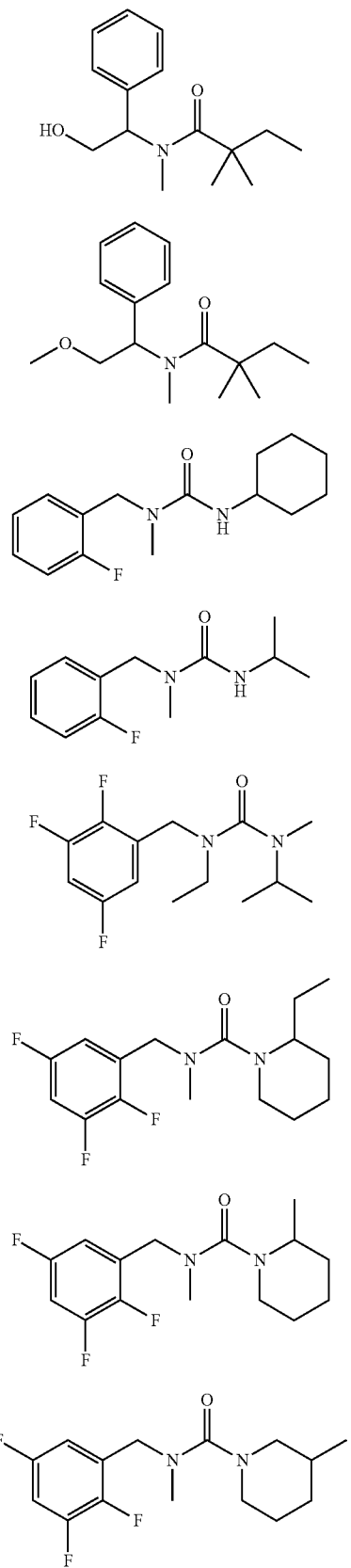
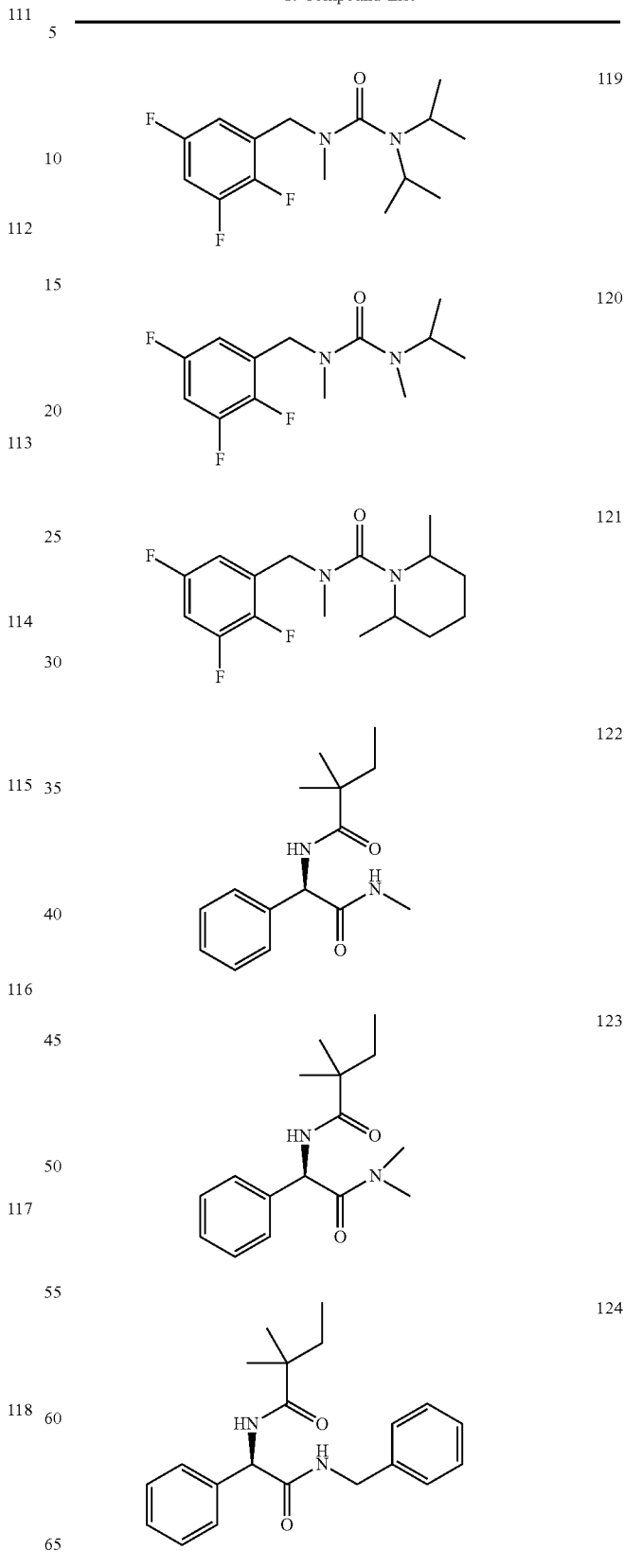

TABLE 1-continued
1. Compound List
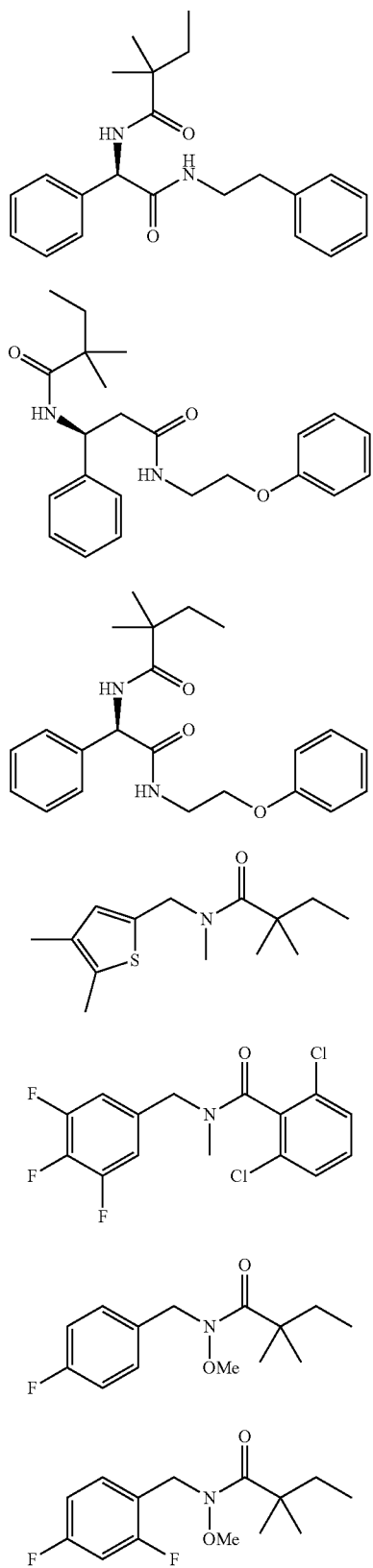
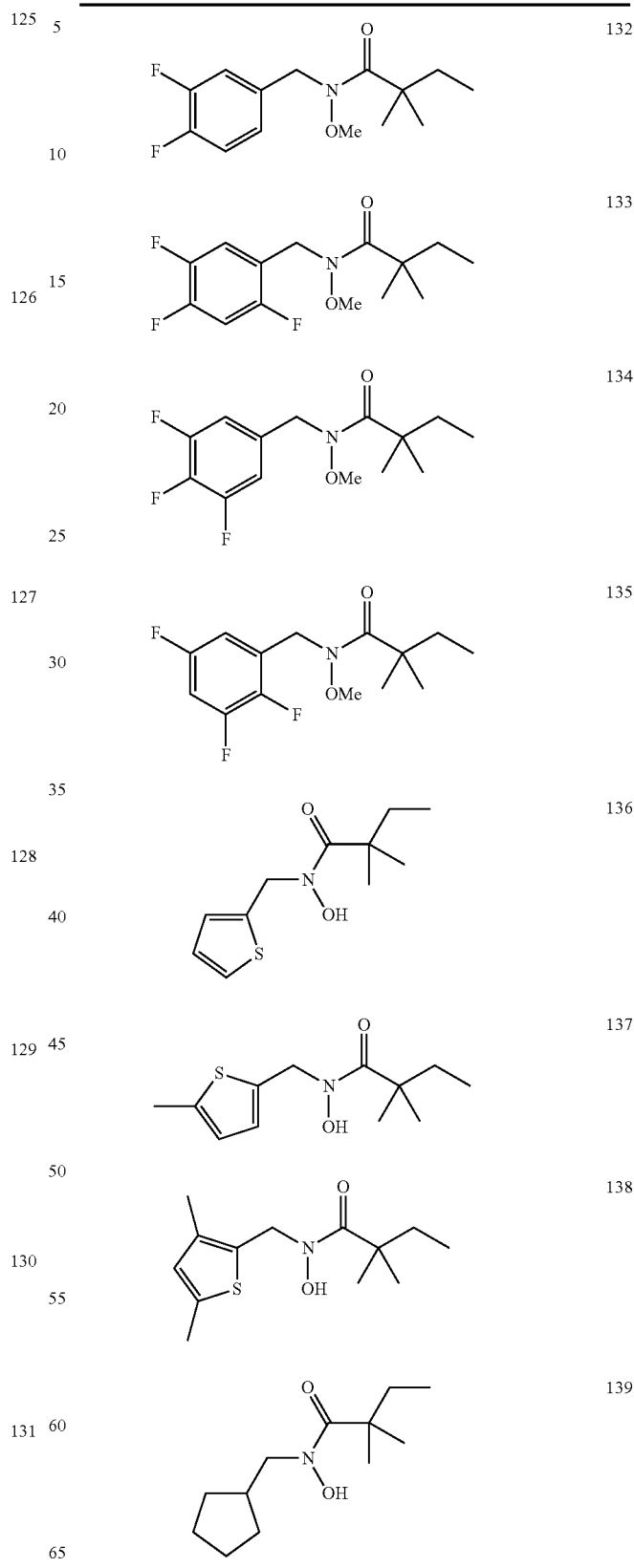

TABLE 1-continued
1. Compound List
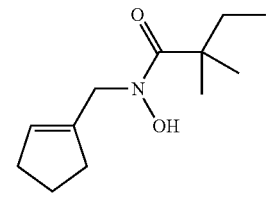 140
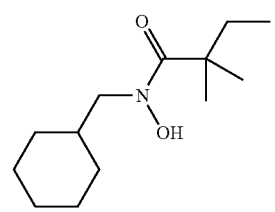 [SMILES: CCC(C)(C)C(=O)N(O)CC1CCCCC1] 141
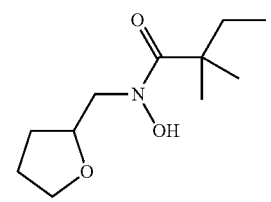 142
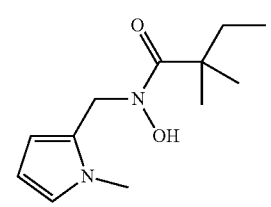 [SMILES: CCC(C)(C)C(=O)N(O)Cc1cccn1C] 143
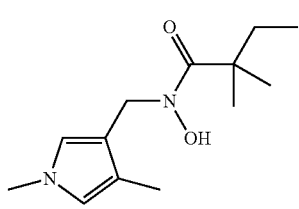 [SMILES: CCC(C)(C)C(=O)N(O)Cc1cn(C)cc1C] 144
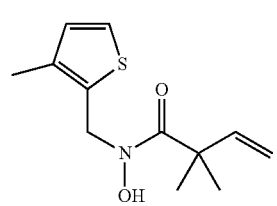 [SMILES: C=CC(C)(C)C(=O)N(O)Cc1sccc1C] 145
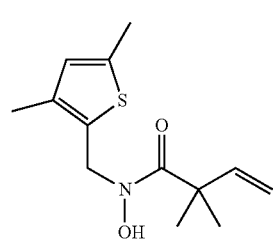 [SMILES: C=CC(C)(C)C(=O)N(O)Cc1sc(C)cc1C] 146
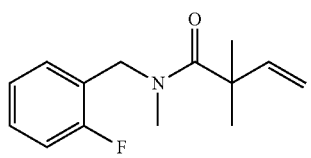 [SMILES: C=CC(C)(C)C(=O)N(C)Cc1ccccc1F] 147
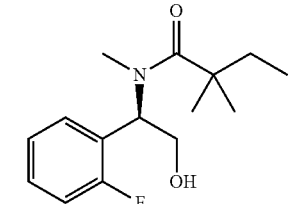 148
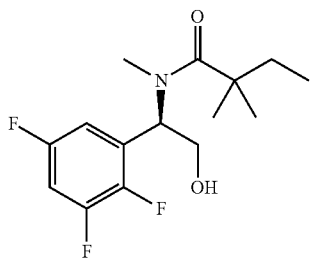 [SMILES: CCC(C)(C)C(=O)N(C)[C@@H](CO)c1cc(F)cc(F)c1F] 149
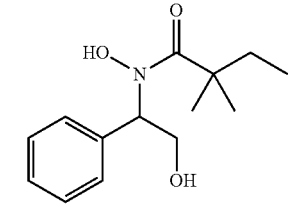 [SMILES: CCC(C)(C)C(=O)N(O)C(CO)c1ccccc1] 150
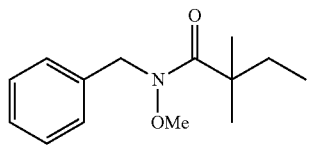 [SMILES: CCC(C)(C)C(=O)N(Cc1ccccc1)OC] 151
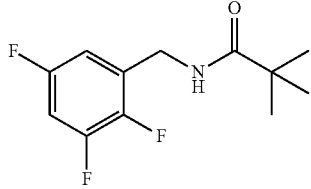 [SMILES: CC(C)(C)C(=O)NCc1cc(F)cc(F)c1F] S1
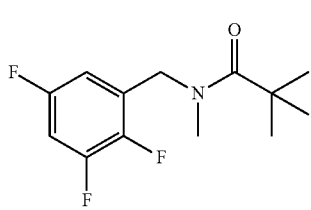 [SMILES: CN(Cc1cc(F)cc(F)c1F)C(=O)C(C)(C)C] S2

TABLE 1-continued
1. Compound List
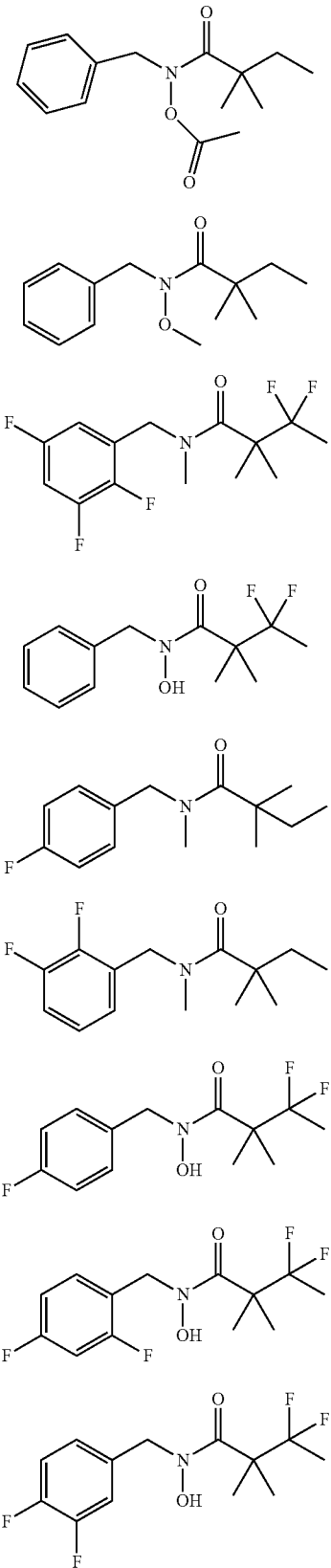
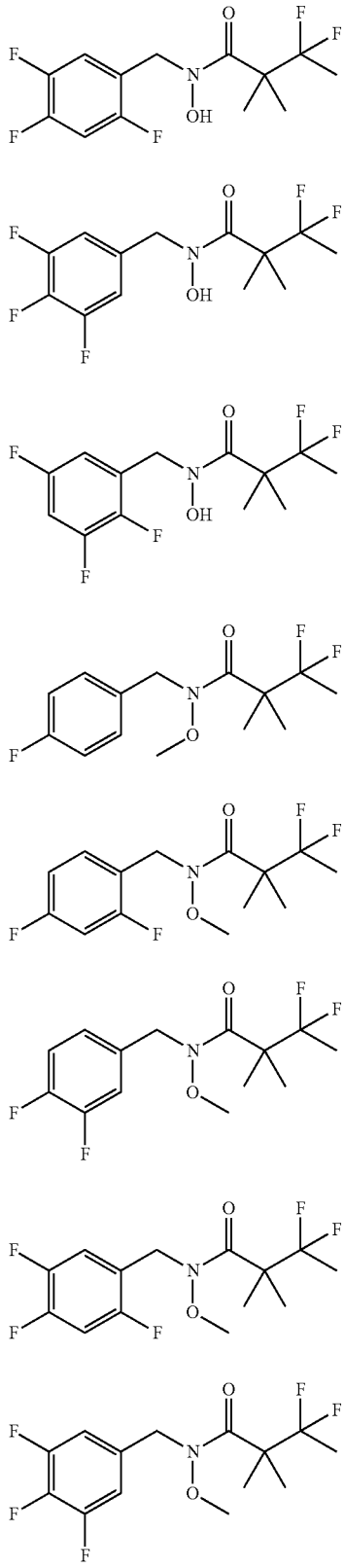

TABLE 1-continued

1. Compound List

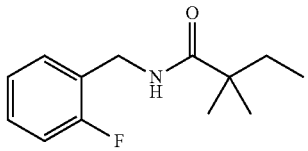 [SMILES: CCC(C)(C)C(=O)NCc1ccccc1F]
S20

2. Compound Preparation.

Compound 1 Preparation of
N-(2-fluorobenzyl)-2,2-dimethylbutanamide

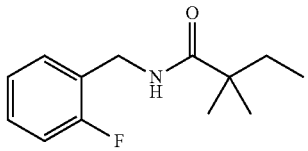 [SMILES: CCC(C)(C)C(=O)NCc1ccccc1F]

SOCl$_2$ (30 ml) was added to the 2, 2-dimethylbutanoic acid (5.22 g) in toluene with stirring. Then the reaction mixture was warmed to 80° C. for 5 h. After removal of the solvent, 4.268 g of 2,2-dimethylbutanoyl chloride was obtained, which was dissolved in DCM and added dropwise to the (2-fluorophenyl)methanamine (1.698 g) dissolved in DCM contains TEA (4.8 g) at 0° C. Stirring was continued at room temperature for 10 h. After all amines had been consumed as judged by TLC, the mixture was quenched with ice-water. Extracted with DCM, dried over Na$_2$SO$_4$, concentrated and purified by silica gel chromatography to give the desired product (2.57 g, 72.6%). $^1$H NMR (CDCl$_3$): δ 7.30-7.34 (m, 1H), 7.23-7.25 (m, 1H), 7.00-7.11 (m, 2H), 6.06 (br, 1H), 4.48 (d, 2H, J=6.0 Hz), 1.55 (q, 2H, J=7.6 Hz), 1.16 (s, 6H), 0.81 (t, 3H, J=7.6 Hz).

Compound 2 Preparation of N-benzylpivalamide

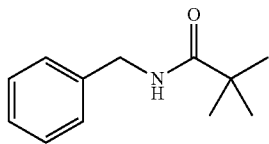

Phenylmethanamine (80.3 mg) and triethylamine (0.625 ml) were dissolved in DCM (2 ml), pivaloyl chloride (120 mg) was added at 0° C. and the mixture was stirred at room temperature for 3 h. The mixture was quenched with ice-water. Extracted with DCM, dried over Na$_2$SO$_4$, concentrated and purified by silica gel chromatography to give the desired product (58.6 mg, 40.9%). $^1$H NMR (CDCl$_3$): δ 7.25-7.37 (m, 5H), 5.89 (br, 1H), 4.45 (d, 2H, J=5.6 Hz), 1.23 (s, 9H).

Compound 3 Preparation of
N-(2-bromobenzyl)-2,2-dimethylbutanamide

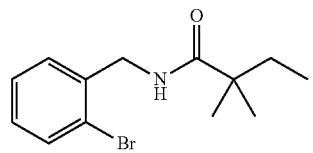

The titled compound 3 was prepared in 58.3% from (2-bromophenyl)methanamine (93 mg) and 2,2-dimethylbutanoyl chloride (80.76 mg) according to the procedure outlined for compound 1. $^1$H NMR (CDCl$_3$): δ 7.55 (d, 1H, J=8.0 Hz), 7.37-7.40 (m, 1H), 7.26-7.30 (m, 1H), 7.12-7.17 (m, 1H) 6.14 (br, 1H), 4.50 (d, 2H, J=6.0 Hz), 1.55 (q, 2H, J=7.6 Hz), 1.16 (s, 6H), 0.80 (t, 3H, J=7.6 Hz).

Compound 4 Preparation of 2,2-dimethyl-N-(2-(trifluoromethyl)benzyl)butanamide

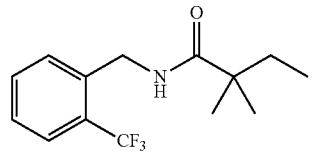 [SMILES: CCC(C)(C)C(=O)NCc1ccccc1C(F)(F)F]

The titled compound 4 was prepared in 71% from 2-(trifluoromethyl)phenyl)-methanamine (87.6 mg) and 2,2-dimethylbutanoyl chloride (105 mg) according to the procedure outlined for compound 1. $^1$H NMR (CDCl$_3$): δ 7.64-7.66 (d, 1H, J=8.0 Hz), 7.50-7.56 (m, 2H), 7.36-7.40 (m, 1H), 5.97 (br, 1H), 4.62 (d, 2H, J=4.8 Hz), 1.55 (q, 2H, J=7.6 Hz), 1.15 (s, 6H), 0.80 (t, 3H, J=7.6 Hz).

Compound 5 Preparation of
N-(3-fluorobenzyl)-2,2-dimethylbutanamide

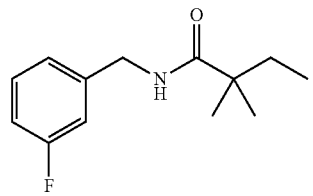

The titled compound 5 was prepared in 70% yield from (3-fluorophenyl)methanamine (93 mg) and 2,2-dimethylbutanoyl chloride (80.74 mg) according to the procedure outlined for compound 1. $^1$H NMR (400 MHz, CDCl$_3$) δ: 7.33-7.27 (m, 1H), 7.04 (d, J=8.0 Hz, 1H), 6.93-6.98 (m, 2H), 4.45 (d, J=5.8 Hz, 2H), 1.58 (q, J=7.5 Hz, 3H), 1.19 (s, 6H), 0.86 (t, J=7.5 Hz, 3H).

Compound 6 Preparation of N-(3-bromobenzyl)-2,2-dimethylbutanamide

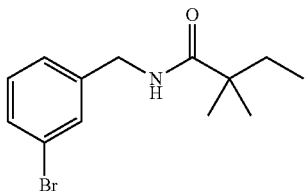 [SMILES: CCC(C)(C)C(=O)NCc1cccc(Br)c1]

The titled compound 6 was prepared in 87% from (3-bromophenyl)methanamine (93 mg) and 2,2-dimethylbutanoyl chloride (105 mg) according to the procedure outlined for compound 1. $^1$H NMR (CDCl$_3$): δ 7.38-7.41 (m, 2H), 7.17-7.21 (m, 2H), 5.96 (br, 1H), 4.42 (d, 2H, J=6.0 Hz), 1.55 (q, 2H, J=7.6 Hz), 1.15 (s, 6H), 0.80 (t, 3H, J=7.6 Hz).

Compound 7 Preparation of N-(2,4-difluorobenzyl)-2,2-dimethylbutanamide

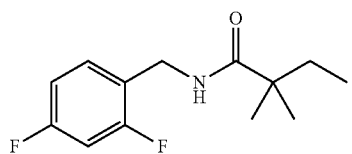 [SMILES: CCC(C)(C)C(=O)NCc1ccc(F)cc1F]

The titled compound 7 was prepared in 40.9% yield form (2,4-difluorophenyl)methanamine (228.8 mg) and 2,2-dimethylbutanoyl chloride (430.3 mg) according to the procedure outlined for compound 1. $^1$H NMR (CDCl$_3$): δ 7.30-7.36 (m, 1H), 6.77-6.86 (m, 2H), 5.97 (br, 1H), 4.44 (d, 2H, J=6.0 Hz), 1.55 (q, 2H, J=7.6 Hz), 1.17 (s, 6H), 0.80 (t, 3H, J=7.6 Hz).

Compound 8 Preparation of N-(3,4-difluorobenzyl)-2,2-dimethylbutanamide

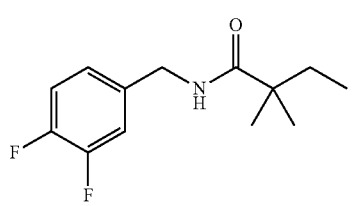

The titled compound 8 was prepared in 71.3% yield form (3,4-difluorophenyl)methanamine (114.4 mg) and 2,2-dimethylbutanoyl chloride (215 mg) according to the procedure outlined for compound 1. $^1$H NMR (CDCl$_3$): δ 7.06-7.14 (m, 2H), 6.97-7.00 (m, 1H), 5.95 (br, 1H), 4.40 (d, 2H, J=6.0 Hz), 1.56 (q, 2H, J=7.6 Hz), 1.17 (s, 6H), 0.84 (t, 3H, J=7.6 Hz).

Compound 9 Preparation of 2,2-dimethyl-N-(pyridin-3-ylmethyl)butanamide

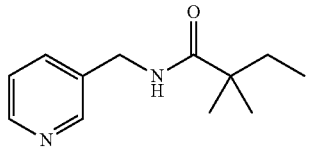

The titled compound 9 was prepared in 51.2% yield form pyridin-3-ylmethanamine (54.07 mg) and 2,2-dimethylbutanoyl chloride (134.6 mg) according to the procedure outlined for compound 1. $^1$H NMR (CDCl$_3$): δ 8.52 (s, 2H) 7.61-7.64 (m, 1H), 7.25-7.28 (m, 1H), 6.05 (br, 1H), 4.47 (d, 2H, J=6.0 Hz), 1.58 (q, 2H, J=7.6 Hz), 1.18 (s, 6H), 0.84 (t, 3H, J=7.6 Hz).

Compound 10 Preparation of N-ethyl-N-(2-fluorobenzyl)-2,2-dimethylbutanamide

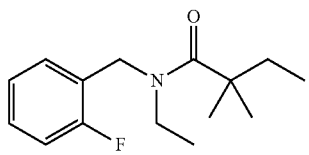 [SMILES: CCN(Cc1ccccc1F)C(=O)C(C)(C)CC]

N-(2-fluorobenzyl)-2,2-dimethylbutanamide (40 mg) was dissolved in 4 ml of dry DMF, 8.61 mg of NaH was added at 0° C. under N2 and stirred for 2 h. Iodoethane (56.2 mg) was added and the mixture was allowed to warm to room temperature and stirred for 11 h. The mixture was quenched with cold water and extracted with DCM, the combined organic layers was washed with water, brine, dried over Na$_2$SO$_4$, concentrated and the residue was purified by silica gel column chromatography to give the product (9.3 mg, 20.6%). $^1$H NMR (CDCl$_3$): δ 7.22-7.26 (m, 2H), 7.03-7.12 (m, 2H), 4.69 (s, 2H), 3.43 (d, 2H, J=5.2 Hz), 1.67 (q, 2H, J=7.6 Hz), 1.26 (s, 6H), 1.17 (t, 3H, J=6.8 Hz), 0.89 (t, 3H, J=7.6 Hz).

Compound 11 Preparation of N-(2-fluorobenzyl)-2,2-dimethyl-N-(prop-2-yn-1-yl)butanamide

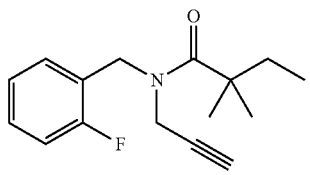 [SMILES: C#CCN(Cc1ccccc1F)C(=O)C(C)(C)CC]

N-(2-fluorobenzyl)prop-2-yn-1-amine was prepared in 42% yield according to the procedure outlined for compound 10, 68.2 mg of the amide was used as starting Material and reacted with 2,2-dimethylbutanoyl chloride (170 mg) and the desired compound 11 was prepared in 30% yield. $^1$H NMR (CDCl$_3$): δ 7.23-7.26 (m, 2H), 7.03-7.13 (m, 2H), 4.83 (s, 2H), 4.15 (d, 2H, J=2.4 Hz), 2.23 (t, 1H, J=2.4 Hz), 1.70 (q, 2H, J=7.6 Hz), 1.29 (s, 6H), 0.89 (t, 3H, J=7.6 Hz).

Compound 12 Preparation of N-(2-fluorobenzyl)-2,2-dimethyl-N-(3-oxobutyl)butanamide

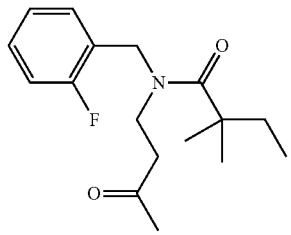 [SMILES: CCC(C)(C)C(=O)N(CCC(C)=O)Cc1ccccc1F]

A mixture of (2-fluorophenyl)methanamine (125 mg), paraformaldehyde (36 mg), acetone (116 mg) and concentrated hydrochloric acid (0.1 ml) in EtOH (1 ml) was heated in a sealed flask at 110° C. for 16 h After the mixture was cooled to room temperature, the solvent was removed and EtOAc was added, the resulting suspension was vigorously stirred for 1 h and then filtered and washed with EtOAc to afford 200 mg of 4-((2-fluorobenzyl)amino)butan-2-one, which was used directly in the next step without further purification.

The resulting amide (200 mg) was dissolve in dry THF (10 ml), and TEA (0.3 ml) was added. The mixture was cooled to 0° C., 2,2-dimethylbutanoylchloride (274 mg) was added and stirred for 4 h at room temperature. The mixture was quenched with water and extracted with EtOAc. The combined organic layer were washed with brine and dried over $Na_2SO_4$. After removal of the solvent, the residue was purified by silica gel chromatography to afford the compound 12 (180 mg, 60%). $^1$H NMR (CDCl$_3$): δ 7.23-7.28 (m, 1H), 7.10-7.19 (m, 2H), 7.02-7.07 (m, 1H), 4.75 (s, 2H), 3.54 (br, 2H), 2.77 (t, 2H, J=7.2 Hz), 2.13 (s, 3H), 1.66 (q, 2H, J=7.6 Hz), 1.23 (s, 6H), 0.89 (t, 3H, J=7.6 Hz).

Compound 13: Preparation of N-(2-fluorobenzyl)-N,2,2-trimethylbutanamide

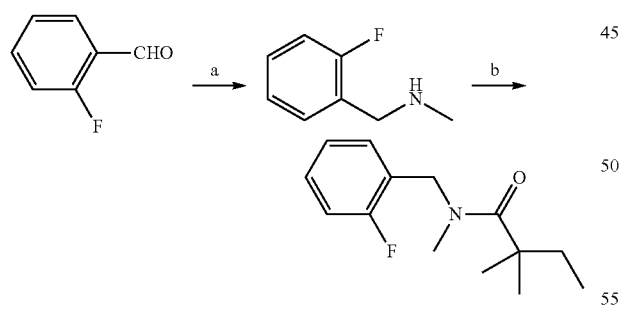

Reagent and conditions: (a): (1) CH$_3$NH$_2$.HCl, K$_2$CO$_3$, MeOH, rt, 1.5 h; (b): NaBH$_4$ (c) 2, 2-dimethylbutanoyl chloride, DIEA, THF, rt, 2 h.

A mixture of K$_2$CO$_3$ (207 mg, 1.5 mmoL) and methanamine hydrochloride (202 mg, 3.0 mmoL) in 5 mL of MeOH was stirred at room temperature for 30 min. Then 2-fluorobenzaldehyde (248 mg, 2.0 mmoL) was added to the mixture and stirred at room temperature for 1 h. The mixture was cooled to 0° C., and NaBH$_4$ (113.5 mg, 3.0 mmoL) was added in portions. The mixture was stirred at 0° C. for 1 h. The solid was filtered and washed with EtOAc. The filtrate was evaporated to dryness and the residue was dissolved in EtOAc and was washed with water, brine, dried over Na$_2$SO$_4$. The residue was dissolved in 10 mL of dry THF. DIEA (264 mg, 2.05 mmoL) was added, 2,2-dimethylbutanoyl chloride (275 mg, 2.05 mmoL) was added slowly to the solution at 0° C. under nitrogen, then stirred at room temperature for 2 h. 15 mL of water was added to the solution and extracted with EtOAc (10 mL×3). The combined organic was washed with 1M HCl, brine, dried with Na$_2$SO$_4$ and concentrated in vacuo. The residue was purified by silica gel column chromatography (PE/EA=1/2) to give the 230 mg of 1 as a brown solid (total yield=45.1%). $^1$H NMR (CDCl$_3$, 400 M Hz): δ (ppm) 7.22-7.28 (m, 2H), 7.01-7.12 (m, 2H), 4.68 (s, 2H), 3.05 (s, 3H), 1.65 (q, 2H, J=7.6 Hz), 1.27 (s, 6H), 0.89 (t, 3H, J=7.6 Hz) LC-MS (ESI) [M+]$^+$ calcd for C$_{14}$H$_{20}$FNO, 238.2. found, 238.4.

Compound 14: Preparation of N-(2-chlorobenzyl)-N,2,2-trimethylbutanamide

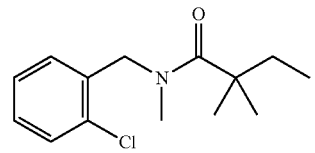 [SMILES: CCC(C)(C)C(=O)N(C)Cc1ccccc1Cl]

The titled compound 14 was prepared in 48% yield from 2-chlorobenzaldehyde (281 mg), methanamine hydrochloride (202 mg) and 2,2-dimethylbutanoyl chloride (275 mg) according to the procedure outlined for compound 13. $^1$H NMR (CDCl$_3$, 400 M Hz): δ7.35-7.37 (m, 1H), 7.16-7.25 (m, 3H), 4.74 (s, 2H), 3.05 (s, 3H), 1.70 (q, 2H, J=7.6 Hz), 1.28 (s, 6H), 0.91 (t, 3H, J=7.6 Hz). LC-MS (ESI) [M+H]$^+$ calcd for C$_{14}$H$_{20}$ClNO, 254.2. found, 254.4.

Compound 15: Preparation of N-(2-methoxybenzyl)-N,2,2-trimethylbutanamide

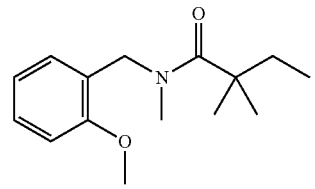 [SMILES: CCC(C)(C)C(=O)N(C)Cc1ccccc1OC]

The titled compound 15 was prepared in 65% yield from 2-methoxybenzaldehyde (136 mg), methanamine hydrochloride (101 mg) and 2,2-dimethylbutanoyl chloride (140 mg) according to the procedure outlined for compound 13. $^1$H NMR (CDCl$_3$, 400 M Hz): δ7.21-7.26 (m, 1H), 7.09-7.13 (m, 1H), 6.86-6.95 (m, 2H), 4.66 (s, 2H), 3.83 (s, 3H), 2.99 (s, 3H), 1.68 (q, 2H, J=7.6 Hz), 1.26 (s, 6H), 0.90 (t, 3H, J=7.6 Hz) LC-MS (ESI) [M+H]$^+$ calcd for C$_{15}$H$_{23}$NO$_2$, 250.1. found 250.3.

Compound 16: Preparation of
N-(3-fluorobenzyl)-N,2,2-trimethylbutanamide

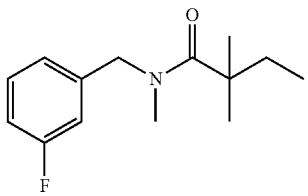 [SMILES: CCC(C)(C)C(=O)N(C)Cc1cccc(F)c1]

The titled compound 16 was prepared in 65% yield from 3-fluorobenzaldehyde (124 mg), methanamine hydrochloride (101 mg) and 2,2-dimethylbutanoyl chloride (140 mg) according to the procedure outlined for compound 13. $^1$H NMR (CDCl$_3$, 400 M Hz): δ7.25-7.31 (m, 1H), 6.91-7.01 (m, 3H), 4.61 (s, 2H), 3.01 (s, 3H), 1.69 (q, 2H, J=7.6 Hz), 1.29 (s, 6H), 0.90 (t, 3H, J=7.6 Hz). LC-MS (ESI) [M+H]$^+$ calcd for C$_{14}$H$_{20}$FNO, 238.1. found 238.4.

Compound 17: Preparation of
N-(3-cyanobenzyl)-N,2,2-trimethylbutanamide

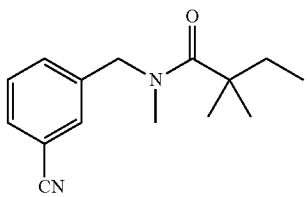

The titled compound 17 was prepared in 62% yield from 3-formylbenzonitrile (131 mg), methanamine hydrochloride (101 mg) and 2,2-dimethylbutanoyl chloride (140 mg) according to the procedure outlined for compound 13. $^1$H NMR (CDCl$_3$, 400 M Hz): δ7.41-7.56 (m, 4H), 4.61 (s, 2H), 3.05 (s, 3H), 1.68 (q, 2H, J=7.6 Hz), 1.28 (s, 6H), 0.88 (t, 3H, J=7.6 Hz). LC-MS (ESI) [M+H]$^+$ calcd for C$_{15}$H$_{20}$N$_2$O, 245.1. found 245.3.

Compound 18: Preparation of
N-(3-chlorobenzyl)-N,2,2-trimethylbutanamide

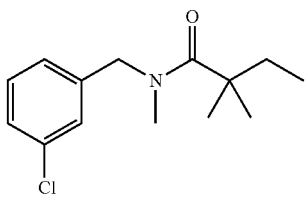

The titled compound 18 was prepared in 48% yield from 3-chlorobenzaldehyde (140 mg), methanamine hydrochloride (101 mg) and 2,2-dimethylbutanoyl chloride (140 mg) according to the procedure outlined for compound 13. $^1$H NMR (CDCl$_3$, 400 M Hz): δ7.20-7.26 (m, 3H), 7.10-7.12 (m, 1H), 4.59 (s, 2H), 3.01 (s, 3H), 1.68 (q, 2H, J=7.6 Hz), 1.28 (s, 6H), 0.90 (t, 3H, J=7.6 Hz). LC-MS (ESI) [M+H]$^+$ calcd for C$_{14}$H$_{20}$ClNO, 254.1. found 254.3.

Compound 19: Preparation of
N-(3-bromobenzyl)-N,2,2-trimethylbutanamide

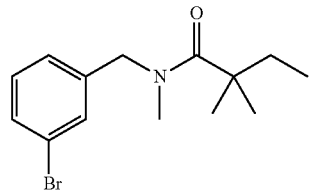

The titled compound 19 was prepared in 48% yield from 3-bromobenzaldehyde (185 mg), methanamine hydrochloride (101 mg) and 2,2-dimethylbutanoyl chloride (140 mg) according to the procedure outlined for compound 13. $^1$H NMR (CDCl$_3$, 400 M Hz): δ 7 7.36-7.40 (m, 2H), 7.16-7.22 (m, 2H), 4.59 (s, 2H), 3.01 (s, 3H), 1.69 (q, 2H, J=7.6 Hz), 1.29 (s, 6H), 0.90 (t, 3H, J=7.6 Hz). LC-MS (ESI) [M+H]$^+$ calcd for C$_{14}$H$_{20}$BrNO, 298.1. found, 298.3, 300.4.

Compound 20: Preparation of
N-(3-methoxybenzyl)-N,2,2-trimethylbutanamide

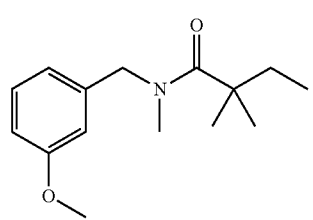 [SMILES: CCC(C)(C)C(=O)N(C)Cc1cccc(OC)c1]

The titled compound 8 was prepared in 57% yield from 3-methoxybenzaldehyde (136 mg), methanamine hydrochloride (101 mg) and 2,2-dimethylbutanoyl chloride (140 mg) according to the procedure outlined for compound 13. $^1$H NMR (CDCl$_3$, 400 M Hz): δ7.22-7.25 (m, 1H), 6.76-6.81 (m, 3H), 4.61 (s, 2H), 3.78 (s, 3H), 2.98 (s, 3H), 1.69 (q, 2H, J=7.6 Hz), 1.29 (s, 6H), 0.91 (t, 3H, J=7.6 Hz). LC-MS (ESI) [M+H]$^+$ calcd for C$_{15}$H$_{23}$NO$_2$, 250.2. found 250.4.

Compound 21: Preparation of
N-(3-hydroxybenzyl)-N,2,2-trimethylbutanamide

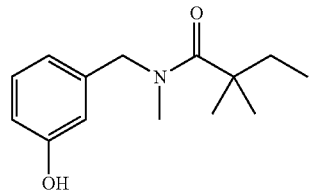

The titled compound 21 was prepared in 33% yield from 3-hydroxybenzaldehyde (122 mg), methanamine hydrochloride (101 mg) and 2,2-dimethylbutanoyl chloride (140 mg) according to the procedure outlined for compound 1. $^1$H NMR (CDCl$_3$, 400 M Hz): δ7.17 (t, 1H, J=7.6 Hz), 6.71-6.79 (m, 3H), 4.58 (s, 2H), 2.98 (s, 3H), 1.68 (q, 2H, J=7.6

Hz), 1.29 (s, 6H), 0.90 (t, 3H, J=7.6 Hz). LC-MS (ESI) [M+H]+ calcd for C14H21NO2, 236.2. found, 236.4.

Compound 22: Preparation of N-(3-(2-hydroxyethoxy)benzyl)-N,2,2-trimethylbutanamide

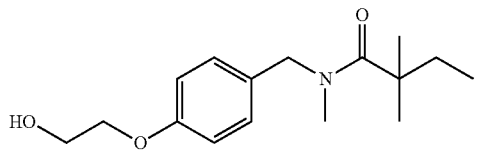 [SMILES: CCC(C)(C)C(=O)N(C)Cc1ccc(OCCO)cc1]

The titled compound 22 was prepared in 48% yield from 4-(2-hydroxyethoxy)benzaldehyde (166 mg), methanamine hydrochloride (101 mg) and 2,2-dimethylbutanoyl chloride (140 mg) according to the procedure outlined for compound 13. $^1$H NMR (CDCl$_3$, 400 M Hz): δ7.14-7.17 (m, 2H), 6.85-6.89 (m, 2H), 4.56 (s, 2H), 4.06-4.08 (m, 2H), 3.94-3.96 (m, 2H), 2.96 (s, 3H), 1.67 (q, 2H, J=7.6 Hz), 1.27 (s, 6H), 0.88 (t, 3H, J=7.6 Hz). LC-MS (ESI) [M+H]+ calcd for C16H25NO3, 280.2. found, 280.4.

Compound 23

Preparation of methyl 3-((N,2,2-trimethylbutanamido)methyl)benzoate

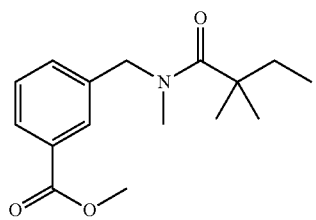 [SMILES: CCC(C)(C)C(=O)N(C)Cc1cccc(C(=O)OC)c1]

The titled compound 23 was prepared in 46% yield from methyl 3-formylbenzoate (164 mg), methanamine hydrochloride (101 mg) and 2,2-dimethylbutanoyl chloride (140 mg) according to the procedure outlined for compound 13. $^1$H NMR (CDCl$_3$, 400 M Hz): δ7.87-7.94 (m, 2H), 7.38-7.45 (m, 2H), 4.66 (s, 2H), 3.90 (s, 3H), 3.01 (s, 3H), 1.69 (q, 2H, J=7.6 Hz), 1.29 (s, 6H), 0.90 (t, 3H, J=7.6 Hz). LC-MS (ESI) [M+H]+ calcd for: C16H23NO3, 278.2. found, 278.4.

Compound 24: Preparation of N-(2,4-difluorobenzyl)-N,2,2-trimethylbutanamide

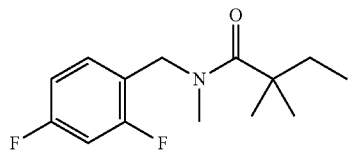 [SMILES: CCC(C)(C)C(=O)N(C)Cc1ccc(F)cc1F]

The titled compound 24 was prepared in 56% yield from 2,4-difluorobenzaldehyde (284 mg), methanamine hydrochloride (202 mg) and 2,2-dimethylbutanoyl chloride (275 mg) according to the procedure outlined for compound 13. $^1$H NMR (CDCl$_3$, 400 M Hz): δ7.25-7.31 (m, 1H), 6.76-6.86 (m, 2H), 4.60 (s, 2H), 3.06 (s, 3H), 1.65 (q, 2H, J=7.6 Hz), 1.26 (s, 6H), 0.85 (t, 3H, J=7.6 Hz). LC-MS (ESI) [M+H]+ calcd for: C14H19F2NO, 256.1. found, 256.3.

Compound 25: Preparation of N-(2,5-difluorobenzyl)-N,2,2-trimethylbutanamide

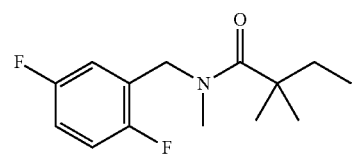 [SMILES: CCC(C)(C)C(=O)N(C)Cc1cc(F)ccc1F]

The titled compound 25 was prepared in 59% yield from 2,5-difluorobenzaldehyde (284 mg), methanamine hydrochloride (202 mg) and 2,2-dimethylbutanoyl chloride (275 mg) according to the procedure outlined for compound 13. $^1$H NMR (CDCl$_3$, 400 M Hz): δ6.89-7.02 (m, 3H), 4.63 (s, 2H), 3.08 (s, 3H), 1.68 (q, 2H, J=7.6 Hz), 1.28 (s, 6H), 0.88 (t, 3H, J=7.6 Hz). LC-MS (ESI) [M+H]+ calcd for: C14H19F2NO, 256.1. found, 256.4.

Compound 26: Preparation of N-(3,5-difluorobenzyl)-N,2,2-trimethylbutanamide

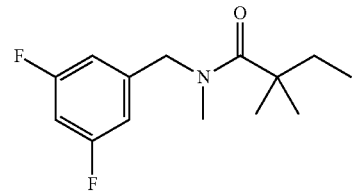 [SMILES: CCC(C)(C)C(=O)N(C)Cc1cc(F)cc(F)c1]

The titled compound 14 was prepared in 59% yield from 3,5-difluorobenzaldehyde (284 mg), methanamine hydrochloride (202 mg) and 2,2-dimethylbutanoyl chloride (275 mg) according to the procedure outlined for compound 1. $^1$H NMR (CDCl$_3$, 400 M Hz): δ6.89-6.75 (m, 3H), 4.57 (s, 2H), 3.04 (s, 3H), 1.69 (q, 2H, J=7.6 Hz), 1.29 (s, 6H), 0.90 (t, 3H, J=7.6 Hz). LC-MS (ESI) [M+H]+ calcd for: C14H19F2NO, 256.1. found, 256.3.

Compound 27: Preparation of N-(4-chloro-2-fluorobenzyl)-N,2,2-trimethylbutanamide

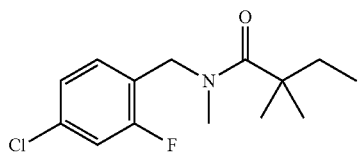 [SMILES: CCC(C)(C)C(=O)N(C)Cc1ccc(Cl)cc1F]

The titled compound 27 was prepared in 59% yield from 4-chloro-2-fluorobenzaldehyde (316 mg), methanamine hydrochloride (202 mg) and 2,2-dimethylbutanoylchloride (275 mg) according to the procedure outlined for compound 13. $^1$H NMR (CDCl$_3$, 400 M Hz): δ7.21-7.26 (m, 1H), 7.05-7.11 (m, 2H), 4.60 (s, 2H), 3.06 (s, 3H), 1.65 (q, 2H, J=7.6 Hz), 1.26 (s, 6H), 0.85 (t, 3H, J=7.6 Hz). LC-MS (ESI) [M+H]+ calcd for: $C_{14}H_{19}ClFNO$, 272.1. found, 272.4.

Compound 28: Preparation of N-(2-fluoro-4-methoxybenzyl)-N,2,2-trimethylbutanamide

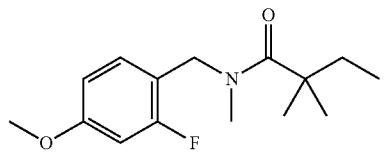 [SMILES: CCC(C)(C)C(=O)N(C)Cc1ccc(OC)cc1F]

The titled compound 16 was prepared in 57% yield from 2-fluoro-4-methoxybenzaldehyde (208 mg), methanamine hydrochloride (202 mg) and 2,2-dimethylbutanoyl chloride (275 mg) according to the procedure outlined for compound 13. $^1$H NMR (CDCl$_3$, 400 M Hz): δ7.20 (t, 1H, J=8.8 Hz), 6.57-6.67 (m, 2H), 4.59 (s, 2H), 3.78 (s, 3H), 3.01 (s, 3H), 1.65 (q, 2H, J=7.6 Hz), 1.26 (s, 6H), 0.86 (t, 3H, J=7.6 Hz). LC-MS (ESI)[M+H]+ calcd for: $C_{15}H_{22}FNO_2$, 268.2. found, 268.4.

Compound 29: Preparation of N-(2,4-difluorobenzyl)-N-ethyl-2,2-dimethylbutanamide

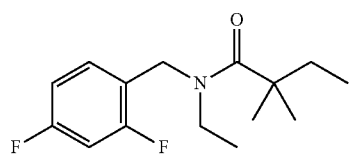 [SMILES: CCN(Cc1ccc(F)cc1F)C(=O)C(C)(C)CC]

The titled compound 29 was prepared in 57% yield from 2,4-difluorobenzaldehyde (284 mg), ethylamine hydrochloride (248 mg) and 2,2-dimethylbutanoyl chloride (275 mg) according to the procedure outlined for compound 13. $^1$H NMR (CDCl$_3$, 400 M Hz): δ7.22-7.26 (m, 1H), 6.74-6.83 (m, 2H), 4.59 (s, 2H), 3.41-3.42 (m, 2H), 1.63 (q, 2H, J=7.6 Hz), 1.23 (s, 6H), 1.15 (t, 3H, J=7.6 Hz), 0.85 (t, 3H, J=7.6 Hz). LC-MS (ESI) [M+H]+ calcd for: $C_{15}H_{21}F_2NO$, 270.2. found, 270.4.

Compound 30

Preparation of N,2,2-trimethyl-N-(3-nitro-4-(piperidin-1-yl)benzyl)butanamide

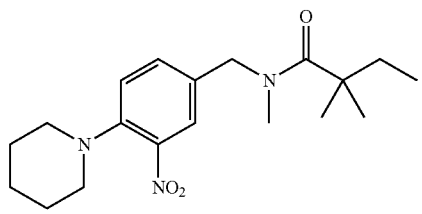 [SMILES: CCC(C)(C)C(=O)N(C)Cc1ccc(N2CCCCC2)c([N+](=O)[O-])c1]

The titled compound 30 was prepared in 66% yield from 3-nitro-4-(piperidin-1-yl)benzaldehyde (234 mg), methanamine hydrochloride (101 mg) and 2,2-dimethylbutanoyl chloride (193 mg) according to the procedure outlined for compound 13. $^1$H NMR (CDCl$_3$, 400 M Hz): δ7.61 (d, 1H, J=2.4 Hz), 7.35 (dd, 1H, J=8.4, 2.4 Hz), 7.16 (d, 1H, J=8.4 Hz), 4.54 (s, 2H), 3.03-3.06 (m, 7H), 1.73-1.77 (m, 4H), 1.68 (q, 2H, J=7.6 Hz), 1.57-1.62 (m, 2H), 1.28 (s, 6H), 0.89 (t, 3H, J=7.6 Hz). LC-MS (ESI) [M+H]+ calcd for: $C_{19}H_{29}N_3O_3$, 348.2. found 348.4.

Compound 31: Preparation of N-(2,3-dimethylbenzyl)-N,2,2-trimethylbutanamide

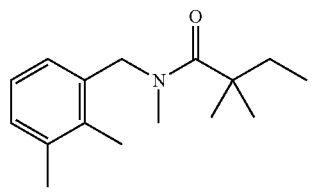 [SMILES: CCC(C)(C)C(=O)N(C)Cc1cccc(C)c1C]

The titled compound 31 was prepared in 76% yield from 2,3-dimethylbenzaldehyde (134 mg), methanamine hydrochloride (101 mg) and 2,2-dimethylbutanoyl chloride (134 mg) according to the procedure outlined for compound 13. $^1$H NMR (CDCl$_3$, 400 M Hz): δ7.05-7.09 (m, 2H), 6.93-6.95 (m, 1H), 4.65 (s, 2H), 2.97 (s, 3H), 2.29 (s, 3H), 2.16 (s, 3H), 1.69 (q, 2H, J=7.6 Hz), 1.28 (s, 6H), 0.92 (t, 3H, J=7.6 Hz). LC-MS (ESI) [M+H]+ calcd for: $C_{16}H_{25}NO$, 248.2. found 248.4.

Compound 32: Preparation of N-(3,5-dimethylbenzyl)-N,2,2-trimethylbutanamide

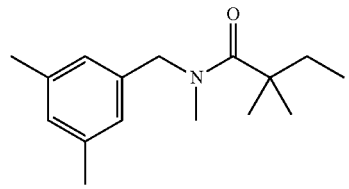 [SMILES: CCC(C)(C)C(=O)N(C)Cc1cc(C)cc(C)c1]

The titled compound 32 was prepared in 76% yield from 3,5-dimethylbenzaldehyde (134 mg), methanamine hydrochloride (101 mg) and 2,2-dimethylbutanoyl chloride (134 mg) according to the procedure outlined for compound 13. $^1$H NMR (CDCl$_3$, 400 M Hz): δ6.89 (s, 1H), 6.82 (s, 2H), 4.57 (s, 2H), 2.96 (s, 3H), 2.29 (s, 6H), 1.69 (q, 2H, J=7.6 Hz), 1.29 (s, 6H), 0.91 (t, 3H, J=7.6 Hz). LC-MS (ESI) [M+H]+ calcd for: $C_{16}H_{25}NO$, 248.2. found 248.4.

Compound 33: Preparation of N-(2-fluoro-3-(trifluoromethoxy)benzyl)-N,2,2-trimethylbutanamide

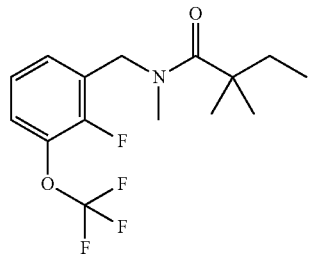 [SMILES: CCC(C)(C)C(=O)N(C)Cc1cccc(OC(F)(F)F)c1F]

The titled compound 33 was prepared in 76% yield from 2-fluoro-3-(trifluoromethoxy)benzaldehyde (192 mg), methanamine hydrochloride (101 mg) and 2,2-dimethylbutanoyl chloride (134 mg) according to the procedure outlined for compound 13. $^1$HNMR (CDCl$_3$, 400 M Hz): δ7.51 (t, 2H, J=7.2 Hz), 7.20 (t, 1H, J=7.6 Hz), 4.68 (s, 2H), 3.11 (s, 3H), 1.68 (q, 2H, J=7.6 Hz), 1.27 (s, 6H), 0.86 (t, 3H, J=7.6 Hz). LC-MS (ESI) [M+H]$^+$ calcd for C$_{15}$H$_{19}$F$_4$NO$_2$, 322.1. found 322.3.

Compound 34: Preparation of N,2,2-trimethyl-N-(pyridin-4-ylmethyl)butanamide

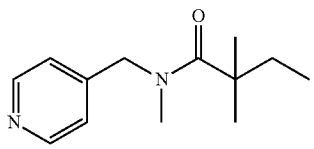 [SMILES: CCC(C)(C)C(=O)N(C)Cc1ccncc1]

The titled compound 34 was prepared in 86% yield from isonicotinaldehyde (214 mg), methanamine hydrochloride (202 mg) and 2,2-dimethylbutanoyl chloride (289 mg) according to the procedure outlined for compound 13. $^1$HNMR (CDCl$_3$, 400 M Hz): δ 8.55 (brs, 2H), 7.13 (d, 2H, J=5.6 Hz), 4.59 (s, 2H), 3.05 (s, 3H), 1.69 (q, 2H, J=7.6 Hz), 1.28 (s, 6H), 0.89 (t, 3H, J=7.6 Hz). LC-MS (ESI) [M+H]$^+$ calcd for C$_{13}$H$_{20}$N$_2$O, 221.2. found, 221.4.

Compound 35: Preparation of N,2,2-trimethyl-N-(pyridin-3-ylmethyl)butanamide

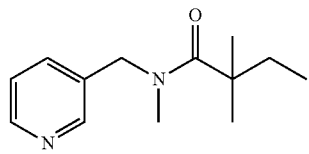 [SMILES: CCC(C)(C)C(=O)N(C)Cc1cccnc1]

The titled compound 35 was prepared in 86% yield from nicotinaldehyde (214 mg), methanamine hydrochloride (202 mg) and 2,2-dimethylbutanoyl chloride (289 mg) according to the procedure outlined for compound 13. $^1$HNMR (CDCl$_3$, 400 M Hz): δ8.48-8.51 (m, 2H), 7.58-7.61 (m, 1H), 7.24-7.27 (m, 1H), 4.59 (s, 2H), 3.03 (s, 3H), 1.66 (q, 2H, J=7.6 Hz), 1.27 (s, 6H), 0.86 (t, 3H, J=7.6 Hz). LC-MS (ESI) [M+H]$^+$ calcd for C$_{13}$H$_{20}$N$_2$O, 221.2. found, 221.4.

Compound 36: Preparation of N-((3-fluoropyridin-4-yl)methyl)-N,2,2-trimethylbutanamide

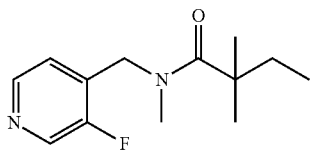 [SMILES: CCC(C)(C)C(=O)N(C)Cc1ccncc1F]

The titled compound 36 was prepared in 78% yield from 3-fluoroisonicotinaldehyde (125 mg), methanamine hydrochloride (101 mg) and 2,2-dimethylbutanoyl chloride (134 mg) according to the procedure outlined for compound 13. $^1$HNMR (CDCl$_3$, 400 M Hz): δ8.41 (d, 1H, J=1.6 Hz), 8.35 (d, 1H, J=4.8 Hz), 7.18 (dd, 1H, J=6.0, 5.2 Hz), 4.65 (s, 2H), 3.12 (s, 3H), 1.68 (q, 2H, J=7.6 Hz), 1.27 (s, 6H), 0.87 (t, 3H, J=7.6 Hz). LC-MS (ESI) [M+H]$^+$ calcd for C$_{13}$H$_{19}$FN$_2$O, 239.1. found 239.3.

Compound 37: Preparation of N-((2-methoxypyridin-3-yl)methyl)-N,2,2-trimethylbutanamide

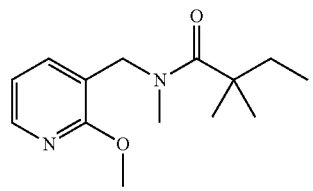 [SMILES: CCC(C)(C)C(=O)N(C)Cc1cccnc1OC]

The titled compound 37 was prepared in 72% yield from 2-methoxynicotinaldehyde (137 mg), methanamine hydrochloride (101 mg) and 2,2-dimethylbutanoyl chloride (160 mg) according to the procedure outlined for compound 13. $^1$HNMR (CDCl$_3$, 400 M Hz): δ8.06 (dd, 1H, J=5.2, 2.0 Hz), 7.40 (d, 1H, J=7.2 Hz), 6.86 (dd, 1H, J=7.2, 5.2 Hz), 4.56 (s, 2H), 3.97 (S, 3H), 3.05 (s, 3H), 1.67 (q, 2H, J=7.6 Hz), 1.25 (s, 6H), 0.87 (t, 3H, J=7.6 Hz). LC-MS (ESI) [M+H]$^+$ calcd for C$_{14}$H$_{22}$N$_2$O$_2$, 251.2. found 251.4.

Compound 38: Preparation of N-((6-methoxypyridin-3-yl)methyl)-N,2,2-trimethylbutanamide

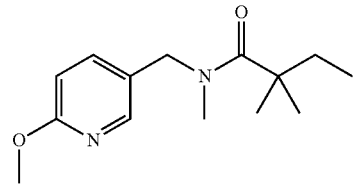 [SMILES: CCC(C)(C)C(=O)N(C)Cc1ccc(OC)nc1]

The titled compound 38 was prepared in 72% yield from 6-methoxynicotinaldehyde (137 mg), methanamine hydrochloride (101 mg) and 2,2-dimethylbutanoyl chloride (160 mg) according to the procedure outlined for compound 13. $^1$HNMR (CDCl$_3$, 400 M Hz): δ 8.01-8.02 (m, 1H), 7.53 (d, 1H, J=8.4), 6.71 (d, 1H, J=8.4), 4.51 (s, 2H), 3.92 (s, 3H), 3.00 (s, 3H), 1.66 (q, 2H, J=7.6 Hz), 1.26 (s, 6H), 0.85 (t, 3H, J=7.6 Hz). LC-MS (ESI) [M+H]$^+$ calcd for C$_{14}$H$_{22}$N$_2$O$_2$, 251.2. found 251.4.

Compound 39: Preparation of N-(cyclohexylmethyl)-N,2,2-trimethylbutanamide

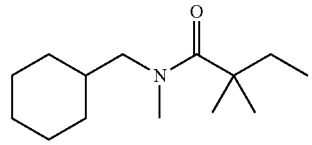 [SMILES: CCC(C)(C)C(=O)N(C)CC1CCCCC1]

The titled compound 39 was prepared in 62% yield from cyclohexanecarbaldehyde (112 mg), methanamine hydrochloride (101 mg) and 2,2-dimethylbutanoyl chloride (160 mg) according to the procedure outlined for compound 13. $^1$HNMR (CDCl$_3$, 400 MHz): δδ3.16 (d, 2H, J=6.8 Hz), 3.07 (s, 3H), 1.92 (m, 1H), 1.63-1.73 (m, 8H), 1.24 (s, 6H), 1.08-1.19 (m, 4H), 0.87 (t, 3H, J=7.6 Hz). LC-MS (ESI) [M+H]$^+$ calcd for C$_{14}$H$_{27}$NO, 226.2. found 226.4.

Compound 40: Preparation of N,2,2-trimethyl-N-(thiophen-2-ylmethyl)butanamide

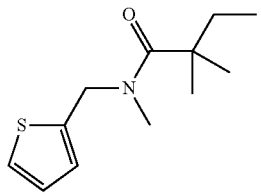

The titled compound 40 was prepared in 62% yield from thiophene-2-carbaldehyde (224 mg), methanamine hydrochloride (202 mg) and 2,2-dimethylbutanoyl chloride (119 mg) according to the procedure outlined for compound 13. $^1$HNMR (CDCl$_3$, 400 MHz): δ7.21 (dd, 1H, J=4.8, 1.6 Hz), 6.92-6.95 (m, 2H), 4.71 (s, 2H), 3.05 (s, 3H), 1.66 (q, 2H, J=7.6 Hz), 1.27 (s, 6H), 0.86 (t, 3H, J=7.6 Hz). LC-MS (ESI) [M+H]$^+$ calcd for C$_{12}$H$_{19}$NOS, 226.1. found 226.4.

Compound 41: Preparation of N,2,2-trimethyl-N-((3-methylthiophen-2-yl)methyl)butanamide

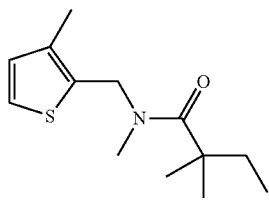 [SMILES: CCC(C)(C)C(=O)N(C)Cc1sccc1C]

The titled compound 41 was prepared in 42% yield from 3-methylthiophene-2-carbaldehyde (200 mg), methanamine hydrochloride (161 mg) and 2,2-dimethylbutanoylchloride (218 mg) according to the procedure outlined for compound 13. $^1$HNMR (CDCl$_3$, 400 MHz): δ7.11 (d, 1H, J=5.2 Hz), 6.78 (d, 1H, J=5.2 Hz), 4.68 (s, 2H), 3.03 (s, 3H), 2.23 (s, 3H), 1.67 (q, 2H, J=7.6 Hz), 1.27 (s, 6H), 0.89 (t, 3H, J=7.6 Hz). LC-MS (ESI) [M+H]$^+$ calcd for C$_{13}$H$_{21}$NOS, 234.1. found 234.4.

Compound 42: Preparation of N,2,2-trimethyl-N-((5-methylthiophen-2-yl)methyl)butanamide

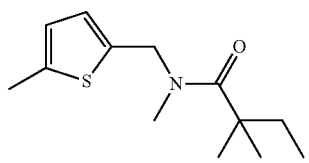 [SMILES: CCC(C)(C)C(=O)N(C)Cc1ccc(C)s1]

The titled compound 42 was prepared in 42% yield from 5-methylthiophene-2-carbaldehyde (200 mg), methanamine hydrochloride (161 mg) and 2,2-dimethylbutanoylchloride (218 mg) according to the procedure outlined for compound 13. $^1$HNMR (CDCl$_3$, 400 MHz): δ6.72 (d, 1H, J=3.2 Hz), 6.56-6.57 (m, 1H), 4.62 (s, 2H), 3.03 (s, 3H), 2.43 (d, 3H, J=1.2 Hz), 1.661 (q, 2H, J=7.6 Hz), 1.269 (s, 6H), 0.877 (t, 3H, J=7.6 Hz). LC-MS (ESI) [M+H]$^+$ calcd for C$_{13}$H$_{21}$NOS, 234.1. found 234.4.

Compound 43: Preparation of N-(furan-2-ylmethyl)-N,2,2-trimethylbutanamide

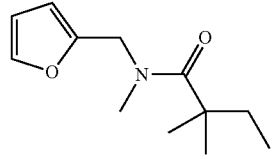

The titled compound 43 was prepared in 22% yield from furan-2-carbaldehyde (500 mg), methanamine hydrochloride (527 mg) and 2,2-dimethylbutanoylchloride (714 mg) according to the procedure outlined for compound 13. $^1$HNMR (CDCl$_3$, 400 MHz): 7.34-7.35 (m, 1H), 6.31-6.33 (m, 1H), 6.21-6.22 (m, 1H), 4.57 (s, 2H), 3.06 (s, 3H), 1.63 (q, 2H, J=7.6 Hz), 1.27 (s, 6H), 0.85 (t, 3H, J=7.6 Hz) LC-MS (ESI) [M+H]$^+$ calcd for C$_{12}$H$_{19}$NO$_2$, 210.1. found 210.3.

Compound 44: Preparation of N,2,2-trimethyl-N-((2-methylthiazol-5-yl)methyl)butanamide

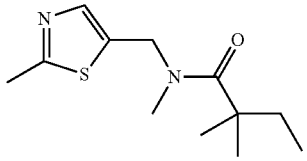 [SMILES: CCC(C)(C)C(=O)N(C)Cc1cnc(C)s1]

The titled compound 44 was prepared in 23% yield from 2-methylthiazole-5-carbaldehyde (60 mg), methanamine hydrochloride (48 mg) and 2,2-dimethylbutanoylchloride (74 mg) according to the procedure outlined for compound 13. $^1$HNMR (CDCl$_3$, 400 MHz): δ7.50 (s, 1H), 4.59 (s, 2H), 3.07 (s, 3H), 2.67 (s, 3H), 1.64 (q, 2H, J=7.6 Hz), 1.25 (s, 6H), 0.84 (t, 3H, J=7.6 Hz). LC-MS (ESI) [M+H]$^+$ calcd for C$_{12}$H$_{20}$N$_2$OS, 241.1. found 241.4.

Compound 45: Preparation of N,2,2-trimethyl-N-((1-methyl-1H-pyrazol-3-yl)methyl)butanamide

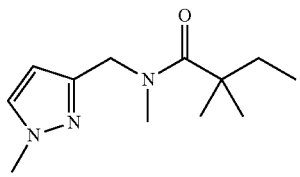 [SMILES: CCC(C)(C)C(=O)N(C)Cc1ccn(C)n1]

The titled compound 45 was prepared in 23% yield from N,1-dimethyl-1H-pyrazol-3-amine (30 mg), and 2,2-dimethylbutanoylchloride (48 mg) according to the procedure outlined for compound 13. ¹HNMR (CDCl₃, 400 MHz): δ7.26 (d, 1H, J=4.0 Hz), 6.12 (d, 1H, J=4.0 Hz), 4.57 (s, 2H), 3.85 (s, 3H), 3.01 (s, 3H), 1.65 (q, 2H, J=7.6 Hz), 1.26 (s, 6H), 0.85 (t, 3H, J=7.6 Hz). LC-MS (ESI) [M+H]⁺ calcd for $C_{12}H_{21}N_3O$, 224.2. found 224.4.

Compound 46: Preparation of N,2,2-trimethyl-N-(naphthalen-2-ylmethyl)butanamide

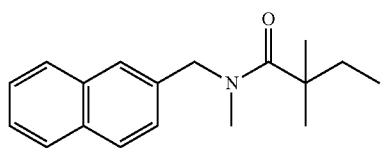 [SMILES: CCC(C)(C)C(=O)N(C)Cc1ccc2ccccc2c1]

The titled compound 46 was prepared in 74% yield from 2-naphthaldehyde (312 mg) methanamine hydrochloride (202 mg) and 2,2-dimethylbutanoylchloride (275 mg) according to the procedure outlined for compound 13
1. ¹HNMR (CDCl₃, 400 MHz): δ7.80 (m, 3H), 7.63 (m, 1H), 7.46 (m, 3H), 4.78 (s, 2H), 3.00 (s, 3H), 1.70 (q, 2H, J=7.6 Hz)), 1.30 (s, 6H), 0.93 (t, 3H, J=7.6 Hz). LC-MS (ESI)$^{[M+H]+}$ calcd for $C_{18}H_{23}NO$, 270.2. found 270.4.

Compound 47: Preparation of N,2,2-trimethyl-N-(quinolin-3-ylmethyl)butanamide

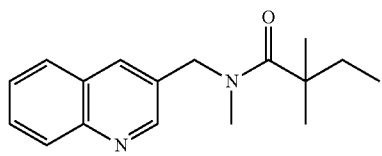 [SMILES: CCC(C)(C)C(=O)N(C)Cc1cnc2ccccc2c1]

The titled compound 47 was prepared in 60% yield from quinoline-3-carbaldehyde (157 mg), methanamine hydrochloride 101 mg) and 2,2-dimethylbutanoylchloride (175 mg) according to the procedure outlined for compound 13. ¹HNMR (CDCl₃, 400 MHz): δ8.85 (d, 1H, J=4.4 Hz), 8.13 (d, 1H, J=8.4 Hz), 7.97 (d, 1H, J=8.4 Hz), 7.68-7.73 (m, 1H), 7.53-7.57 (m, 1H), 7.155 (d, 1H, J=4.4 Hz), 5.10 (s, 2H), 3.07 (s, 3H), 1.70 (q, 2H, J=7.6 Hz), 1.29 (s, 6H), 0.91 (t, 3H, J=7.6 Hz). LC-MS (ESI) [M+H]⁺ calcd for $C_{17}H_{22}N_2O$, 271.2. found 271.4.

Compound 48: Preparation of N,2,2-trimethyl-N-(2,4,6-trifluorobenzyl)butanamide

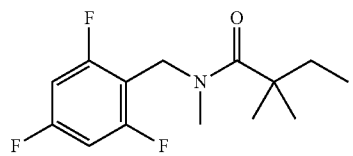 [SMILES: CCC(C)(C)C(=O)N(C)Cc1c(F)cc(F)cc1F]

The titled compound 48 was prepared in 63% yield from 2,4,6-trifluorobenzaldehydhyde (320 mg), methanamine hydrochloride (202 mg) and 2,2-dimethylbutanoylchloride (275 mg) according to the procedure outlined for compound 13. ¹HNMR (CDCl₃, 400 MHz): δ6.61-6.69 (m, 2H), 4.64 (s, 2H), 3.06 (s, 3H), 1.64 (q, 2H, J=7.6 Hz), 1.24 (s, 6H), 0.82 (t, 3H, J=7.6 Hz). LC-MS (ESI) [M⁺H]⁺ calcd for $C_{14}H_{18}F_3NO$, 274.1. found 274.3.

Compound 49: Preparation of N,2,2-trimethyl-N-(2,3,4-trifluorobenzyl)butanamide

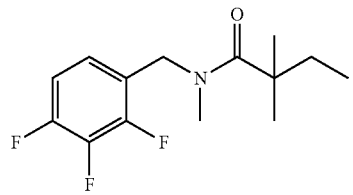 [SMILES: CCC(C)(C)C(=O)N(C)Cc1ccc(F)c(F)c1F]

The titled compound 49 was prepared in 66% yield from 2,3,4-trifluorobenzaldehyde (160 mg), methanamine hydrochloride (101 mg) and 2,2-dimethylbutanoylchloride (175 mg) according to the procedure outlined for compound 13. ¹HNMR (CDCl₃, 400 MHz): δ7.03-7.05 (m, 1H), 6.88-6.95 (m, 1H), 4.61 (s, 2H), 3.09 (s, 3H), 1.66 (q, 2H, J=7.6 Hz), 1.26 (s, 6H), 0.84 (t, 3H, J=7.6 Hz). LC-MS (ESI) [M+H]⁺ calcd for $C_{14}H_{18}F_3NO$, 274.1. found 274.3.

Compound 50: Preparation of N-(2,6-difluoro-3-methylbenzyl)-N,2,2-trimethylbutanamide

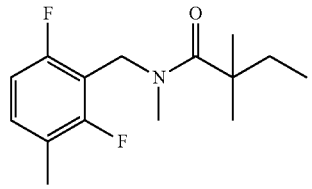 [SMILES: CCC(C)(C)C(=O)N(C)Cc1c(F)ccc(C)c1F]

The titled compound 50 was prepared in 66% yield from 2,6-difluoro-3-methylbenzaldehyde (156 mg), methanamine hydrochloride (101 mg) and 2,2-dimethylbutanoylchloride (140 mg) according to the procedure outlined for compound 13. ¹HNMR (CDCl₃, 400 MHz): δ7.06 (q, 1H, J=8.4 Hz), 6.77 (t, 1H, J=8.8 Hz), 4.71 (s, 2H), 3.02 (s, 3H), 2.22 (s, 3H), 1.66 (q, 2H, J=7.6 Hz), 1.26 (s, 6H), 0.85 (t, 3H, J=7.6 Hz). LC-MS (ESI) [M+H] calcd for $C_{15}H_{21}F_2NO$, 270.2. found 270.4.

Compound 51: Preparation of N,2,2-trimethyl-N-(2,3,5,6-tetrafluorobenzyl)butanamide

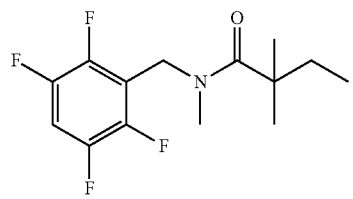

The titled compound 51 was prepared in 66% yield from 2,3,5,6-tetrafluorobenzaldehyde (178 mg), methanamine hydrochloride (101 mg) and 2,2-dimethylbutanoylchloride (140 mg) according to the procedure outlined for compound 13. ¹HNMR (CDCl₃, 400 MHz): δ6.95-7.03 (m, 1H) 4.70 (s, 2H), 3.16 (s, 3H), 1.65 (q, 2H, J=7.6 Hz), 1.24 (s, 6H), 0.83 (t, 3H, J=7.6 Hz). LC-MS (ESI) [M+H]⁺ calcd for C₁₄H₁₇F₄NO, 292.1. found 292.4.

Compound 52: Preparation of
2,2-dimethyl-N-(1-phenylethyl)butanamide

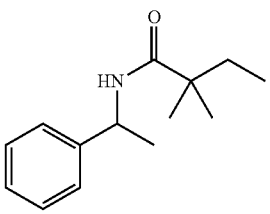 [SMILES: CCC(C)(C)C(=O)NC(C)c1ccccc1]

1-phenylethanamine (1 g, 8.26 mmoL) and Triethylamine (0.918 g, 9.09 mmoL) were dissolved in 20 mL of dry CH₂Cl₂. 2,2-dimethylbutanoyl chloride (1.223 g, 9.09 m moL) in 2 mL of CH₂Cl₂ was added slowly to the solution at 0° C. under nitrogen. The mixture was stirred at room temperature for 2 h, diluted with CH₂Cl₂ and water. The organic layers were washed with saturated NaHCO₃, brine, dried with Na₂SO₄ and concentrated. The residue was purified by chromatography to give compound 40 (1.35 g, 74.6%) as an white solid. ¹HNMR (CDCl₃, 400 MHz): δ 7.26-7.34 (m, 5H), 5.77 (brs, 1H), 5.10-5.17 (m, 1H), 1.545 (q, 2H, J=8 Hz), 1.485 (d, 3H, J=4 Hz), 1.15 (s, 6H), 0.82 (t, 3H, J=8 Hz). LC-MS (ESI) [M+H]⁺ calcd for C₁₄H₂₁NO, 220.2. found 220.4.

Compound 53: Preparation of
N,2,2-trimethyl-N-(1-phenylethyl)butanamide

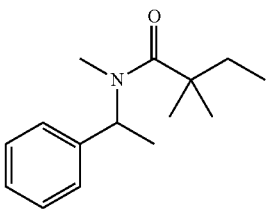 [SMILES: CCC(C)(C)C(=O)N(C)C(C)c1ccccc1]

To a solution of compound 52 (50 mg) in dry THF (1 ml) was added sodium hydride (13.7 mg) under nitrogen at 0° C. The mixture was stirred at 0° C. for 30 minutes, then iodomethane (38.9 mg) was added. The mixture was stirred at room temperature for 2 h and quenched with cold water and extracted with CH₂Cl₂. The combined organic layer were washed with H₂O, dried with Na₂SO₄ and concentrated. The residue was purified by chromatography to give compound 53 (8 mg, 15%) as a colorless oil. ¹HNMR (CDCl₃, 400 MHz): δ7.32-7.35 (m, 2H), 7.22-7.27 (m, 3H), 5.62-6.30 (m, 1H), 2.70 (s, 3H), 1.68 (q, 2H, J=7.6 Hz), 1.51 (d, 3H, J=6.0 Hz), 1.30 (s, 3H), 1.29 (s, 3H), 0.91 (t, 3H, J=7.6 Hz). LC-MS (ESI) [M+H]⁺ calcd for C₁₅H₂₃NO, 234.2. found 234.4.

Compound 54: Preparation of
2,2-dimethyl-N-(1-phenylcyclopropyl)butanamide

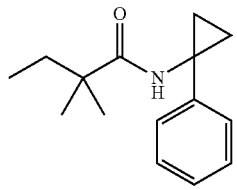 [SMILES: CCC(C)(C)C(=O)NC1(c2ccccc2)CC1]

The titled compound 54 was prepared in 96% yield from 1-phenylcyclopropanamine (106 mg) and 2,2-dimethylbutanoyl chloride (160 mg) according to the procedure outlined for compound 52. ¹HNMR (CDCl₃, 400 MHz): δ7.22-7.29 (m, 4H), 7.15-7.19 (m, 1H), 6.25 (brs, 1H), 1.54 (q, 2H, J=7.6 Hz), 1.24-1.29 (m, 2H), 1.18-1.22 (m, 2H), 1.16 (s, 6H), 0.81 (t, 3H, J=7.6 Hz). LC-MS (ESI) [M+H]⁺ calcd for C₁₅H₂₁NO, 232.1. found 232.4.

Compound 55: Preparation of
N,2,2-trimethyl-N-(1-phenylcyclopropyl)butanamide

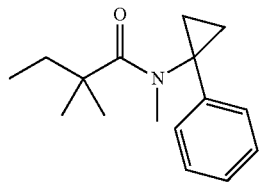 [SMILES: CCC(C)(C)C(=O)N(C)C1(c2ccccc2)CC1]

The titled compound 55 was prepared in 30% yield from compound 42 (90 mg), sodium hydride (32 mg) and iodomethane (85.2 mg) according to the procedure outlined for compound 53. ¹HNMR (CDCl₃, 400 MHz): 7.28-7.30 (m, 2H), 7.15-7.19 (m, 3H), 3.12 (s, 3H), 1.67 (q, 2H, J=7.6 Hz), 1.30-1.32 (m, 2H), 1.26 (s, 6H), 1.24-1.25 (m, 1H), 0.81 (t, 3H, J=7.6 Hz) LC-MS (ESI) [M+H]⁺ calcd for C₁₆H₂₃NO, 246.1. found, 246.4.

Compound 56: Preparation of N-(2-bromo-5-fluorobenzyl)-N,2,2-trimethylbutanamide

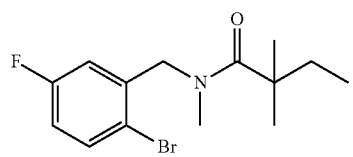 [SMILES: CCC(C)(C)C(=O)N(C)Cc1cc(F)ccc1Br]

The titled compound 56 was prepared in 56% yield from 2-bromo-5-fluorobenzaldehyde (500 mg), methanamine hydrochloride (249 mg) and 2,2-dimethylbutanoyl chloride (317 mg) according to the procedure outlined for compound 13. ¹HNMR (CDCl₃, 400 MHz): 7.48-7.52 (m, 1H), 7.04-7.10 (m, 2H), 4.80 (s, 2H), 3.15 (s, 3H), 1.71 (q, 2H, J=7.6 Hz), 1.30 (s, 6H), 0.91 (t, 3H, J=7.6 Hz) LC-MS (ESI) [M+H]⁺ calcd for C14H19BrFNO, 316.1. found, 316.1, 318.2.

Compound 57: Preparation of N-(2-cyano-5-fluorobenzyl)-N,2,2-trimethylbutanamide

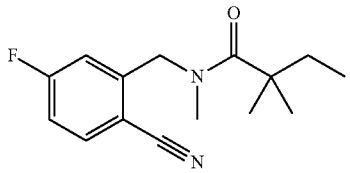 [SMILES: CCC(C)(C)C(=O)N(C)Cc1cc(F)ccc1C#N]

A mixture of compound 56 (30 mg), sodium iodide (1.4 mg) and copper(I) cyanide (22 mg) in dry DMF (1 mL) was stirred at 180° C. for 6 h. The mixture was diluted with saturated aqueous NaHCO₃ solution (2 mL) and the aqueous layer was extracted with dichloromethane (5 mL×3). The combined organic layers were washed with brine, dried with Na₂SO₄, filtered and concentrated. The residue was purified by Pre-TLC to give compound 57 (18 mg, 72%). 1H-NMR (CDCl3, 400 MHz): δ 7.64-7.67 (m, 1H), 6.83-6.88 (m, 2H), 4.65 (s, 2H), 3.09 (s, 3H), 1.71 (q, 2H, J=7.6 Hz), 1.29 (s, 6H), 0.93 (t, 3H, J=7.6 Hz) MS (ES) [M+H]$^+$ calcd for C15H19FN2O, 263.1. found, 263.3.

Compound 58: Preparation of N-benzyl-2,2-dimethylbutanamide

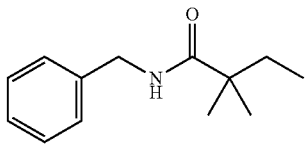

The titled compound 58 was prepared in 84% yield from phenylmethanamine (107 mg) and 3,3-dimethylbutanoyl chloride (140 mg) according to the procedure outlined for compound 52. $^1$H NMR (CDCl$_3$): δ 7.25-7.36 (m, 5H), 5.88 (br, 1H), 4.45 (d, 2H, J=8.0 Hz), 1.58 (q, 2H, J=5.6 Hz), 1.19 (s, 6H), 0.81 (t, 3H, J=5.6 Hz).

Compound 59: Preparation of N-(2-fluorobenzyl)-N,3,3-trimethylbutanamide

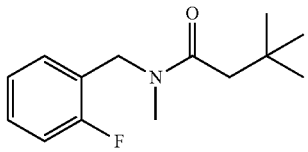 [SMILES: CN(Cc1ccccc1F)C(=O)CC(C)(C)C]

The titled compound 59 was prepared in 34% yield from 2-fluorobenzaldehyde (124 mg), methanamine hydrochloride (101 mg) and 3,3-dimethylbutanoyl chloride (140 mg) according to the procedure outlined for compound 13. $^1$HNMR (CDCl$_3$, 400 MHz): δ 7.22-7.36 (m, 2H), 7.01-7.15 (m, 2H), 4.65 (s, 2H), 2.97 (s, 3H), 2.31 (s, 2H), 1.07 (s, 9H). LC-MS (ESI) [M+H]$^+$ calcd for C$_{14}$H$_{20}$FNO, 238.2. found 238.4.

Compound 60: Preparation of N-(2-fluorobenzyl)-N-methylcyclohexanecarboxamide

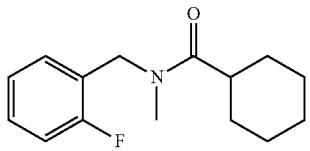 [SMILES: CN(Cc1ccccc1F)C(=O)C1CCCCC1]

The titled compound 60 was prepared in 66% yield from 2-fluorobenzaldehyde (124 mg), methanamine hydrochloride (101 mg) and cyclohexane carbonyl chloride (153 mg) according to the procedure outlined for compound 13. $^1$HNMR (CDCl$_3$, 400 MHz): 7.23-7.28 (m, 2H), 7.01-7.11 (m, 2H), 4.63 (s, 2H), 2.97 (s, 3H), 2.51-2.56 (m, 1H), 1.52-1.79 (m, 7H), 1.24-1.31 (m, 3H). LC-MS (ESI) [M+H]$^+$ calcd for C$_{15}$H$_{20}$FNO, 250.2. found, 250.4.

Compound 61: Preparation of N-(2-fluorobenzyl)-N-methylbenzamide

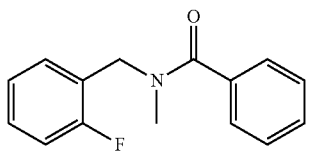 [SMILES: CN(Cc1ccccc1F)C(=O)c1ccccc1]

The titled compound 61 was prepared in 56% yield from 2-fluorobenzaldehyde (124 mg), methanamine hydrochloride (101 mg) and benzoyl chloride (147 mg) according to the procedure outlined for compound 1. $^1$HNMR (DMSO, 400 MHz): δ 7.20-7.42 (m, 9H), 4.70 (s, 1H), 4.50 (s, 1H), 2.84 (s, 3H). LC-MS (ESI) [M+H]$^+$ calcd for C$_{15}$H$_{14}$FNO, 244.1. found 244.3.

Compound 62: Preparation of N-(2-fluorobenzyl)-N-methylcyclopropanecarboxamide

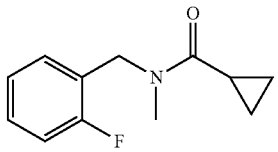

The titled compound 50 was prepared in 54% yield from 2-fluorobenzaldehyde (124 mg), methanamine hydrochloride (101 mg) and cyclopropanecarbonyl chloride (147 mg) according to the procedure outlined for compound 13. $^1$HNMR (CDCl$_3$, 400 MHz): δ 7.25-7.27 (m, 2H), 7.03-7.14 (m, 2H), 4.76 (s, 2H), 3.11 (s, 3H), 1.69-1.83 (m, 1H), 1.01-1.05 (m, 2H), 0.69-0.86 (m, 2H). LC-MS (ESI) [M+H]$^+$ calcd for C$_{12}$H$_{14}$FNO, 208.1. found, 208.3.

Compound 63: Preparation of N-(3-fluorobenzyl)-N-(3-methoxypropyl)-2,2-dimethylbutanamide

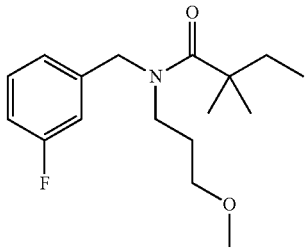 [SMILES: CCC(C)(C)C(=O)N(CCCOC)Cc1cccc(F)c1]

A mixture of (2-fluorophenyl)methanamine (125 mg), potassium carbonate (414 mg) and 1-chloro-3-methoxypropane (108 mg) in DMF (5 ml) was stirred at 100° C. for 16 h. The mixture was diluted with $CH_2Cl_2$, washed with $H_2O$, dried with $Na_2SO_4$. After removal of the solvent to give the crude N-(3-fluorobenzyl)-3-methoxypropan-1-amine (200 mg). The resulting compound was dissolve in dry THF (10 ml), and DIPEA (193 mg) was added. The mixture was cooled to 0° C., 2,2-dimethylbutanoylchloride (201 mg) was added and stirred for 4 h at room temperature. The mixture was quenched with water and extracted with EtOAc. The combined organic layer were washed with brine and dried over $Na_2SO_4$. After removal of the solvent, the residue was purified by silica gel chromatography to afford the compound 63 (177 mg, 60%).

$^1$HNMR (CDCl$_3$, 400 MHz): δ7.27-7.31 (m, 1H), 6.88-6.98 (m, 3H), 4.66 (s, 2H), 3.41 (m, 2H), 3.36 (t, 2H, J=6.0 Hz), 3.29 (s, 3H), 1.84-1.86 (m, 2H), 1.67 (q, 2H, J=7.6 Hz), 1.28 (s, 6H), 0.90 (t, 3H, J=7.6 Hz). LC-MS (ESI) [M+H]$^+$ calcd for $C_{17}H_{26}FNO_2$, 296.2. found 296.4.

Compound 64: Preparation of N-(cyclopropylmethyl)-N-(3-fluorobenzyl)-2,2-dimethylbutanamide

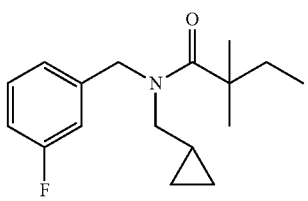 [SMILES: CCC(C)(C)C(=O)N(Cc1cccc(F)c1)CC1CC1]

The titled compound 64 was prepared in 54% yield from (2-fluorophenyl)methanamine (125 mg), (bromomethyl)cyclopropane (135 mg) and 2,2-dimethylbutanoylchloride (201 mg) according to the procedure outlined for compound 63. $^1$HNMR (CDCl$_3$, 400 MHz): δ 7.24-7.30 (m, 1H), 6.88-6.98 (m, 3H), 4.81 (s, 2H), 3.24 (d, 2H, J=6.4 Hz), 1.70 (q, 2H, J=7.6 Hz), 1.29 (s, 6H), 0.94 (t, 3H, J=7.6 Hz), 0.87-0.90 (m, 1H), 0.51 (m, 2H), 0.13 (m, 2H). LC-MS (ESI) [M+H]$^+$ calcd for $C_{17}H_{24}FNO$, 278.2. found 278.3.

Compound 65: Preparation of N,1-dimethyl-N-(2,3,5-trifluorobenzyl)cyclohexanecarboxamide

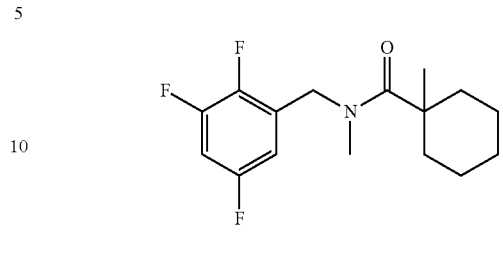

N-methyl-1-(2,3,5-trifluorophenyl)methanamine (37 mg, 0.211 mmol), which was prepared from 2,3,5-trifluorobenzaldehyde and methanamine hydrochloride according to the procedure outlined for compound 13, and 1-methylcyclohexanecarboxylic acid (30 mg, 0.211 mmoL) were dissolved in dry DMF (1 ml), 2-(7-Aza-1H-benzotriazole-1-yl)-1,1,3,3-tetramethyluronium hexafluorophosphate (119.7 mg, 0.315 mmoL) and N,N-Diisopropylethylamine (54.2 mg, 0.42 mmoL) were added to the solution. The mixture was stirred at room temperature for 16 h. The solvent was removed under reduced pressure and the residue was purified by column chromatography to give 12 mg of desired compound 65 as colorless oil (yield=19.5%)$^1$H NMR: (CDCl$_3$, 400 M Hz) δ (ppm) 6.80-6.82 (m, 1H), 6.72-6.76 (m, 1H), 4.65 (s, 2H), 3.10 (s, 3H), 2.06-2.11 (m, 2H), 1.36-1.54 (m, 8H), 1.27 (s, 3H). LC-MS (ESI) [M+H]$^+$ calcd for $C_{16}H_{20}F_3NO$, 300.1. found 300.3.

Compound 66: Preparation of 3-hydroxy-N,2,2-trimethyl-N-(3,4,5-trifluorobenzyl)propanamide

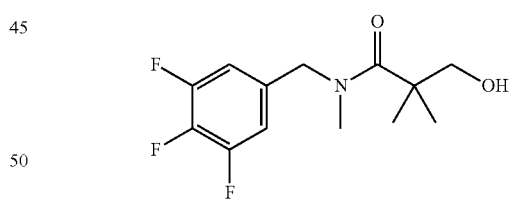

The titled compound 66 was prepared in 34% yield from N-methyl-1-(3,4,5-trifluorophenyl)methanamine (447 mg), which was prepared from 2,3,5-trifluorobenzaldehyde and methanamine hydrochloride according to the procedure outlined for compound 13, and 3-hydroxy-2,2-dimethylpropanoic acid (300 mg) and according to the procedure outlined for compound 65. $^1$H NMR: (CDCl$_3$, 400 M Hz): δ 6.82 (m, 2H), 4.52 (s, 2H), 3.57 (s, 2H), 3.06 (s, 3H), 1.32 (s, 6H). LC-MS (ESI) [M+H]$^+$ calcd for $C_{13}H_{16}F_3NO_2$, 276.1. found 276.3.

Compound 67: Preparation of 2-methoxy-N,2-dimethyl-N-(2,3,5-trifluorobenzyl)propanamide

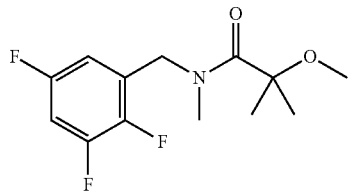 [SMILES: COC(C)(C)C(=O)N(C)Cc1cc(F)cc(F)c1F]

The titled compound 55 was prepared in 14% yield from 2-methoxy-2-methylpropa-noicacid (300 mg) and N-methyl-1-(2,3,5-trifluorophenyl)methanamine (447 mg) according to the procedure outlined for compound 65. $^1$H NMR: (CDCl$_3$, 400 M Hz): δ7.01-7.04 (m, 2H), 4.64 (s, 2H), 3.42 (s, 3H), 3.37 (s, 3H), 1.62 (s, 6H). LC-MS (ESI) [M+H]$^+$ calcd for C$_{13}$H$_{16}$F$_3$NO$_2$, 276.1. found 276.3.

Compound 68: Preparation of N,2,2-trimethyl-3-(methylamino)-N-(3,4,5-trifluorobenzyl) propanamide

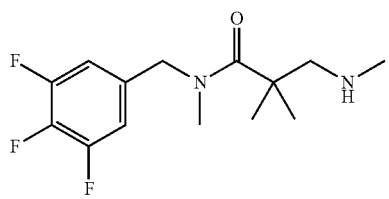 [SMILES: CNCC(C)(C)C(=O)N(C)Cc1cc(F)c(F)c(F)c1]

A mixture of 3-chloro-N,2,2-trimethyl-N-(3,4,5-trifluorobenzyl)propanamide (60 mg) methanamine hydrochloride (27 mg), potassium carbonate (138 mg) and potassium iodide (33.2 mg) in methyl cyanide (5 mL) was refluxed for overnight. The mixture was diluted with water (2 mL), The aqueous layer was extracted with dichloromethane (5 mL×3). The organic layers were combined and concentrated. The residue was purified by Pre-HPLC to give 2 mg of compound 68 as TFA salt. $^1$H NMR: (CDCl$_3$, 400 M Hz) δ 6.80-6.88 (m, 2H), 4.51 (s, 2H), 4.22 (brs, 1H), 3.00-3.16 (m, 5H), 2.82 (s, 3H), 1.51 (s, 6H). LC-MS (ESI) [M+H]$^+$ calcd for C$_{14}$H$_{19}$F$_3$N$_2$O, 289.2. found 289.4.

Compound 69: Preparation of N-methyl-N-(3,4,5-trifluorobenzyl)pivalamide

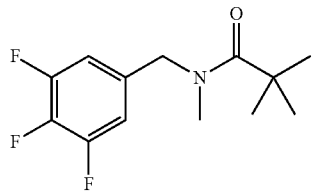 [SMILES: CN(Cc1cc(F)c(F)c(F)c1)C(=O)C(C)(C)C]

The titled compound 69 was prepared in 27% yield from pivalic acid (14.6 mg) and N-methyl-1-(3,4,5-trifluorophenyl)methanamine (25 mg) according to the procedure outlined for compound 65. $^1$H NMR: (CDCl$_3$, 400 M Hz): δ 6.79-6.86 (m, 2H), 4.52 (s, 2H), 3.05 (s, 3H), 1.33 (s, 9H). LC-MS (ESI) [M+H]$^+$ calcd for C$_{13}$H$_{16}$F$_3$NO, 260.1. found 260.3.

Compound 70: Preparation of 2,2-dimethyl-N-(2,3,5-trifluorobenzyl)butanamide

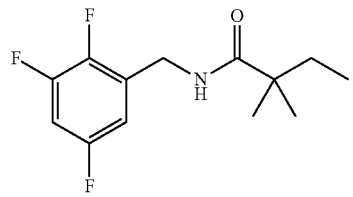

The titled compound 58 was prepared in 41.5% yield from (2,3,5-trifluorophenyl)methanamine (30 mg) and 2,2-dimethylbutanoyl chloride (27.6 mg) according to the procedure outlined for compound 52. $^1$H NMR: (CDCl$_3$, 400 M Hz): δ6.81-6.87 (m, 2H), 6.02 (brs, 1H), 4.50 (d, 1H, J=1.2 Hz), 4.48 (d, 1H, J=1.2 Hz), 1.56 (q, 2H, J=7.6 Hz), 1.18 (s, 6H), 0.82 (t, 3H, J=7.6 Hz). LC-MS (ESI) [M+H]$^+$ calcd for C$_{13}$H$_{16}$F$_3$NO, 260.1. found 260.3.

Compound 71: Preparation of 3-methoxy-N,2,2-trimethyl-N-(3,4,5-trifluorobenzyl)propanamide

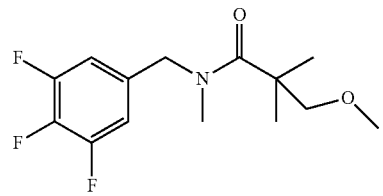 [SMILES: COCC(C)(C)C(=O)N(C)Cc1cc(F)c(F)c(F)c1]

The titled compound 71 was prepared in 13% yield from 3-methoxy-2,2-dimethylpropanoic acid (14 mg) and N-methyl-1-(3,4,5-trifluorophenyl)methanamine (447 mg) according to the procedure outlined for compound 65. $^1$H NMR: (CDCl$_3$, 400 M Hz): δ6.84-6.88 (m, 2H), 4.54 (s, 2H), 3.48 (s, 2H), 3.36 (s, 3H), 3.04 (s, 3H), 1.33 (s, 6H). LC-MS (ESI) [M+H]$^+$ calcd for C$_{14}$H$_{18}$F$_3$NO$_2$, 290.1. found, 290.4.

Compound 72: Preparation of 2-ethyl-N,2-dimethyl-N-(3,4,5-trifluorobenzyl)butanamide

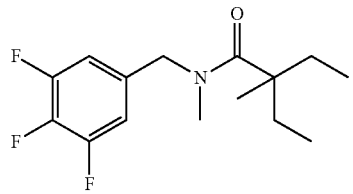 [SMILES: CCC(C)(CC)C(=O)N(C)Cc1cc(F)c(F)c(F)c1]

The titled compound 72 was prepared in 18% yield from N-methyl-1-(3,4,5-trifluorophenyl)methanamine (20 mg) and 2-ethyl-2-methylbutanoic acid (15 mg) according to the procedure outlined for compound 65. $^1$H NMR: (CDCl$_3$, 400

M Hz): δ6.87-6.91 (m, 2H), 4.50 (s, 2H), 3.05 (s, 3H), 1.77-1.84 (m, 2H), 1.47-1.56 (m, 2H), 1.23 (s, 3H), 0.87 (t, 6H, J=7.6 Hz). LC-MS (ESI) [M+H]+ calcd for $C_{15}H_{20}F_3NO$, 288.1. found 288.3.

Compound 73: Preparation of 2-ethyl-2-methyl-N-(2,3,5-trifluorobenzyl)butanamide

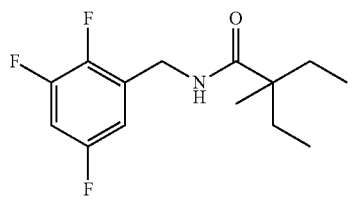

The titled compound 73 was prepared in 12% yield from (2,3,5-trifluorophenyl)methanamine (30 mg) and 2-ethyl-2-methylbutanoic acid (24.4 mg) according to the procedure outlined for compound 65. $^1$H NMR: (CDCl$_3$, 400 M Hz): δ 6.82-6.88 (m, 2H), 6.03 (brs, 1H), 4.49 (d, 2H, J=6.0 Hz), 1.61-1.69 (m, 2H), 1.39-1.48 (m, 2H), 1.12 (s, 3H), 0.80 (t, 6H, J=7.6 Hz). LC-MS (ESI) [M+H]+ calcd for $C_{14}H_{18}F_3NO$, 274.1. found 274.3.

Compound 74: Preparation of N-ethyl-N-(2,3,5-trifluorobenzyl)cyclohexanecarboxamide

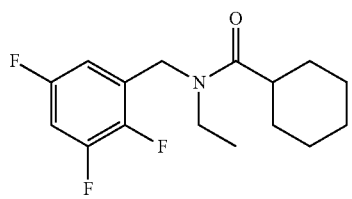 [SMILES: CCN(Cc1cc(F)cc(F)c1F)C(=O)C1CCCCC1]

The titled compound 74 was prepared in 53% yield from 2,3,5-trifluorobenzaldehyde (320 mg), ethylamine hydrochloride (244 mg) and 2,2-dimethylbutanoylchloride (275 mg) according to the procedure outlined for compound 13. $^1$HNMR (CDCl$_3$, 400 MHz): δ6.77-683 (m, 1H), 6.59-6.75 (m, 1H), 4.61 (s, 2H), 3.35 (q, 2H, J=7.2 Hz), 2.47-2.54 (m, 1H), 1.41-1.95 (m, 10H), 1.20 (t, 3H, J=7.2 Hz). LC-MS (ESI) [M+H]+ calcd for $C_{16}H_{20}F_3NO$, 300.1. found, 300.3.

Compound 75: Preparation of N,2,2-trimethyl-N-(2,3,5-trifluorobenzyl)butanamide

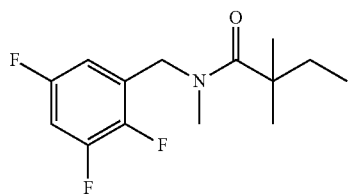

The titled compound 75 was prepared in 50% yield from 2,3,5-trifluorobenzaldehyde (320 mg), methanamine hydrochloride (202 mg) and 2,2-dimethylbutanoylchloride (275 mg) according to the procedure outlined for compound 13. $^1$HNMR (CDCl$_3$, 400 MHz): δ 6.75-6.85 (m, 2H), 4.64 (s, 2H), 3.11 (s, 3H), 1.68 (q, 2H, J=7.6 Hz), 1.28 (s, 6H), 0.88 (t, 3H, J=7.6 Hz). LC-MS (ESI) [M+H]+ calcd for $C_{14}H_{18}F_3NO$, 274.1. found 274.3.

Compound 76: Preparation of N-methyl-N-(2,3,5-trifluorobenzyl)adamantane-1-carboxamide

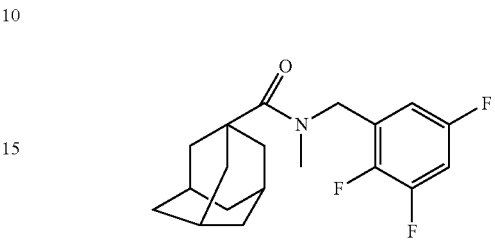

The titled compound 76 was prepared in 16% yield from 2,3,5-trifluorobenzaldehyde (50 mg), methanamine hydrochloride (29 mg) and adamantane-1-carbonyl chloride (40 mg) according to the procedure outlined for compound 13. $^1$HNMR (CDCl$_3$, 400 MHz): δ7.30-7.51 (m, 1H), 6.66-6.70 (m, 1H), 4.58 (s, 2H), 3.10 (s, 3H), 1.93-1.96 (m, 10H), 1.64-1.67 (m, 4H). LC-MS (ESI) [M+H]+ calcd for $C_{19}H_{22}F_3NO$, 338.2. found 338.4.

Compound 77: Preparation of N-(2-hydroxyethyl)-2,2-dimethyl-N-(2,3,5-trifluorobenzyl)butanamide

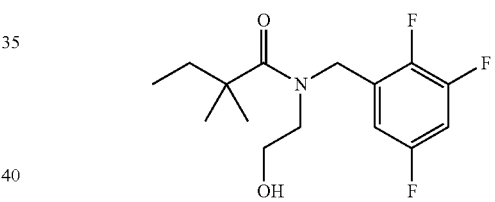

The titled compound 77 was prepared in 30% yield from 2-((2,3,5-trifluorobenzyl)amino)ethanol (50 mg) and 2,2-dimethylbutanoylchloride (33 mg) according to the procedure outlined for compound 52. $^1$HNMR (CDCl$_3$, 400 MHz): δ 6.92-6.97 (m, 1H), 6.80-6.87 (m, 1H), 4.21 (t, 2H, J=5.2 Hz), 3.92 (s, 2H), 2.89 (t, 2H, J=5.2 Hz), 1.57 (q, 2H, J=7.2 Hz), 1.16 (s, 6H), 0.83 (t, 3H, J=7.2 Hz). LC-MS (ESI) 1M+Hr calcd for $C_{15}H_{20}F_3NO_2$, 304.1. found 304.3.

Compound 78: Preparation of N,2-dimethyl-N-(2,3,5-trifluorobenzyl)propane-2-sulfinamide

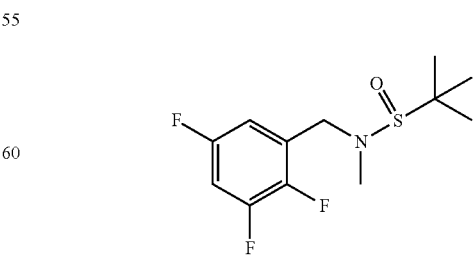

The titled compound 78 was prepared in 30% yield from N-methyl-1-(2,3,5-trifluorophenyl)methanamine (50 mg)

and 2,2-dimethylbutanoylchloride (57 mg) according to the procedure outlined for compound 52. ¹HNMR (CDCl₃, 400 MHz): δ 6.83-6.94 (m, 2H), 4.23-4.32 (m, 2H), 2.64 (s, 3H), 1.21 (s, 9H). LC-MS (ESI) [M+H]⁺ calcd for $C_{12}H_{16}F_3NOS$, 280.1. found, 280.2.

Compound 79: Preparation of N-methyl-N-(2,3,5-trifluorobenzyl)cyclohexanesulfonamide

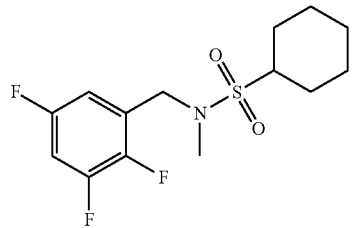 [SMILES: CN(Cc1cc(F)cc(F)c1F)S(=O)(=O)C1CCCCC1]

The titled compound 79 was prepared in 11% yield from N-methyl-1-(2,3,5-trifluorophenyl)methanamine (20 mg) and cyclohexanesulfonyl chloride (30 mg) according to the procedure outlined for compound 52. ¹HNMR (CDCl₃, 400 MHz): δ7.02-7.07 (m, 1H), 6.84-6.91 (m, 1H), 4.46 (s, 2H), 2.99-3.05 (m, 1H), 2.86 (s, 3H), 1.95-2.15 (m, 2H), 1.91-1.94 (m, 2H), 1.57-1.74 (m, 5H), 1.21-1.28 (m, 1H). LC-MS (ESI) [M+H]⁺ calcd for $C_{14}H_{18}F_3NO_2S$, 322.1. found 322.3.

Compound 80: Preparation of N,1-dimethyl-N-(2,3,5-trifluorobenzyl)cyclopropanecarboxamide

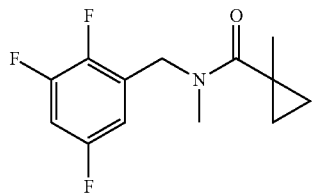 [SMILES: CN(Cc1cc(F)cc(F)c1F)C(=O)C1(C)CC1]

The titled compound 80 was prepared in 35% yield from 1-methylcyclopropanecarboxylic acid (20 mg) and N-methyl-1-(2,3,5-trifluorophenyl)methanamine (35 mg) according to the procedure outlined for compound 65. ¹H NMR: (CDCl₃, 400 M Hz): δ 6.80-6.83 (m, 2H), 4.52 (s, 2H), 3.05 (s, 3H), 1.34 (s, 3H), 0.98 (t, 2H, J=4.8 Hz), 0.63 (t, 2H, J=4.8 Hz). LC-MS (ESI) [M+H]⁺ calcd for $C_{13}H_{14}F_3NO$, 258.1. found 258.3.

Compound 81: Preparation of N,2,2,3,3-pentamethyl-N-(3,4,5-trifluorobenzyl)-cyclopronanecarboxamide

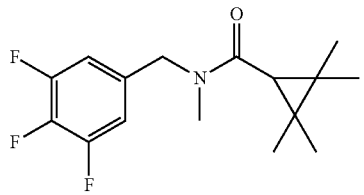 [SMILES: CN(Cc1cc(F)c(F)c(F)c1)C(=O)C1C(C)(C)C1(C)C]

The titled compound 81 was prepared in 28.5% yield from 2,2,3,3-tetramethylcyclopropanecarboxylic acid (30 mg) and N-methyl-1-(3,4,5-trifluorophenyl)methanamine (37 mg) according to the procedure outlined for compound 65. ¹H NMR: (CDCl₃, 400 M Hz): δ6.83-6.87 (m, 2H), 4.50 (s, 2H), 2.96 (s, 3H), 1.21 (s, 6H), 1.18 (s, 6H). LC-MS (ESI) [M+H]⁺ calcd for $C_{16}H_{20}F_3NO$, 300.1. found 300.3.

Compound 82: Preparation of N-methyl-1-phenyl-N-(2,3,5-trifluorobenzyl)cyclopropanecarboxamide

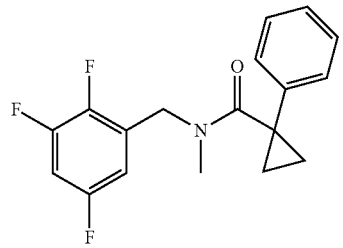

The titled compound 82 was prepared in 30% yield from phenylcyclopropanecarboxylic acid (50 mg) and N-methyl-1-(2,3,5-trifluorophenyl)methanamine (55 mg) according to the procedure outlined for compound 65. ¹H NMR: (CDCl₃, 400 M Hz): δ7.26-7.30 (m, 1H), 7.16-7.26 (m, 3H), 6.74-6.94 (m, 3H), 4.65 (s, 2H), 2.85 (s, 3H), 1.43-1.46 (m, 2H), 1.23 (m, 2H). LC-MS (ESI) [M+H]⁺ calcd for $C_{18}H_{16}F_3NO$, 320.1. found 320.3.

Compound 83: Preparation of N-methyl-N-(2,3,5-trifluorobenzyl)cyclobutanecarboxamide

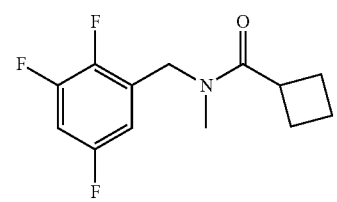 [SMILES: CN(Cc1cc(F)cc(F)c1F)C(=O)C1CCC1]

The titled compound 83 was prepared in 29.2% yield from cyclobutanecarboxylic acid (20 mg) and N-methyl-1-(2,3,5-trifluorophenyl)methanamine (35 mg) according to the procedure outlined for compound 65. ¹HNMR: (CDCl₃, 400 M Hz): δ6.76-6.86 (m, 2H), 4.61 (s, 2H), 3.29-3.33 (m, 1H), 2.89 (s, 3H), 2.32-2.41 (m, 2H), 2.17-2.22 (m, 2H), 1.86-1.99 (m, 2H). LC-MS (ESI) [M+H]⁺ calcd for $C_{13}H_{14}F_3NO$, 258.2. found 258.4.

Compound 84: Preparation of N-methyl-N-(2,3,5-trifluorobenzyl)-1-(trifluoromethyl)cyclobutanecarboxamide

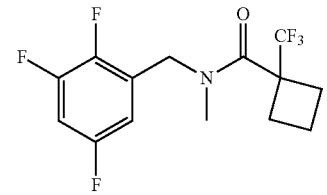 [SMILES: CN(Cc1cc(F)cc(F)c1F)C(=O)C1(C(F)(F)F)CCC1]

The titled compound 84 was prepared in 25.9% yield from 1-(trifluoromethyl)cyclobutanecarboxylic acid (30 mg) and N-methyl-1-(2,3,5-trifluorophenyl)methanamine (31 mg) according to the procedure outlined for compound 65. $^1$H NMR: (CDCl$_3$, 400 M Hz): δ 6.80-6.89 (m, 1H), 6.74-6.77 (m, 1H), 4.66 (s, 2H), 2.92 (s, 3H), 2.68-2.77 (m, 2H), 2.52-2.58 (m, 2H), 2.08-2.16 (m, 1H), 1.83-1.87 (m, 1H). LC-MS (ESI) [M+H]$^+$ calcd for C$_{14}$H$_{13}$F$_6$NO, 326.1. found 326.4.

Compound 85: Preparation of N-methyl-N-(3,4,5-trifluorobenzyl)cyclopentanecarboxamide

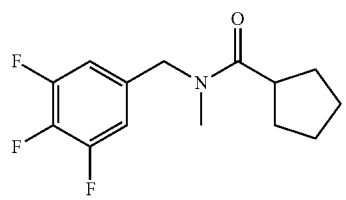 [SMILES: CN(Cc1cc(F)c(F)c(F)c1)C(=O)C1CCCC1]

The titled compound 85 was prepared in 25.2% yield from cyclopentanecarboxylic acid (30 mg) and N-methyl-1-(3,4,5-trifluorophenyl)methanamine (46 mg) according to the procedure outlined for compound 65. $^1$H NMR: (CDCl$_3$, 400 M Hz): δ 6.28-6.86 (m, 2H), 4.50 (s, 2H), 2.99 (s, 3H), 2.93-2.97 (m, 1H), 1.73-1.89 (m, 6H), 1.57-1.62 (m, 2H). LC-MS (ESI) [M+H]$^+$ calcd for C$_{14}$H$_{16}$F$_3$NO, 272.1. found 272.3.

Compound 86: Preparation of N-methyl-N-(2,3,5-trifluorobenzyl)-1-(trifluoromethyl)cyclopentanecarboxamide

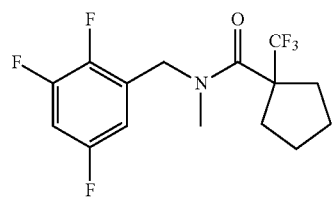 [SMILES: CN(Cc1cc(F)cc(F)c1F)C(=O)C1(C(F)(F)F)CCCC1]

The titled compound 86 was prepared in 26.9% yield from 1-(trifluoromethyl)cyclopentanecarboxylic acid (30 mg) and N-methyl-1-(2,3,5-trifluorophenyl)methanamine (29 mg) according to the procedure outlined for compound 65. $^1$H NMR: (CDCl$_3$, 400 M Hz): δ 6.79-6.85 (m, 1H), 6.65-6.69 (m, 1H), 4.65 (s, 2H), 3.07 (s, 3H), 2.38-2.44 (m, 2H), 2.15-2.21 (m, 2H), 1.59-1.74 (m, 4H). LC-MS (ESI) [M+H]$^+$ calcd for C$_{15}$H$_{15}$F$_6$NO, 340.1. found, 340.3.

Compound 87: Preparation of N-methyl-1-phenyl-N-(2,3,5-trifluorobenzyl)cyclopentanecarboxamide

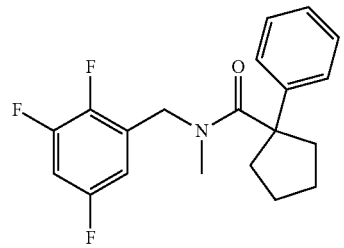 [SMILES: CN(Cc1cc(F)cc(F)c1F)C(=O)C1(c2ccccc2)CCCC1]

The titled compound 87 was prepared in 29.5% yield from 1-phenylcyclopentanecarboxylic acid (50 mg) and N-methyl-1-(2,3,5-trifluorophenyl)methanamine (47 mg) according to the procedure outlined for compound 65. $^1$H NMR: (CDCl$_3$, 400 M Hz): δ7.19-7.31 (m, 5H), 6.74-6.77 (m, 2H), 4.60 (s, 2H), 2.54 (s, 3H), 2.37-2.43 (m, 2H), 2.02-2.05 (m, 2H), 1.66-1.77 (m, 4H). LC-MS (ESI) [M+H]$^+$ calcd for C$_{20}$H$_{20}$F$_3$NO, 348.1. found 348.3.

Compound 88: Preparation of 1-ethyl-N-methyl-N-(3,4,5-trifluorobenzyl)cyclobutanecarboxamide

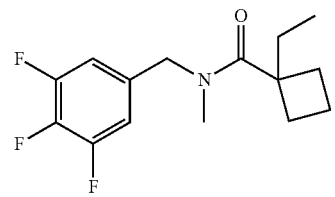 [SMILES: CCC1(C(=O)N(C)Cc2cc(F)c(F)c(F)c2)CCC1]

The titled compound 88 was prepared in 19.7% yield from 1-ethylcyclobutanecarboxylic acid (18 mg) and N-methyl-1-(3,4,5-trifluorophenyl)methanamine (25 mg) according to the procedure outlined for compound 65. $^1$H NMR: (CDCl$_3$, 400 M Hz): δ6.74-6.94 (m, 2H), 4.46 (s, 2H), 2.82 (s, 3H), 2.46-2.55 (m, 2H), 1.74-1.98 (m, 6H), 0.88 (t, 3H, J=7.6 Hz). LC-MS (ESI) [M+H]$^+$ calcd for C$_{15}$H$_{18}$F$_3$NO, 286.1. found 286.4.

Compound 89: Preparation of 1-ethyl-N-methyl-N-(3,4,5-trifluorobenzyl)cyclopentanecarboxamide

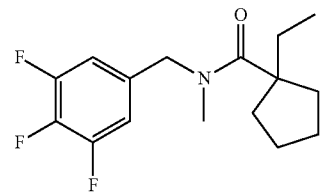 [SMILES: CCC1(C(=O)N(C)Cc2cc(F)c(F)c(F)c2)CCCC1]

The titled compound 89 was prepared in 18.7% yield from 1-ethylcyclopentanecarboxylic acid (20 mg) and N-methyl-1-(3,4,5-trifluorophenyl)methanamine (25 mg) according to the procedure outlined for compound 65. $^1$H NMR: (CDCl$_3$, 400 M Hz): δ 6.82-6.90 (m, 2H), 4.50 (s, 2H), 2.99 (s, 3H), 2.18-2.27 (m, 2H), 1.66 (q, 2H, J=7.6 Hz), 1.57-1.62 (m, 6H), 0.84 (t, 3H, J=7.6 Hz). LC-MS (ESI) [M+H]+ calcd for C$_{16}$H$_{20}$F$_3$NO, 300.2. found 300.4.

Compound 90: Preparation of N-benzyl-N,2,2-trimethylbutanamide

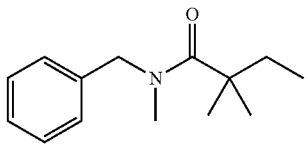 [SMILES: CCC(C)(C)C(=O)N(C)Cc1ccccc1]

The titled compound 90 was prepared in 72% yield from N-(2-fluorobenzyl)-2,2-dimethylbutanamide (1.312 g) and iodomethane (1 g) according to the procedure outlined for compound 10. $^1$H NMR (CDCl$_3$): δ 7.21-7.33 (m, 5H), 4.64 (s, 2H), 2.99 (s, 3H), 1.68 (q, 2H, J=7.6 Hz), 1.29 (s, 6H), 0.90 (t, 3H, J=7.6 Hz).

Compound 91: Preparation of N-(3,4-difluorobenzyl)-N,2,2-trimethylbutanamide

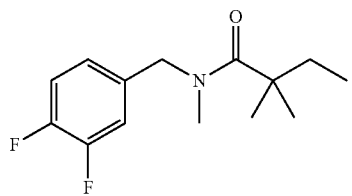

The titled compound 91 was prepared in 45% yield from compound 8 (71.7 mg) and iodomethane (84.5 mg) according to the procedure outlined for compound 10.
$^1$H NMR (CDCl$_3$): δ 7.03-7.14 (m, 2H), 6.94-6.98 (m, 1H), 4.55 (s, 2H), 3.02 (s, 3H), 1.69 (q, 2H, J=7.6 Hz), 1.29 (s, 6H), 0.89 (t, 3H, J=7.6 Hz).

Compound 92: Preparation of N-benzyl-N-hydroxy-2,2-dimethylbutanamide

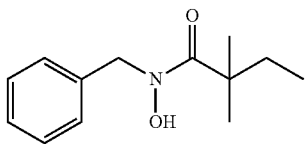 [SMILES: CCC(C)(C)C(=O)N(O)Cc1ccccc1]

n-benzylhydroxylamine hydrochloride (100 mg) was dissolved in 2 ml of THF/H$_2$O (1:1) and 0.45 ml of saturated aqueous NaHCO$_3$. The solution was cooled to 0° C. and 2,2-dimethylbutanoylchloride (81 mg) was added and the mixture was stirred at room temperature for 16 h. The mixture was extracted with EtOAc and the combined organic layer washed with brine, dried (Na$_2$SO4) and concentrated in vacuo. Purification by silica gel chromatography to give compound 80 (60 mg, 43.3%) as an white solid.
$^1$HNMR (CDCl$_3$, 400 MHz): δ7.34-37 (m, 2H), 7.31-7.33 (m, 3H), 4.89 (s, 2H), 1.69 (q, 2H, J=7.6 Hz), 1.26 (s, 6H), 0.86 (t, 6H, J=7.6 Hz). LC-MS (ESI) [M+H]+ calcd for C$_{13}$H$_{19}$NO$_2$, 222.1. found 222.4.

Compound 93: Preparation of N-hydroxy-2,2-dimethyl-N-(2,3,5-trifluorobenzyl)butanamide

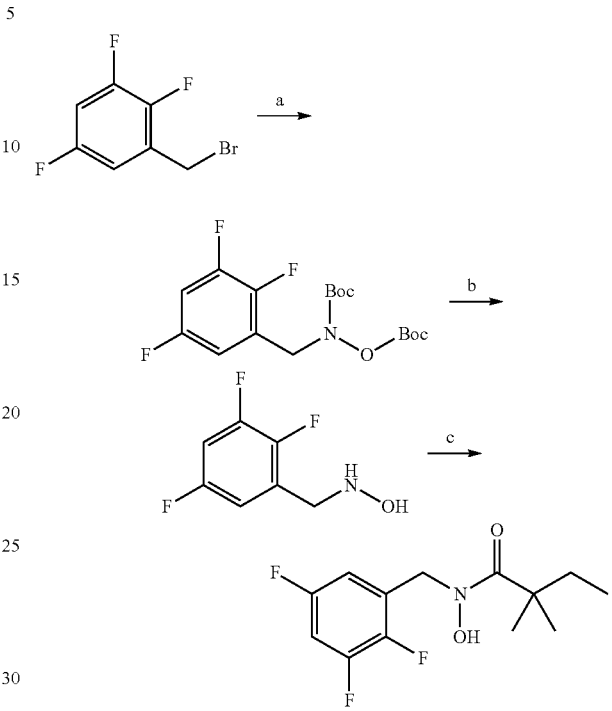

Reagent and conditions; (a) tert-butyl (tert-butoxycarbonyl)oxycarbamate, 1N NaOH, TBAB, DCM; (b) TFA, DCM; (c) 2,2-dimethylbutanoyl chloride, aq. NaHCO$_3$, THF, H$_2$O.

Tert-butyl (tert-butoxycarbonyl)oxycarbamate (104 mg) and 1-(bromomethyl)-2,3,5-trifluorobenzene (100 mg) were dissolved in CH$_2$Cl$_2$ (10 ml). The mixture was added 1M NaOH (4.5 ml) and tetrabutylammonium bromide (7 mg), and stirred at room temperature for overnight. The resulting mixture was washed with water and dried with Na$_2$SO$_4$, concentrated in vacuo and purification by silica gel chromatography to give tert-butyl (tert-butoxycarbonyl)oxy(2,3,5-trifluorobenzyl)-carbamate (150 mg, 89%). $^1$HNMR (CDCl$_3$, 400 MHz): δ 6.95-6.98 (m, 1H), 6.81-6.89 (m, 1H), 4.82 (s, 2H), 1.50 (s, 9H), 1.49 (s, 9H).

The above intermediate was dissolved in CH$_2$Cl$_2$ (2.5 ml), TFA (0.8 ml) was added at 0° C. The mixture was stirred at room temperature for 4 h and concentrated to give N-(2,3,5-trifluorobenzyl)hydroxylamine (100 mg) as a TFA salt, which was used without further purification.

The above intermediate was dissolved in THF (3 ml) and water (3 ml) and 1 ml of saturated aqueous NaHCO$_3$ was added. The mixture was stirred at room temperature for 30 min, then cooled to 0° C., 2,2-dimethylbutanoylchloride (54 mg) was added and stirred for overnight. The mixture was extracted with EtOAc, washed with brine, dried (Na$_2$SO4), and concentrated in vacuo. Purification by silica gel chromatography to give compound 93 (80 mg, total yield 65%). $^1$HNMR (CDCl$_3$, 400 MHz): δ 9.80 (s, 1H), 7.41-7.48 (m, 1H), 6.91-6.96 (m, 1H), 4.74 (s, 2H), 1.64 (q, 2H, J=7.6 Hz), 1.13 (s, 6H), 0.72 (t, 3H, J=7.6 Hz). LC-MS (ESI)[M+H]+ calcd for C$_{13}$H$_{16}$F$_3$NO$_2$, 276.1. found, 276.2.

Compound 94: Preparation of N-(4-fluorobenzyl)-N-hydroxy-2,2-dimethylbutanamide

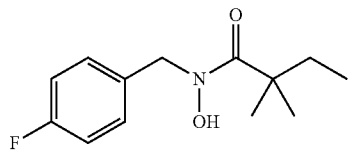

The titled compound 94 was prepared in 71% yield from tert-butyl (tert-butoxycarbonyl)oxycarbamate (247 mg), 1-(bromomethyl)-4-fluorobenzene (200 mg) and 2,2-dimethylbutanoylchloride (135 mg) according to the procedure outlined for compound 93. $^1$HNMR (CDCl$_3$, 400 MHz): δ7.27-7.31 (m, 2H), 7.02-7.06 (m, 2H), 4.85 (s, 2H), 1.68 (q, 2H, J=7.6 Hz), 1.26 (s, 6H), 0.84 (t, 3H, J=7.6 Hz). LC-MS (ESI)[M+H]$^+$ calcd for C$_{13}$H$_{18}$FNO$_2$, 240.1. found 240.2.

Compound 95: Preparation of N-(3,4-difluorobenzyl)-N-hydroxy-2,2-dimethylbutanamide

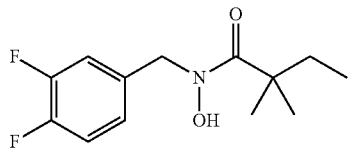

The titled compound 95 was prepared in 71% yield from tert-butyl (tert-butoxycarbonyl)oxycarbamate (225 mg), 4-(bromomethyl)-1,2-difluorobenzene (200 mg) and 2,2-dimethylbutanoylchloride (135 mg) according to the procedure outlined for compound 93. $^1$HNMR (CDCl$_3$, 400 MHz): δ7.10-7.17 (m, 2H), 7.02-7.06 (m, 1H), 4.81 (s, 2H), 1.68 (q, 2H, J=7.6 Hz), 1.25 (s, 6H), 0.84 (t, 3H, J=7.6 Hz). LC-MS (ESI)[M+H]$^+$ calcd for C$_{13}$H$_{17}$F$_2$NO$_2$, 258.1. found 258.2.

Compound 96: Preparation of N-(2,4-difluorobenzyl)-N-hydroxy-2,2-dimethylbutanamide

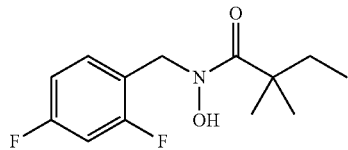

The titled compound 96 was prepared in 65% yield from tert-butyl (tert-butoxycarbonyl)oxycarbamate (225 mg), 1-(bromomethyl)-2,4-difluorobenzene (200 mg) and 2,2-dimethylbutanoylchloride (135 mg) according to the procedure outlined for compound 93. $^1$HNMR (CDCl$_3$, 400 MHz): δ77.32-7.38 (m, 1H), 6.80-6.90 (m, 2H), 4.90 (s, 2H), 1.68 (q, 2 H, J=7.6 Hz), 1.25 (s, 6H), 0.84 (t, 3H, J=7.6 Hz). LC-MS (ESI) [M+H]$^+$ calcd for C$_{13}$H$_{17}$F$_2$NO$_2$, 258.1. found 258.2.

Compound 97: Preparation of N-hydroxy-2,2-dimethyl-N-(2,3,4-trifluorobenzyl)butanamide

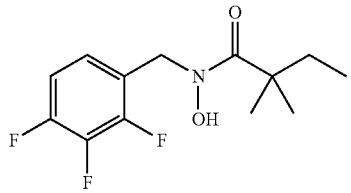 [SMILES: CCC(C)(C)C(=O)N(O)Cc1ccc(F)c(F)c1F]

The titled compound 97 was prepared in 65% yield from tert-butyl (tert-butoxycarbonyl)oxycarbamate (104 mg), 1-(bromomethyl)-2,3,4-trifluorobenzene (100 mg) and 2,2-dimethylbutanoylchloride (54 mg) according to the procedure outlined for compound 93. $^1$HNMR (CDCl$_3$, 400 MHz): δ7.08-7.14 (m, 1H), 6.93-7.00 (m, 1H), 4.92 (s, 2H), 1.68 (q, 2H, J=7.6 Hz), 1.25 (s, 6H), 0.84 (t, 3H, J=7.6 Hz). LC-MS (ESI) [M+H]$^+$ calcd for C$_{13}$H$_{16}$F$_3$NO$_2$, 276.1. found 276.2.

Compound 98: Preparation of N-hydroxy-2,2-dimethyl-N-(2,4,5-trifluorobenzyl)butanamide

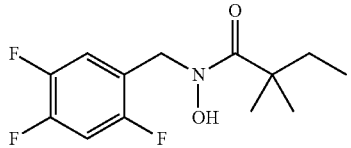 [SMILES: CCC(C)(C)C(=O)N(O)Cc1cc(F)c(F)cc1F]

The titled compound 98 was prepared in 65% yield from tert-butyl (tert-butoxycarbonyl)oxycarbamate (104 mg), 1-(bromomethyl)-2,4,5-trifluorobenzene (100 mg) and 2,2-dimethylbutanoylchloride (54 mg) according to the procedure outlined for compound 93. $^1$HNMR (CDCl$_3$, 400 MHz): δ7.19-7.24 (m, 1H), 6.91-6.98 (m, 1H), 4.88 (s, 2H), 1.68 (q, 2H, J=7.6 Hz), 1.25 (s, 6H), 0.84 (t, 3H, J=7.6 Hz). LC-MS (ESI) [M+H]$^+$ calcd for C$_{13}$H$_{16}$F$_3$NO$_2$, 276.1. found 276.2.

Compound 99: Preparation of N-hydroxy-2,2-dimethyl-N-(3,4,5-trifluorobenzyl)butanamide

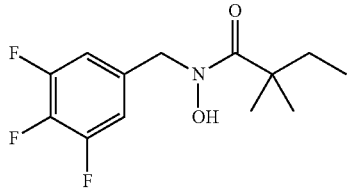 [SMILES: CCC(C)(C)C(=O)N(O)Cc1cc(F)c(F)c(F)c1]

The titled compound 99 was prepared in 65% yield from tert-butyl (tert-butoxycarbonyl)oxycarbamate (104 mg), 5-(bromomethyl)-1,2,3-trifluorobenzene (100 mg) and 2,2-dimethylbutanoylchloride (54 mg) according to the procedure outlined for compound 93. $^1$HNMR (CDCl$_3$, 400 MHz): δ6.92-7.00 (m, 2H), 4.79 (s, 2H), 1.68 (q, 2H, J=7.6 Hz), 1.26 (s, 6H), 0.85 (t, 3H, J=7.6 Hz). LC-MS (ESI) [M+H]$^+$ calcd for C$_{13}$H$_{16}$F$_3$NO$_2$, 276.1. found, 276.2.

Compound 100: Preparation of (S)-methyl 3-(2,2-dimethylbutanamido)-3-phenylpropanoate

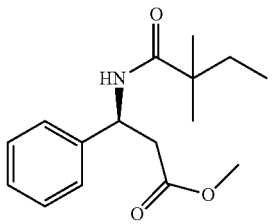 [SMILES: CCC(C)(C)C(=O)N[C@@H](CC(=O)OC)c1ccccc1]

(S)-3-amino-3-phenylpropanoic acid (1 g) was dissolved in methanol (10 ml), 1 ml of thionyl chloride was added at 0° C. The mixture was refluxed for 4 h. The solvent was evaporated to dryness and the resulting solid was washed with petroleum ether. The crude product and triethylamine (0.7 ml) were dissolved in 15 ml of $CH_2Cl_2$, 2,2-dimethylbutanoylchloride (1 g) was added slowly at 0° C. under nitrogen. The mixture was stirred at room temperature for 4 h. After removal of solvent and purified by silica gel column chromatography to give compound 100 (110 mg, 32%). $^1$HNMR (CDCl$_3$, 400 MHz): δ7.31-7.35 (m, 2H), 7.23-7.28 (m, 3H), 5.40-5.45 (m, 1H), 3.62 (s, 3H), 2.87 (m, 2H), 1.57 (q, 2H, J=7.6 Hz), 1.19 (s, 3H), 1.18 (s, 3H), 0.83 (t, 3H, J=7.6 Hz). LC-MS (ESI) [M+H]$^+$ calcd for $C_{16}H_{23}NO_3$, 278.2. found 278.4.

Compound 101: Preparation of (S)-2,2-dimethyl-N-(3-(methylamino)-3-oxo-1-phenylpropyl)butanamide

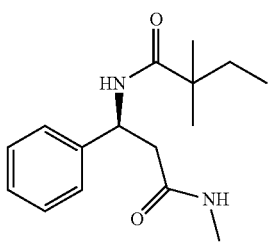 [SMILES: CCC(C)(C)C(=O)N[C@@H](CC(=O)NC)c1ccccc1]

Compound 100 (840 mg) was dissolved in 30 ml of methanol, 1M NaOH (40 ml) was added. The mixture was stirred at room temperature for 5 h. The solvent was removed and acidified with 1N HCl. The aqueous phase was extracted with $CH_2Cl_2$. The combined organic layer was wash with water, dried with $Na_2SO_4$. Filtered and evaporated to dryness to give (S)-3-(2,2-dimethylbutanamido)-3-phenylpropanoic acid (780 mg, 98%) as a brown oil. $^1$HNMR (CDCl$_3$, 400 MHz): δ 7.31-7.34 (m, 2H), 7.24-7.28 (m, 3H), 6.75 (d, 1H, J=8.4 Hz), 5.40-5.45 (m, 1H), 2.83-2.93 (m, 2H), 1.55 (q, 2H, J=7.6 Hz), 1.16 (s, 1H), 1.15 (s, 1H), 0.81 (t, 3H, J=7.6 Hz).

The titled compound 101 was prepared in 55% yield from (S)-3-(2,2-dimethylbutanamido)-3-phenylpropanoic acid (30 mg) and methanamine hydrochloride (9.2 mg) according to the procedure for compound 65. $^1$HNMR (CDCl$_3$, 400 MHz): δ7.83 (brs, 1H), 7.26-7.33 (m, 3H), 7.21-7.25 (m, 2H), 5.92 (brs, 1H), 5.26-5.31 (m, 1H), 3.67-3.72 (m, 1H), 3.12-3.19 (m, 1H), 2.71 (d, 3H, J=4.8 Hz), 1.58 (m, 2H), 1.20 (s, 3H), 1.19 (s, 3H), 0.82 (t, 3H, J=7.6 Hz). LC-MS (ESI) [M+H]$^+$ calcd for $C_{15}H_{21}NO_3$, 277.2. found 277.4.

Compound 102: Preparation of (S)—N-(3-((2-(2-methoxyethoxy)ethyl)amino)-3-oxo-1-phenylpropyl)-2,2-dimethylbutanamide

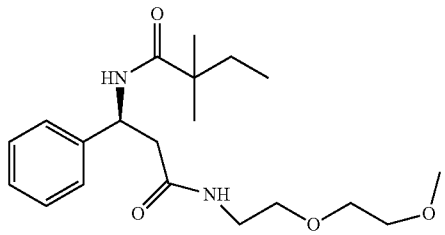 [SMILES: CCC(C)(C)C(=O)N[C@@H](CC(=O)NCCOCCOC)c1ccccc1]

The titled compound 102 was prepared in 51% yield from (S)-3-(2,2-dimethylbutanamido)-3-phenylpropanoic acid (30 mg) and 2-(2-methoxyethoxy)ethanamine (16.3 mg) according to the procedure outlined for compound 101. $^1$HNMR (CDCl$_3$, 400 MHz): δ7.98-8.01 (brs, 1H), 7.27-7.33 (m, 4H), 7.21-7.25 (m, 1H), 6.41-6.45 (brs, 1H), 5.27-5.32 (m, 1H), 3.67-3.74 (m, 1H), 3.40-3.56 (m, 5H), 3.36 (s, 3H), 3.13-3.19 (m, 2H), 2.78-2.83 (m, 1H), 2.68-2.73 (m, 1H), 1.54-1.62 (m, 2H), 1.22 (s, 3H), 1.21 (s, 3H), 0.83 (t, 3H, J=7.2 Hz). LC-MS (ESI) [M+H]$^+$ calcd for $C_{20}H_{32}N_2O_4$, 365.2. found 365.4.

Compound 103: Preparation of (S)—N-(3-(ethylamino)-3-oxo-1-phenylpropyl)-2,2-dimethylbutanamide

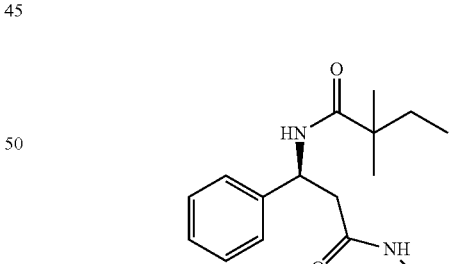

The titled compound 103 was prepared in 39% yield from (S)-3-(2,2-dimethylbutanamido)-3-phenylpropanoic acid (30 mg) and ethylamine hydrochloride (11 mg) according to the procedure outlined for compound 101. $^1$HNMR (CDCl$_3$, 400 MHz): δ $^1$H-NMR (CDCl3) δ 7.87-7.89 (brs, 1H), 7.27-7.32 (m, 4H), 7.23-7.25 (m, 1H), 5.74 (brs, 1H), 5.28-5.32 (m, 1H), 3.12-3.24 (m, 2H), 2.757 (dd, 1H, J=4.8, 14.4 Hz), 2.582 (dd, 1H, J=5.6, 14.4 Hz), 1.56-1.62 (qd, 2H, J=7.2, 1.6 Hz), 1.21 (s, 3H), 1.21 (s, 3H), 1.006 (t, 3H, J=7.2 Hz), 0.823 (t, 3H, J=7.2 Hz) LC-MS (ESI) [M+H]$^+$ calcd for $C_{17}H_{26}N_2O_2$, 291. found 291.2.

Compound 104: Preparation of (S)—N-(3-(cyclohexylamino)-3-oxo-1-phenylpropyl)-2,2-dimethylbutanamide

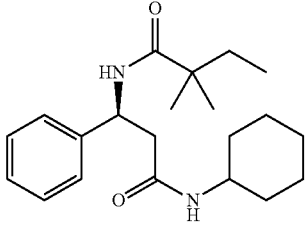 [SMILES: CCC(C)(C)C(=O)N[C@@H](CC(=O)NC1CCCCC1)c1ccccc1]

The titled compound 104 was prepared in 21% yield from (S)-3-(2,2-dimethylbutanamido)-3-phenylpropanoic acid (30 mg) and cyclohexanamine (14 mg) according to the procedure outlined for compound 101. ¹HNMR (CDCl₃, 400 MHz): δ7.95 (brs, 1H), 7.27-7.31 (m, 3H), 7.20-7.24 (m, 2H), 5.41 (brs, 1H), 5.28-5.32 (m, 1H), 3.62-3.71 (m, 1H), 2.73 (dd, 1H, J=4.8, 14.4 Hz), 2.50 (dd, 1H, J=4.8, 14.4 Hz), 1.79-1.82 (m, 2H), 1.56-1.67 (m, 6H), 1.26-1.36 (m, 2H), 1.21 (s, 3H), 1.20 (s, 3H), 1.01-1.13 (m, 2H), 0.82 (t, 3H, J=7.6 Hz). LC-MS (ESI) [M+H]⁺ calcd for $C_{21}H_{32}N_2O_2$, 345.2. found 345.4.

Compound 105: Preparation of (S)-2,2-dimethyl-N-(3-oxo-1-phenyl-3-(piperidin-1-yl)propyl)butanamide

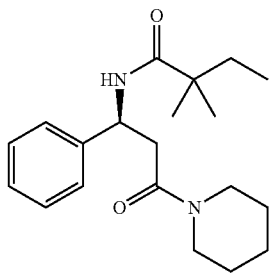 [SMILES: CCC(C)(C)C(=O)N[C@@H](CC(=O)N1CCCCC1)c1ccccc1]

The titled compound 105 was prepared in 29% yield from (S)-3-(2,2-dimethylbutanamido)-3-phenylpropanoic acid (30 mg) and piperidine (14 mg) according to the procedure outlined for compound 101. ¹HNMR (CDCl₃, 400 MHz): δ7.99 (brs, 1H), 7.27-7.32 (m, 4H), 7.19-7.23 (m, 1H), 5.32 (m, 1H), 3.56-3.60 (m, 1H), 3.32-3.39 (m, 1H), 3.17-3.24 (m, 2H), 3.033 (dd, 1H, J=5.6, 14.4 Hz), 2.679 (dd, 1H, J=4.8, 14.4 Hz), 1.55-1.61 (m, 2H), 1.50-1.54 (m, 2H), 1.36-1.48 (m, 3H), 1.20 (s, 3H), 1.19 (s, 3H), 1.04-1.10 (m, 1H), 0.83 (t, 3H, J=7.6 Hz). LC-MS (ESI) [M+H]⁺ calcd for $C_{20}H_{30}N_2O_2$, 331.2. found 331.4.

Compound 106: Preparation of (S)-2,2-dimethyl-N-(3-oxo-1-phenyl-3-(phenylamino)propyl)butanamide

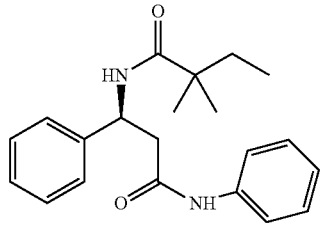 [SMILES: CCC(C)(C)C(=O)N[C@@H](CC(=O)Nc1ccccc1)c1ccccc1]

The titled compound 106 was prepared in 28% yield from (S)-3-(2,2-dimethylbutanamido)-3-phenylpropanoic acid (30 mg) and aniline (13 mg) according to the procedure outlined for compound 101. ¹HNMR (CDCl₃, 400 MHz): δ7.65 (brs, 1H), 7.27-7.40 (m, 9H), 7.106 (t, 1H, J=7.2 Hz), 5.41-5.45 (m, 1H), 2.83-2.99 (m, 2H), 1.578 (q, 2H, J=7.6 Hz), 1.19 (s, 6H), 0.81 (t, 3H, J=7.6 Hz). LC-MS (ESI) [M+H]⁺ calcd for $C_{21}H_{26}N_2O_2$, 339.2. found, 339.4.

Compound 107: Preparation of (S)—N-(3-(benzylamino)-3-oxo-1-phenylpropyl)-2,2-dimethylbutanamide

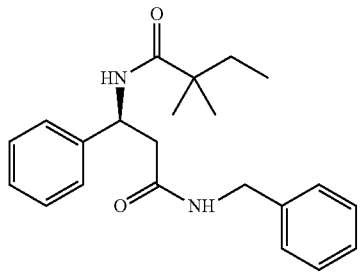 [SMILES: CCC(C)(C)C(=O)N[C@@H](CC(=O)NCc1ccccc1)c1ccccc1]

The titled compound 107 was prepared in 28% yield from (S)-3-(2,2-dimethylbutanamido)-3-phenylpropanoic acid (30 mg) and phenylmethanamine (15 mg) according to the procedure outlined for compound 101. ¹HNMR (CDCl₃, 400 MHz): δ7.91 (brs, 1H), 7.28-7.39 (m, 8H), 7.02-7.04 (m, 2H), 6.29 (brs, 1H), 5.33-5.36 (m, 1H), 4.39 (d, 2H, J=5.2 Hz), 2.84-2.91 (m, 1H), 2.71-2.76 (m, 1H), 1.59 (qd, 2H, J=1.2, 7.6 Hz), 1.21 (s, 3H), 1.20 (s, 3H), 0.83 (t, 3H, J=7.6 Hz). LC-MS (ESI)[M+H]⁺ calcd for $C_{22}H_{28}N_2O_2$, 353.2. found, 353.4.

Compound 108: Preparation of (S)-2,2-dimethyl-N-(3-oxo-3-(phenethylamino)-1-phenylpropyl)butanamide

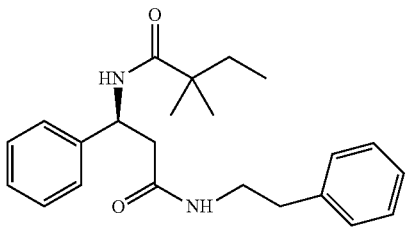 [SMILES: CCC(C)(C)C(=O)N[C@@H](CC(=O)NCCc1ccccc1)c1ccccc1]

The titled compound 108 was prepared in 31% yield from (S)-3-(2,2-dimethylbutanamido)-3-phenylpropanoic acid (30 mg) and phenylmethanamine (16 mg) according to the procedure outlined for compound 101. ¹HNMR (CDCl₃, 400 MHz): δ7.96-7.98 (brs, 1H), 7.27-7.34 (m, 4H), 7.17-7.25 (m, 4H), 6.94-6.97 (m, 2H), 5.59 (brs, 1H), 5.28-5.32 (m, 1H), 3.46-3.55 (m, 1H), 3.25-3.33 (m, 1H), 2.67-2.75 (m, 2H), 2.49-2.61 (m, 2H), 1.58 (qd, 2H, J=2.0, 7.6 Hz), 1.22 (s, 3H), 1.21 (s, 3H), 0.84 (t, 3H, J=7.6 Hz). LC-MS (ESI) [M+H]⁺ calcd for $C_{23}H_{30}N_2O_2$, 367.2. found, 367.4.

Compound 109: Preparation of (R)—N-(2-hydroxy-1-phenylethyl)-2,2-dimethylbutanamide

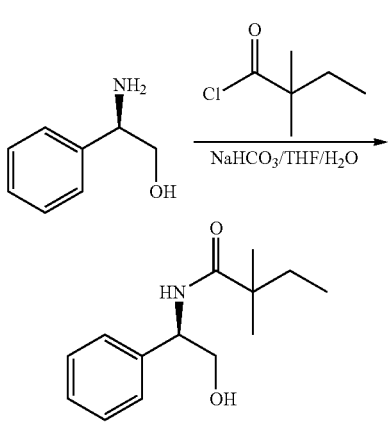

(R)-2-amino-2-phenylethanol (50 mg, 0.365 mmoL) and NaHCO₃ (91.9 mg, 1.094 mmol) were dissolved in 2 mL of THF/H₂O (v/v=1/1). 2,2-dimethylbutanoylchloride (43 mg, 0.398 mmoL) was added slowly to the solution at 0° C. under nitrogen. The mixture was stirred at room temperature for 16 h, and extracted with EtOAc (15 mL×3). The combined organic layers were washed with brine, dried with Na₂SO₄. Filtered and evaporated to dryness. The residue was purified by column chromatography to give compound 109 as white solid (45 mg, 59.2%). ¹H NMR: (CDCl₃, 400 M Hz): δ (ppm) 7.35-7.39 (m, 2H), 7.28-7.32 (m, 3H), 6.26 (brs, 1H), 5.05-5.09 (m, 1H), 3.87-3.94 (m, 2H), 2.70 (brs, 1H), 1.59 (q, 2H, J=7.6 Hz), 1.20 (s, 3H), 1.19 (s, 3H), 0.87 (t, 3H, J=7.6 Hz). LC-MS (ESI) [M+H]⁺ calcd for $C_{14}H_{21}NO_2$, 236.2. found 236.3.

Compound 110: Preparation of N-(2-hydroxy-1-phenylethyl)-2,2-dimethylbutanamide

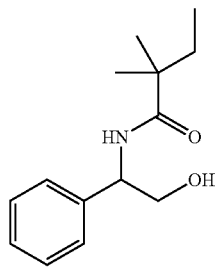 [SMILES: CCC(C)(C)C(=O)NC(CO)c1ccccc1]

The titled compound 110 was prepared in 78.3% yield from 2-amino-2-phenylethanol (50 mg) and 2,2-dimethylbutanoyl chloride (54 mg) according to the procedure outlined for compound 109. ¹H NMR: (CDCl₃, 400 M Hz) δ7.36-7.40 (m, 2H), 7.28-7.33 (m, 3H), 6.27 (brs, 1H), 5.07 (dd, 1H, J=5.6, 10.8 Hz), 3.88-3.92 (m, 2H), 2.72 (brs, 1H), 1.58 (q, 2H, J=7.6 Hz), 1.20 (s, 3H), 1.19 (s, 3H), 0.87 (t, 3H, J=7.6 Hz). LC-MS (ESI) [M+H]⁺ calcd for $C_{15}H_{23}NO_2$, 236.2. found 236.3.

Compound 111: Preparation of N-(2-hydroxy-1-phenylethyl)-N,2,2-trimethylbutanamide

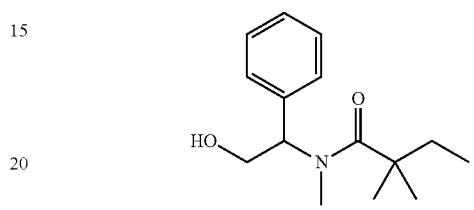

The titled compound 111 was prepared in 9.8% yield from 2-(methylamino)-2-phenylethanol (50 mg) and 2,2-dimethylbutanoyl chloride (48 mg) according to the procedure outlined for compound 109. ¹H NMR: (MeOD, 400 M Hz) δ7.43-7.44 (m, 3H), 7.28-7.38 (m, 2 H), 4.29-4.38 (m, 2H), 5.88 (m, 1H), 2.43 (s, 3H), 1.528 (q, 2H, J=7.6 Hz), 1.11 (s, 6H), 0.75 (t, 3H, J=7.6 Hz). LC-MS (ESI)[M+H]⁺ calcd for $C_{15}H_{23}NO_2$, 250.2. found 250.3.

Compound 112: Preparation of N-(2-methoxy-1-phenylethyl)-N,2,2-trimethylbutanamide

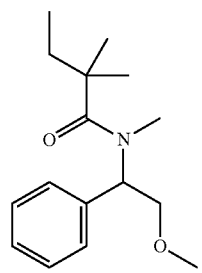 [SMILES: CCC(C)(C)C(=O)N(C)C(COC)c1ccccc1]

N-(2-hydroxy-1-phenylethyl)-2,2-dimethylbutanamide (40 mg, 0.17 mmoL) was dissolved in 2 mL of dry THF. NaH (20.4 mg, 0.51 mmoL, 60% in material oil) was added in portions to the solution at 0° C. under nitrogen. After stirring at 0° C. for 0.5 h, iodomethane (72.5 mg, 0.51 mmoL) was added. The mixture was stirred at room temperature for 16 h, quenched with water (1 ml) and extracted with EtOAc. The combined organic layers were evaporated to dryness and the residue was purified by column chromatography to give compound 112 (20 mg, 44.7%) as colorless oil. ¹H NMR: (CDCl₃, 400 M Hz) δ7.31-7.35 (m, 2H), 7.22-7.28 (m, 3H), 5.70-6.20 (m, 1H), 3.81-3.90 (m, 2H), 3.41 (s, 3H), 2.84 (s, 3H), 1.63-1.73 (m, 2H), 1.29 (s, 3H), 1.28 (s, 3H), 0.91 (t, 3H, J=7.6 Hz). LC-MS (ESI)[M+H]⁺ calcd for $C_{16}H_{25}NO_2$, 264.2. found, 264.4.

Compound 113: Preparation of 3-cyclohexyl-1-(2-fluorobenzyl)-1-methylurea

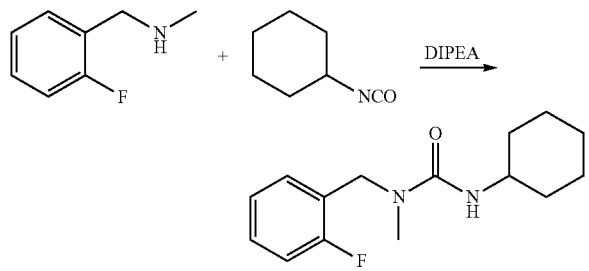

To a solution of 1-(2-fluorophenyl)-N-methylmethanamine (97 mg) in THF (10 ml) was added N,N-Diisopropylethylamine (135 mg), then isocyanatocyclohexane (131 mg) in THF (1 ml) was added. The mixture was stirred for overnight and diluted with water. The aqueous layer was extracted with CH$_2$Cl$_2$ and the combined organic layers were washed with water and brine, dried (Na$_2$SO$_4$) and concentrated in vacuo. The residue was purified by column chromatography to give compound 113 (65 mg, 35%). $^1$HNMR: (CDCl$_3$, 400 M Hz): δ7.22-7.34 (m, 2H), 7.02-7.14 (m, 2H), 4.53 (s, 2H), 3.59-3.71 (m, 1H), 2.90 (s, 3H), 1.91-1.97 (m, 2H), 1.57-1.71 (m, 3H), 1.31-1.42 (m, 2H), 1.03-1.18 (m, 3H). LC-MS (ESI) [M+H]$^+$ calcd for C$_{15}$H$_{21}$FN$_2$O, 265.2. found 265.4.

Compound 114: Preparation of 1-(2-fluorobenzyl)-3-isopropyl-1-methylurea

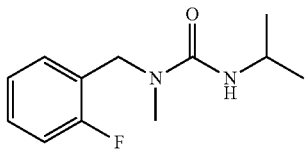 [SMILES: CC(C)NC(=O)N(C)Cc1ccccc1F]

The titled compound 117 was prepared in 30% yield from 2-isocyanatopropane (92 mg) and 1-(2-fluorophenyl)-N-methylmethanamine (97 mg) according to the procedure outlined for compound 113. $^1$H NMR: (CDCl$_3$, 400 M Hz): δ7.22-7.32 (m, 2H), 7.02-7.14 (m, 2H), 4.53 (s, 2H), 3.96-4.03 (m, 1H), 2.89 (s, 3H), 1.15 (d, 6H, J=6.4 Hz), LC-MS (ESI) [M+H]$^+$ calcd for C$_{12}$H$_{17}$FN$_2$O, 225.1. found 225.2.

Compound 115: Preparation of 1-ethyl-3-isopropyl-3-methyl-1-(2,3,5-trifluorobenzyl)urea

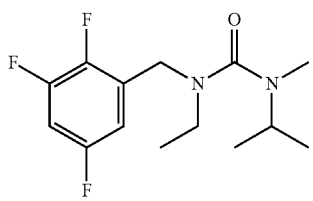 [SMILES: CCN(Cc1cc(F)cc(F)c1F)C(=O)N(C)C(C)C]

To a solution of triphosgene (154 mg) in dichloromethane (4 ml) was added N-methylpropan-2-amine (40 mg) at 0° C. under nitrogen The mixture was stirred at 0° C. for 4 h. Then the solvent was removed, and a solution of N-(2,3,5-trifluorobenzyl)-ethanamine (60 mg) in dichloromethane (2 ml) was added. The mixture was stirred at 35° C. for overnight, diluted with water. The aqueous layer was extracted with EtOAc (5 mL×3). The combined organic layers were washed with saturated NaHCO$_3$ and brine, dried with Na$_2$SO$_4$, filtered and evaporated to dryness. The residue was purified by column chromatography to give compound 115 (4 mg, 2.5%) as a yellow oil. $^1$H NMR: (CDCl$_3$, 400 M Hz): δ6.86-6.89 (m, 1H), 6.76-6.81 (m, 1H), 4.38 (s, 2H), 4.07 (m, 1H), 3.09-3.14 (q, 2H, J=7.2 Hz), 2.70 (s, 3H), 1.13-1.17 (m, 9H). LC-MS (ESI) [M+H]$^+$ calcd for C$_{14}$H$_{19}$F$_3$N$_2$O, 289.1. found 289.2.

Compound 116: Preparation of 2-ethyl-N-methyl-N-(2,3,5-trifluorobenzyl)piperidine-1-carboxamide

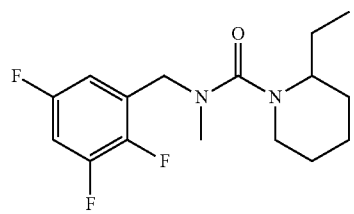 [SMILES: CCC1CCCCN1C(=O)N(C)Cc1cc(F)cc(F)c1F]

The titled compound 119 was prepared in 14.9% yield from triphosgene (77.1 mg), 2-ethylpiperidine (29.4 mg) and N-methyl-1-(2,3,5-trifluorophenyl)methanamine (30 mg) according to the procedure outlined for compound 115. $^1$H NMR: (CDCl$_3$, 400 M Hz): δ6.79-6.88 (m, 2H), 4.45 (d, 1H, J=15.6 Hz), 4.29 (d, 1H, J=15.6 Hz), 3.72-3.74 (m, 1H), 3.43-3.48 (m, 1H), 2.94-3.01 (m, 1H), 2.77 (s, 3H), 1.57-1.70 (m, 8H), 0.98 (t, 3H, J=7.6 Hz). LC-MS (ESI) [M+H]$^+$ calcd for C$_{16}$H$_{21}$F$_3$N$_2$O, 315.2. found 315.3.

Compound 117: Preparation of N,2-dimethyl-N-(2,3,5-trifluorobenzyl)piperidine-1-carboxamide

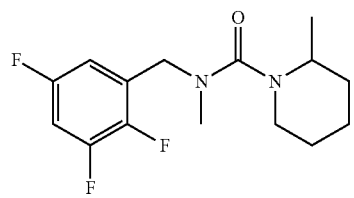 [SMILES: CC1CCCCN1C(=O)N(C)Cc1cc(F)cc(F)c1F]

The titled compound 120 was prepared in 15.6% yield from triphosgene (77.1 mg), 2-methylpiperidine (25.71 mg) and N-methyl-1-(2,3,5-trifluorophenyl)methanamine (30 mg) according to the procedure outlined for compound 115. $^1$H NMR: (CDCl$_3$, 400 M Hz): δ6.78-6.84 (m, 2H), 4.43 (d, 1H, J=16 Hz), 4.34 (d, 1H, J=16 Hz), 3.90-3.93 (m, 1H), 3.32-3.36 (m, 1H), 2.95-3.02 (m, 1H), 2.76 (s, 3H), 1.44-1.68 (m, 6H), 1.18 (d, 3H, J=4 Hz). LC-MS (ESI) [M+H]$^+$ calcd for C$_{15}$H$_{19}$F$_3$N$_2$O, 301.1. found 301.3.

Compound 118: Preparation of N,3-dimethyl-N-(2,3,5-trifluorobenzyl)piperidine-1-carboxamide

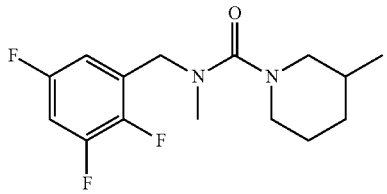 [SMILES: CC1CCCN(C(=O)N(C)Cc2cc(F)cc(F)c2F)C1]

The titled compound 121 was prepared in 9.7% yield from triphosgene (84.8 mg), 2-methylpiperidine (28.3 mg) and N-methyl-1-(2,3,5-trifluorophenyl)methanamine (30 mg) according to the procedure outlined for compound 115. $^1$H NMR: (CDCl$_3$, 400 MHz): δ7.05-7.07 (m, 1H), 6.89-6.91 (m, 1H), 4.42-4.84 (m, 2H), 2.80 (s, 3H), 3.49-3.53 (m, 2H), 2.75-2.77 (m, 2H), 1.77-1.79 (m, 1H), 1.57-1.67 (m, 4H), 0.98 (d, 3H, J=6.4 Hz). LC-MS (ESI) [M+H]$^+$ calcd for C$_{15}$H$_{19}$F$_3$N$_2$O, 301.1. found 301.3.

Compound 119: Preparation of 1,1-diisopropyl-3-methyl-3-(2,3,5-trifluorobenzyl)urea

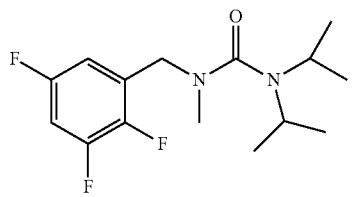 [SMILES: CC(C)N(C(=O)N(C)Cc1cc(F)cc(F)c1F)C(C)C]

The titled compound 119 was prepared in 19.3% yield from triphosgene (84.8 mg), diisopropylamine (26.86 mg) and N-methyl-1-(2,3,5-trifluorophenyl)methanamine (30 mg) according to the procedure outlined for compound 115. $^1$H NMR: (CDCl$_3$, 400 M Hz): δ6.79-6.82 (m, 2H), 4.30 (s, 2H), 3.58-3.62 (m, 2H), 2.68 (s, 3H), 1.26 (d, 12H, J=6.4 Hz). LC-MS (ESI) [M+H]$^+$ calcd for C$_{15}$H$_{21}$F$_3$N$_2$O, 303.2. found 303.4.

Compound 120: Preparation of isopropyl-1,3-dimethyl-3-(2,3,5-trifluorobenzyl)urea

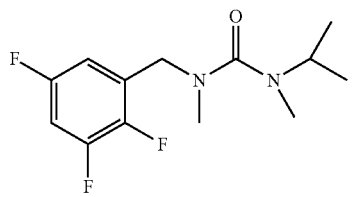 [SMILES: CC(C)N(C)C(=O)N(C)Cc1cc(F)cc(F)c1F]

The titled compound 120 was prepared in 20.8% yield from triphosgene (84.8 mg), N-methylpropan-2-amine (20.86 mg) and N-methyl-1-(2,3,5-trifluorophenyl)methanamine (30 mg) according to the procedure outlined for compound 115. $^1$H NMR: (CDCl$_3$, 400 M Hz): δ6.80-6.87 (m, 2H), 4.38 (s, 2H), 4.00-4.11 (m, 1H), 2.75 (s, 3H), 2.67 (s, 3H), 1.10 (d, 6H, J=6.4 Hz). LC-MS (ESI) [M+H]$^+$ calcd for C$_{13}$H$_{17}$F$_3$N$_2$O, 275.1. found 275.2.

Compound 121: Preparation of N,2,6-trimethyl-N-(2,3,5-trifluorobenzyl)piperidine-1-carboxamide

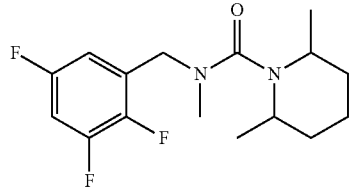 [SMILES: CC1CCCC(C)N1C(=O)N(C)Cc1cc(F)cc(F)c1F]

The titled compound 121 was prepared in 14.5% yield from triphosgene (84.8 mg), 2,6-dimethylpiperidine (32.28 mg) and N-methyl-1-(2,3,5-trifluorophenyl)methanamine (30 mg) according to the procedure outlined for compound 115. $^1$H NMR: (CDCl$_3$, 400 M Hz): δ6.80-6.90 (m, 2H), 4.61 (s, 2H), 3.18-3.23 (m, 2H), 2.97 (s, 3H), 1.70-1.75 (m, 1H), 1.59-1.65 (m, 2H), 1.32-1.45 (m, 1H), 1.22-1.39 (m, 2H), 1.12 (d, 6H, J=6.4 Hz). LC-MS (ESI) [M+H]$^+$ calcd for C$_{16}$H$_{21}$F$_3$N$_2$O, 315.2. found 315.4.

Compound 122: Preparation of (R)-2,2-dimethyl-N-(2-(methylamino)-2-oxo-1-phenylethyl)butanamide

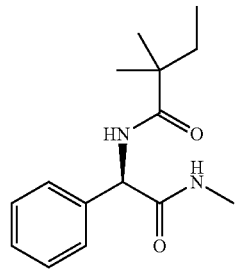 [SMILES: CCC(C)(C)C(=O)N[C@@H](C(=O)NC)c1ccccc1]

The titled compound 122 was prepared in 35% yield from (R)-2-(2,2-dimethylbutanamido)-2-phenylacetic acid (30 mg), which was prepared from (R)-2-amino-2-phenylacetic acid according to the procedure outlined for compound 101, and methanamine hydrochloride (10 mg) according to the procedure outlined for compound 65. $^1$HNMR (CDCl$_3$, 400 MHz): δ7.28-7.38 (m, 5H), 7.14 (brs, 1H), 6.38 (brs, 1H), 5.52 (d, J=6.8 Hz, 1H), 2.77 (d, J=4.8 Hz, 3H), 1.51-1.60 (m, 2H), 1.18 (s, 3H), 1.17 (s, 3H), 0.78 (t, 3H, J=7.6 Hz). LC-MS (ESI) [M+H]$^+$ calcd for C$_{15}$H$_{22}$N$_2$O$_2$, 263.2. found, 263.3.

Compound 123: Preparation of (R)—N-(2-(dimethylamino)-2-oxo-1-phenylethyl)-2,2-dimethylbutanamide

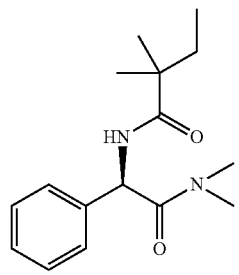 [SMILES: CCC(C)(C)C(=O)N[C@@H](C(=O)N(C)C)c1ccccc1]

The titled compound 186 was prepared in 35% yield from (R)-2-(2,2-dimethylbutanamido)-2-phenylacetic acid (30 mg) and dimethylamine (6.48 mg) according to the procedure outlined for compound 65. $^1$HNMR (CDCl$_3$, 400 MHz): δ7.28-7.41 (m, 5H), 5.80 (d, 1H, J=6.8 Hz), 2.99 (s, 3H), 2.89 (s, 3H), 1.45-1.55 (m, 2H), 1.13 (s, 3H), 1.12 (s, 3H), 0.70 (t, 3H, J=7.6 Hz). LC-MS (ESI) [M+H]$^+$ calcd for C$_{16}$H$_{24}$N$_2$O$_2$, 277.2. found, 277.4.

Compound 124: Preparation of (R)—N-(2-(benzylamino)-2-oxo-1-phenylethyl)-2,2-dimethylbutanamide

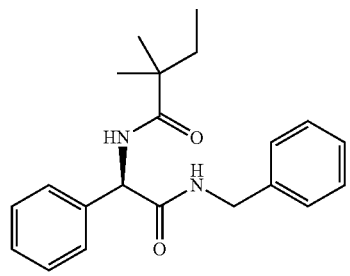 [SMILES: CCC(C)(C)C(=O)N[C@@H](C(=O)NCc1ccccc1)c1ccccc1]

The titled compound 124 was prepared in 37% yield from (R)-2-(2,2-dimethylbutanamido)-2-phenylacetic acid (30 mg) and phenylmethanamine (15.4 mg) according to the procedure outlined for compound 65. $^1$HNMR (CDCl$_3$, 400 MHz): δ 7.28-7.38 (m, 5H), 7.23-7.26 (m, 2H), 7.07-7.12 (m, 3H), 6.14 (brs, 1H), 5.49 (d, 1H, J=6.4 Hz), 4.42 (d, 2H, J=5.2 Hz), 1.49-1.55 (m, 2H), 1.16 (s, 3H), 1.15 (s, 3H), 0.76 (t, 3H, J=7.6 Hz). LC-MS (ESI) [M+H]$^+$ calcd for C$_{21}$H$_{26}$N$_2$O$_2$, 339.2. found, 339.4.

Compound 125: Preparation of (R)-2,2-dimethyl-N-(2-oxo-2-(phenethylamino)-1-phenylethyl)butanamide

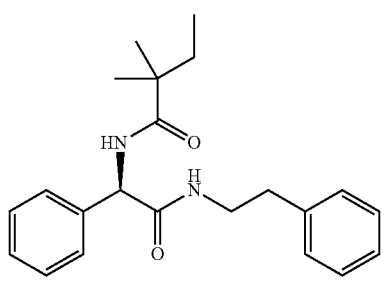 [SMILES: CCC(C)(C)C(=O)N[C@@H](C(=O)NCCc1ccccc1)c1ccccc1]

The titled compound 188 was prepared in 38% yield from (R)-2-(2,2-dimethylbutanamido)-2-phenylacetic acid (30 mg) and 2-phenylethanamine (17.4 mg) according to the procedure outlined for compound 65. $^1$HNMR (CDCl$_3$, 400 MHz): δ7.28-7.35 (m, 5H), 7.17-7.23 (m, 3H), 7.11-7.12 (brs, 1H), 6.92-6.94 (m, 2H), 5.57 (brs, 1H), 5.25-5.27 (d, 1H, J=6.0 Hz), 3.57-3.65 (m, 1H), 3.32-3.40 (m, 1H), 2.63-2.77 (m, 2H), 1.50-1.56 (qd, 2H, J=7.6, 2.0 Hz), 1.16 (s, 3H), 1.15 (s, 3H), 0.76 (t, 3H, J=7.6 Hz). LC-MS (ESI) [M+H]$^+$ calcd for C$_{22}$H$_{28}$N$_2$O$_2$, 353.2. found, 353.4.

Compound 126: Preparation of (S)-2,2-dimethyl-N-(3-oxo-3-((2-phenoxyethyl)amino)-1-phenylpropyl)butanamide

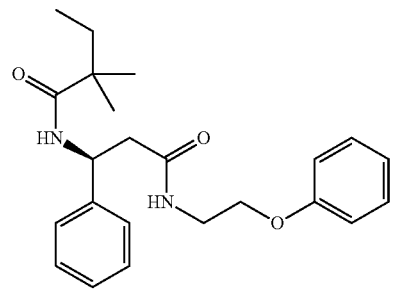 [SMILES: CCC(C)(C)C(=O)N[C@@H](CC(=O)NCCOc1ccccc1)c1ccccc1]

The titled compound 126 was prepared in 42% yield from (S)-3-(2,2-dimethylbutanamido)-3-phenylpropanoic acid (30 mg) and 2-phenoxyethanamine (19 mg) according to the procedure outlined for compound 65. $^1$HNMR (CDCl$_3$, 400 MHz): δ 7.79-7.81 (brs, 1H), 7.27-7.31 (m, 2H), 7.19-7.26 (m, 4H), 7.09-7.13 (m, 1H), 6.95-7.00 (m, 1H), 6.78-6.81 (m, 2H), 5.94 (brs, 1H), 5.31-5.35 (m, 1H), 3.90-3.94 (m, 1H), 3.79-3.84 (m, 1H), 3.50-3.61 (m, 2H), 2.77 (dd, 1H, J=4.8, 14.4 Hz), 2.62 (dd, 1H, J=4.8, 14.4 Hz), 1.56-1.63 (m, 2H), 1.21 (s, 3H), 1.20 (s, 3H), 0.83 (t, 3H, J=7.6 Hz). LC-MS (ESI) [M+H]$^+$ calcd for C$_{23}$H$_{30}$N$_2$O$_3$, 383.2. found, 383.4.

Compound 127: Preparation of (R)-2,2-dimethyl-N-(2-oxo-2-((2-phenoxyethyl)amino)-1-phenylethyl)butanamide

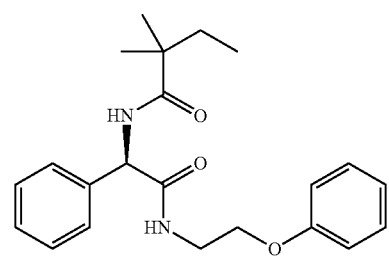 [SMILES: CCC(C)(C)C(=O)N[C@@H](C(=O)NCCOc1ccccc1)c1ccccc1]

The titled compound 127 was prepared in 40% yield from (R)-2-(2,2-dimethylbutanamido)-2-phenylacetic acid (30 mg) and 2-phenoxyethanamine (20 mg) according to the procedure outlined for compound 65. $^1$HNMR (CDCl$_3$, 400 MHz): δ 7.27-7.36 (m, 5H), 7.23-7.25 (m, 1H), 6.92-7.00 (m, 2H), 6.77-6.80 (m, 2H), 6.10 (brs, 1H), 5.41 (d, 1H, J=6.4 Hz), 3.94-4.03 (m, 2H), 3.57-3.71 (m, 2H), 1.51-1.57 (m, 2H), 1.17 (s, 3H), 1.16 (s, 3H), 0.77 (t, 3H, J=7.6 Hz). LC-MS (ESI) [M+H]$^+$ calcd for C$_{22}$H$_{28}$N$_2$O$_3$, 369.2. found, 369.4.

Compound 128: Preparation of N-((4,5-dimethylthiophen-2-yl)methyl)-N,2,2-trimethylbutanamide

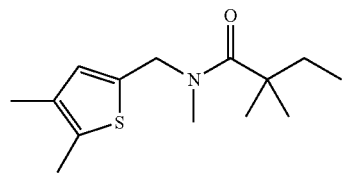 [SMILES: CCC(C)(C)C(=O)N(C)Cc1cc(C)c(C)s1]

The titled compound 128 was prepared in 36% yield from 1-(4,5-dimethylthiophen-2-yl)-N-methylmethanamine (60 mg), which was prepared from 4,5-dimethylthiophene-2-carbaldehyde and methanamine hydrochloride according to the procedure outlined for compound 13, and 2,2-dimethylbutanoyl chloride (57 mg) according to the procedure outlined for compound 52. $^1$H NMR: (CDCl$_3$, 400 M Hz): δ6.61 (s, 1H), 4.58 (s, 2H), 3.03 (s, 3H), 2.28 (s, 3H), 2.07 (s, 3H), 1.66 (q, 2H, J=7.6 Hz), 1.27 (s, 6H), 0.88 (t, 3H, J=7.6 Hz). LC-MS (ESI) [M+H]$^+$ calcd for C$_{14}$H$_{23}$NOS 254.2. found 254.3.

Compound 129: Preparation of 2,6-dichloro-N-methyl-N-(3,4,5-trifluorobenzyl)benzamide

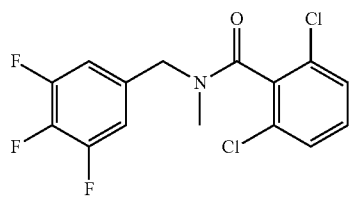 [SMILES: CN(Cc1cc(F)c(F)c(F)c1)C(=O)c1c(Cl)cccc1Cl]

The titled compound 129 was prepared in 77% yield from N-methyl-1-(3,4,5-trifluorophenyl)methanamine (30 mg) and 2,6-dichlorobenzoyl chloride (39.5 mg) according to the procedure outlined for compound 52. $^1$H NMR: (CDCl$_3$, 400 M Hz): δ7.33-7.36 (m, 2H), 7.26-7.29 (m, 1H), 7.04-7.07 (m, 2H), 4.72 (s, 2H), 2.77 (s, 3H). LC-MS (ESI) [M+H]$^+$ calcd for C$_{15}$H$_{10}$C$_{12}$F$_3$NO, 348.0. found, 348.2.

Compound 130-135 and 151

Compound 130-135 are prepared according to the method of scheme 1

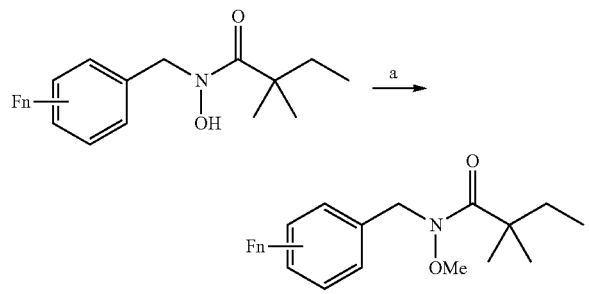

Scheme 1: Reagent and conditions: (a): NaOH, Dimethylsulfate, DCM/H$_2$O

Compound 136-147

Compounds 136-147 are prepared according to the method of scheme 2

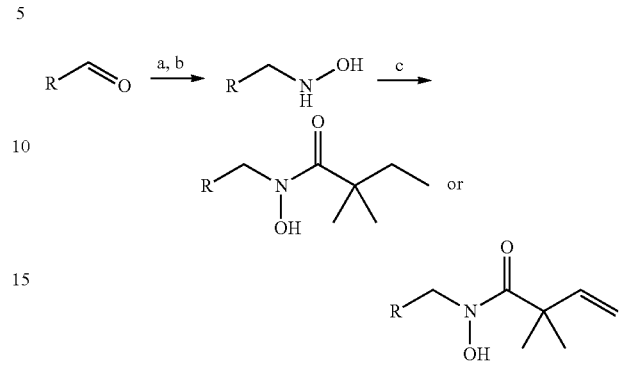

Scheme 2: Reagent and conditions: (a): NH$_2$OH*HCl; Na$_2$CO$_3$; (b): Na(CN)BH$_3$; (c) 2,2-dimethylbutanoyl chloride or 2,2-dimethylbut-3-enoyl chloride, NaHCO3, THF/H2O, 0° C. 30 min, rt, 16 h.

Compound 148 and 149

Compound 148 and 149 are prepared according to the method of scheme 3

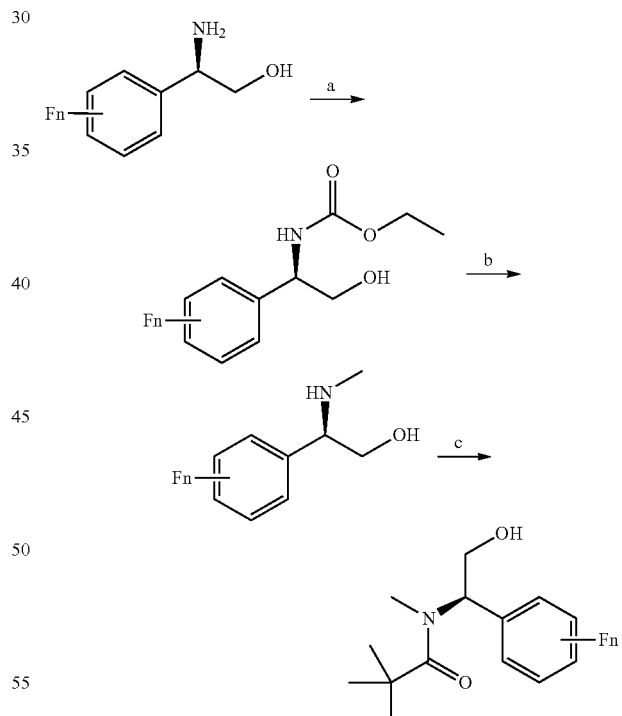

Scheme 3: Reagent and conditions: (a): NaHCO3, ethyl carbonochloridate, THF/DCM (b) LiAlH$_4$, THF, rt, 16 h (c): 2,2-dimethylbutanoyl chloride NaHCO3, THF/H2O, 0° C. 30 min, rt, 16 h.

Compound 150

Compound 150 is prepared according to the method of scheme 4

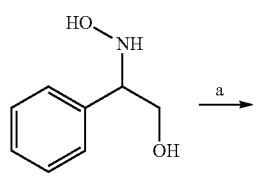

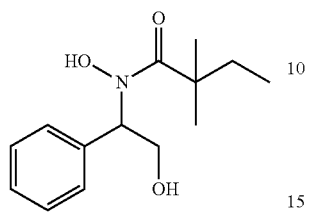

Scheme 4: Reagent and conditions: (a): NaHCO3, ethyl carbonochloridate, THF/DCM, 0° C. 30 min, rt, 16 h.

Compound S1: Preparation of N-(2,3,5-trifluorobenzyl)pivalamide

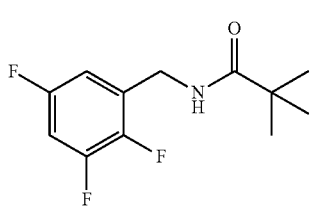

(2,3,5-trifluorophenyl)methanamine (42 mg, 0.263 mmol) and triethylamine (53.2 mg, 0.526 mmol) were dissolved in 2 mL of dry CH$_2$Cl$_2$. Pivaloyl chloride (38 mg, 0.316 mmol) was added slowly to the solution at 0° C. under nitrogen. The mixture was stirred at room temperature for 2 h, diluted with CH$_2$Cl$_2$ and water. The organic layer were washed with saturated NaHCO$_3$ solution, brine, dried with Na$_2$SO$_4$ and concentrated. The residue was purified by chromatography to give compound 51 (49 mg, 74%) as an light yellow oil. $^1$H NMR (400 MHz, CDCl$_3$) δ 6.86-6.77 (m, 2H), 4.47 (d, J=4.9 Hz, 2H), 1.21 (s, 9H). LC-MS (ESI) [M+H]$^+$ calcd for C$_{12}$H$_{15}$F$_3$NO, 246.11. found, 246.17.

Compound S2: Preparation of N-methyl-N-(2,3,5-trifluorobenzyl)pivalamide

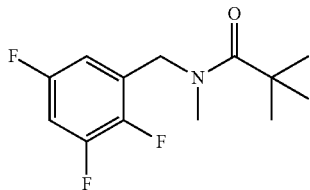

Compound S1 (70 mg) was dissolved in 2 mL of dry THF, 17 mg of NaH (60%) was added at 0° C. under N$_2$ and stirred for 2 h. Iodomethane (0.026 mL) was added and the mixture was allowed to warm to room temperature and stirred for 12 h. The mixture was quenched with cold water and extracted with DCM, the combined organic layers was washed with water, brine, dried over Na$_2$SO$_4$, concentrated and the residue was purified by pre-TLC to give the product S2 (35 mg, 47%). $^1$H NMR (400 MHz, CDCl$_3$) δ 6.82-6.71 (m, 2H), 4.65 (s, 2H), 3.11 (s, 3H), 1.33 (s, 9H). LC-MS (ESI) [M+H]$^+$ calcd for C$_{13}$H$_{17}$F$_3$NO, 260.13. found, 260.19.

Compound 3: Preparation of N-acetoxy-N-benzyl-2,2-dimethylbutanamide

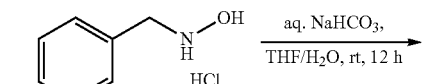

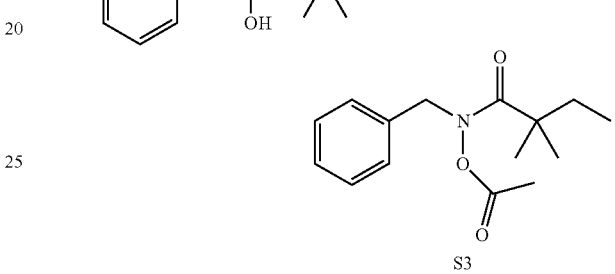

n-benzylhydroxylamine hydrochloride (100 mg) was dissolved in 2 mL of THF/H$_2$O (1:1) and 0.45 mL of saturated aqueous NaHCO$_3$. The solution was cooled to 0° C. and 2,2-dimethylbutanoylchloride (81 mg) was added and the mixture was stirred at rt for 16 h. The mixture was extracted with EtOAc and the combined organic layer washed with brine, dried (Na$_2$SO4) and concentrated in vacuo. Purification by silica gel chromatography to give N-benzyl-N-hydroxy-2,2-dimethylbutanamide (60 mg, 43.3%) as an white solid. $^1$H NMR (400 MHz, CDCl$_3$) δ 7.37-7.34 (m, 2H), 7.33-7.31 (m, 3H), 4.89 (s, 2H), 1.69 (q, J=7.6 Hz, 2H), 1.26 (s, 6H), 0.86 (t, J=7.6 Hz, 6H).

N-benzyl-N-hydroxy-2,2-dimethylbutanamide (800 mg) and TEA (2.5 mL) were dissolved in 20 mL of DCM. Acetyl chloride (0.283 mL) was added slowly to the mixture at 0° C. and the mixture was stirred at room temperature for 16 h, concentrated and the residue was purified by chromatography to give product S3 (260 mg, 27.3%). $^1$H NMR (400 MHz, CDCl$_3$) δ 7.33-7.23 (m, 5H), 4.89 (s, 2H), 2.09 (s, 3H), 1.53 (q, J=7.5 Hz, 2H), 1.16 (s, 6H), 0.80 (t, J=7.5 Hz, 3H).

Compound S4: Preparation of N-benzyl-N-methoxy-2,2-dimethylbutanamide

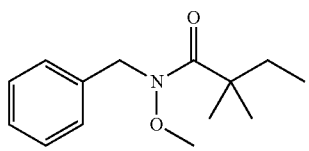 [SMILES: CCC(C)(C)C(=O)N(Cc1ccccc1)OC]

N-benzyl-N-hydroxy-2,2-dimethylbutanamide (800 mg), iodomethane (565.2 mg) and KOH (179.4 mg) were added in 30 mL of ethanol. The mixture was stirred at 50° C. for 5 h and evaporated to dryness. The residue was diluted with CH$_2$Cl$_2$ and water. The organic layer were washed with brine, dried with Na$_2$SO$_4$ and concentrated. The residue was purified by chromatography to give compound S4 (210 mg, 28.2%). $^1$H NMR (400 MHz, CDCl$_3$) δ 7.34-7.22 (m, 5H), 4.79 (s, 2H), 3.64 (s, 3H), 1.63 (q, J=7.5 Hz, 2H), 1.20 (s, 6H), 0.79 (t, J=7.5 Hz, 3H).

Compound S5: Preparation of 3,3-difluoro-N,2,2-trimethyl-N-(2,3,5-trifluorobenzyl)butanamide

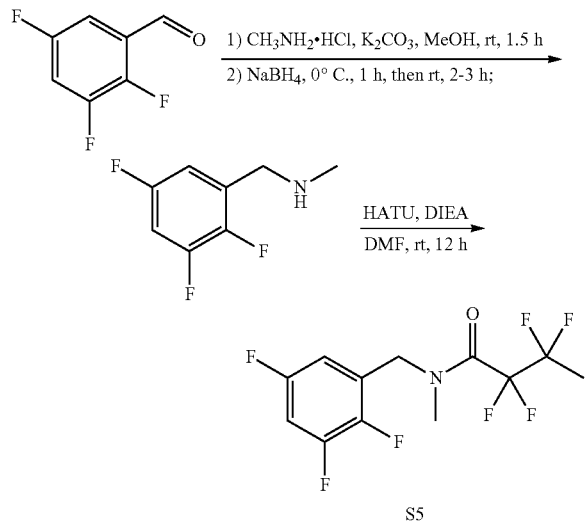

A mixture of K$_2$CO$_3$ (324 mg, 2.35 mmol) and methanamine hydrochloride (316 mg, 4.69 mmol) in 10 mL of MeOH was stirred at rt for 30 min. Then 2,3,5-trifluorobenzaldehyde (500 mg, 3.125 mmol) was added to the mixture and stirred at rt for 2 h. The mixture was cooled to 0° C., and NaBH$_4$ (178.2 mg, 4.69 mmol) was added in portions. The mixture was stirred at 0° C. for 1 h and warmed to room temperature and stirred for 12 h. The solid was filtered and washed with EtOAc. The filtrate was evaporated to dryness and the residue was dissolved in EtOAc and the organic layer was washed with water, brine, dried over Na$_2$SO$_4$, concentrated to give N-methyl-1-(2,3,5-trifluorophenyl)methanamine (260 mg), which used for next step without further purification. $^1$H NMR (400 MHz, CDCl$_3$) δ 6.94-6.87 (m, 1H), 6.86-6.76 (m, 1H), 3.81 (d, J=1.4 Hz, 2H), 2.44 (s, 3H).

To a solution of N-methyl-1-(2,3,5-trifluorophenyl)methanamine (44 mg) and 3,3-difluoro-2,2-dimethylbutanoic acid (38 mg) in dry DMF (1 mL) was added 2-(7-Aza-1H-benzotriazole-1-yl)-1,1,3,3-tetramethyluronium hexafluorophosphate (142 mg) and DIEA (0.08 mL). The mixture was stirred at room temperature for 12 h and concentrated in vacuo. The residue was diluted with CH$_2$Cl$_2$ and water. The aqueous layer was extracted with CH$_2$Cl$_2$. The combined organic layer was washed with saturated brine, dried with Na$_2$SO$_4$ and concentrated. The residue was purified by pre-TLC to give compound S5 (36 mg, 46%). $^1$H NMR (400 MHz, CDCl$_3$) δ 6.88-6.78 (m, 1H), 6.71 (m, 1H), 4.67 (s, 2H), 3.15 (s, 3H), 1.66 (t, J=19.4 Hz, 3H), 1.46 (s, 6H). LC-MS (ESI) [M+H]$^+$ calcd for C$_{14}$H$_{17}$F$_5$NO, 310.12. found, 310.21.

Compound S6: Preparation of N-benzyl-3,3-difluoro-N-hydroxy-2,2-dimethylbutanamide

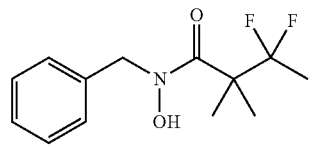 [SMILES: CC(F)(F)C(C)(C)C(=O)N(O)Cc1ccccc1]

To a solution of n-benzylhydroxylamine hydrochloride (36.8 mg) and 3,3-difluoro-2,2-dimethylbutanoic acid (35 mg) in dry DMF (1 mL) was added 1-Ethyl-3-(3-dimethylaminopropyl)carbodiimide hydrochloride (66 mg) and DIEA (0.16 mL). The mixture was stirred at room temperature for 12 h and concentrated in vacuo. The residue was diluted with CH$_2$Cl$_2$ and water. The aqueous layer was extracted with CH$_2$Cl$_2$. The organic layer were washed with saturated brine, dried with Na$_2$SO$_4$ and concentrated. The residue was purified by pre-TLC to give compound S6 (10 mg, 17%). $^1$H NMR (400 MHz, CDCl$_3$) δ 7.34-7.25 (m, 5H), 4.64 (s, 2H), 1.73 (t, J=19.8 Hz, 3H), 1.38 (s, 6H).

Compound S7: Preparation of N-(4-fluorobenzyl)-N,2,2-trimethylbutanamide

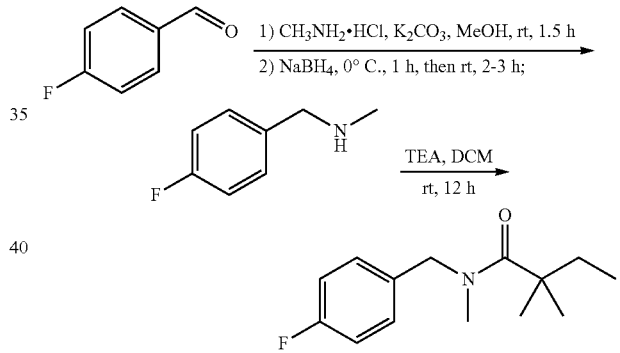

A mixture of K$_2$CO$_3$ (207 mg, 1.5 mmol) and methanamine hydrochloride (202 mg, 3.0 mmol) in 5 mL of MeOH was stirred at rt for 30 min. Then 4-fluorobenzaldehyde (248 mg, 2.0 mmol) was added to the mixture and stirred at rt for 1 h. The mixture was cooled to 0° C., and NaBH$_4$ (113.5 mg, 3.0 mmol) was added in portions. The mixture was stirred at 0° C. for 1 h and warmed to room temperature and stirred for 2 h. The solid was filtered and washed with EtOAc. The filtrate was evaporated to dryness and the residue was dissolved in EtOAc and the organic layer was washed with water, brine, dried over Na$_2$SO$_4$. The residue was dissolved in 10 mL of dry THF. DIEA (264 mg, 2.05 mmol) was added, 2,2-dimethylbutanoyl chloride (275 mg, 2.05 mmol) was added slowly to the solution at 0° C. under nitrogen, then stirred at room temperature for 2 h. 15 mL of water was added to the solution and extracted with EtOAc (10 mL×3). The combined organic was washed with 1M HCl, brine, dried with Na$_2$SO$_4$ and concentrated in vacuo. The residue was purified by silica gel column chromatography (PE/EA=1/2) to give the 189 mg of S7 as a brown solid (total yield=40%). $^1$H NMR (400 M Hz, CDCl$_3$) δ 7.21-7.12 (m, 2H), 6.98-6.93 (m, 2H), 4.54 (s, 2H), 2.95 (s, 3H), 1.64 (q, J=7.5 Hz, 2H), 1.24 (s, 6H), 0.84 (t, J=7.5 Hz, 3H). LC-MS (ESI) [M+H]+ calcd for: $C_{14}H_{21}F_2NO$, 256.16. found, 256.18.

Compound S8: Preparation of N-(2,3-difluorobenzyl)-N,2,2-trimethylbutanamide

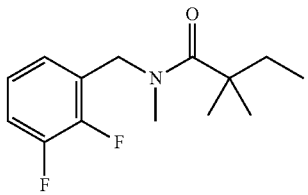 [SMILES: CCC(C)(C)C(=O)N(C)Cc1cccc(F)c1F]

Compound S8 was prepared in 56% yield from 2,3-difluorobenzaldehyde (284 mg), methanamine hydrochloride (202 mg) and 2,2-dimethylbutanoyl chloride (275 mg) according to the procedure outlined for compound 7. $^1$H NMR (400 M Hz, CDCl$_3$) δ 7.11-6.94 (m, 3H), 4.66 (s, 2H), 3.06 (s, 3H), 1.66 (q, J=7.5 Hz, 2H), 1.25 (s, 6H), 0.85 (t, J=7.5 Hz, 3H). LC-MS (ESI) [M+H]+ calcd for: $C_{14}H_{20}F_2NO$, 256.15. found, 256.18.

Compound S9-S20

Compound S9-S20 are prepared according to the procedure outlined in scheme 1

Scheme 1:

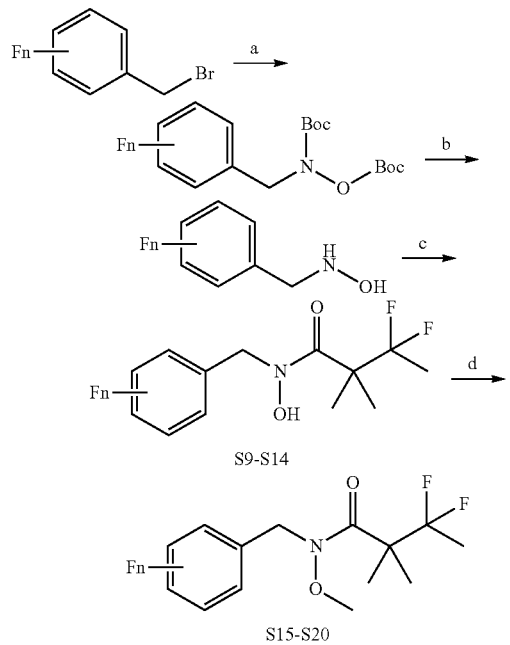

Reagent and conditions; (a) tert-butyl)tert-butoxycarbonyl) oxycarbamate, 1N NaOH, TBAB, DCM; (b) TFA, DCM; (c) 3,3-difluoro-2,2-dimethylbutanoic acid, EDCl, DIEA, DMF, rt, 12 h (d) NaH, MeI, THF.

9,15: 4-F
10,16: 2F,4-F
11,17: 3-F,4-F
12,18: 2-F,4-F,5-F
13,19: 3-F,4-F,5-F
14,20: 2-F,3-F,5-F

3. Kinase Assay of RIPK1

Materials: Recombinant full-length RIPK1 protein with N-terminal GST-tag (Cat#R07-34G) was purchased from SignalChem. The ADP-Glo™ kinase assay kit (Cat#V9102) was from Promega. MBP (cat# M2295) protein and all the other chemicals were from Sigma. The 384-well assay plates (Cat#3674, white, opaque) were purchased from Corning.

Kinase activity assay and data analysis: The RIPK1 kinase assay was performed in white 384-well plate. The assay buffer contained 25 mM HEPES (pH7.2), 20 mM MgCl2, 12.5 mM MnCl2, 5 mM EGTA, 2 mM EDTA, 12.5 mM β-glycerol phosphate and 2 mM DTT. RIPK1 was first incubated with compounds or DMSO control for 15 min, then ATP/MBP substrate mixture was added to initiate the reaction. The final concentration of RIPK1 was 161 nM, while the final concentration of ATP was 50 uM, and MBP 20 uM. After 90 min reaction at room temperature, the ADP-Glo reagent and detection solution were added following the technical manual of ADP-Glo™ kinase assay kit (Promega). The luminescence was measured on PerkinElmer Enspire. The data was analyzed using Graphpad Prism (GraphPad Software; www.graphpad.com). The curves were fitted using a non-linear regression model with a sigmoidal dose response.

Results: pIC50 of hRIP1 kinase assay correlated with our pIC50 of cell necrosis assay. Exemplary data are shown below:

| # | RIP1 CMPD ID | Cell viability assay, EC50 (nM) | hRIP1 kinase assay, IC50(nM) or % inhibition at 2 uM |
|---|---|---|---|
| 14 | TC001004 | 3277 | 66% inhibition at 2 uM |
| 16 | TC001014 | 150.9/70.59 | IC50 = 52 nM |
| 75 | TC001035 | 0.247/10.21 | IC50 = 33 nM |
| 92 | TC001165 | 28.36 | IC50 = 13.2 nM |
| 99 | TC001186 | 45.7 | IC50 = 29.6 nM |

4. Necrosis Assay

Methods:

HT-29 cells were cultured in McCoy's 5 A culture medium (Invitrogen). On day one, HT-29 cells were plated in 96-well assay plates at density of 2,500-3,500 cells per well. On day two, necrosis were induced by adding 20 ng/ml TNF-α (T), 100 nM Smac mimetic (S), and 20 mM z-VAD (Z). At the same time, 10 mM compound from a chemical library of ~200,000 compounds was delivered into each well. After 24 hrs treatment, cell viability was determined by measuring ATP level using the CellTiter-Glo Luminescent Cell Viability Assay kit. A CellTiter-Glo Assay (Promega) was performed according to the manufacturer's instructions Luminescence was recorded with a PerkinElmer EnSpire Multimode Plate Reader. Survived cells were normalized to those cells treated with DMSO. Nec-1 was used as a positive control for screening necrosis inhibitors. Data are represented as mean±standard deviation of duplicates Dose-dependent inhibition of necrosis by the compounds in HT-29 cells were determined by measuring ATP levels as described above. Compound necrosis activity data are reported below:

| # | EC50 | # | EC50 | # | EC50 |
|---|---|---|---|---|---|
| 1 | 1-10 uM | 52 | 1-100 uM | 103 | 1-100 uM |
| 2 | 1-10 uM | 53 | 1-100 uM | 104 | 1-100 uM |
| 3 | 1-10 uM | 54 | 1-100 uM | 105 | 1-100 uM |
| 4 | 1-10 uM | 55 | 1-100 uM | 106 | 1-100 uM |

-continued

| # | EC50 | # | EC50 | # | EC50 |
|---|---|---|---|---|---|
| 5 | 1-10 uM | 56 | 1-10 uM | 107 | 1-100 uM |
| 6 | 1-10 uM | 57 | 1-10 uM | 108 | 1-100 uM |
| 7 | 1-10 uM | 58 | 1-1000 nM | 109 | 1-100 uM |
| 8 | 1-10 uM | 59 | 1-10 uM | 110 | 1-100 uM |
| 9 | 1-10 uM | 60 | 1-10 uM | 111 | 1-100 uM |
| 10 | 1-10 uM | 61 | 1-100 uM | 112 | 1-100 uM |
| 11 | 1-10 uM | 62 | 1-100 uM | 113 | 1-100 uM |
| 12 | 1-10 uM | 63 | 1-100 uM | 114 | 1-100 uM |
| 13 | 1-1000 nM | 64 | 1-100 uM | 115 | 1-100 uM |
| 14 | 1-10 uM | 65 | 1-1000 nM | 116 | 1-100 uM |
| 15 | 1-100 uM | 66 | 1-100 uM | 117 | 1-10 uM |
| 16 | 1-1000 nM | 67 | 1-10 uM | 118 | 1-100 uM |
| 17 | 1-1000 nM | 68 | 1-100 uM | 119 | 1-100 uM |
| 18 | 1-1000 nM | 69 | 1-10 uM | 120 | 1-10 uM |
| 19 | 1-10 uM | 70 | 1-1000 nM | 121 | 1-1000 nM |
| 20 | 1-100 uM | 71 | 1-100 uM | 122 | 1-100 uM |
| 21 | 1-100 uM | 72 | 1-10 uM | 123 | 1-100 uM |
| 22 | 1-100 uM | 73 | 1-10 uM | 124 | 1-100 uM |
| 23 | 1-100 uM | 74 | 1-100 uM | 125 | 1-100 uM |
| 24 | 1-1000 nM | 75 | 1-1000 nM | 126 | 1-100 uM |
| 25 | 1-1000 nM | 76 | 1-100 uM | 127 | 1-100 uM |
| 26 | 1-1000 nM | 77 | 1-1000 nM | 128 | 1-1000 nM |
| 27 | 1-1000 nM | 78 | 1-100 uM | 129 | 1-100 uM |
| 28 | 1-1000 nM | 79 | 1-100 uM | 130 | 1-100 uM |
| 29 | 1-10 uM | 80 | 1-100 uM | 131 | 1-100 uM |
| 30 | 1-100 uM | 81 | 1-100 uM | 132 | 1-100 uM |
| 31 | 1-100 uM | 82 | 1-100 uM | 133 | 1-100 uM |
| 32 | 1-100 uM | 83 | 1-10 uM | 134 | 1-100 uM |
| 33 | 1-100 uM | 84 | 1-1000 nM | 135 | 1-100 uM |
| 34 | 1-100 uM | 85 | 1-100 uM | 136 | 1-100 uM |
| 35 | 1-10 uM | 86 | 1-100 uM | 137 | 1-100 uM |
| 36 | 1-100 uM | 87 | 1-100 uM | 138 | 1-100 uM |
| 37 | 1-100 uM | 88 | 1-100 uM | 139 | 1-100 uM |
| 38 | 1-100 uM | 89 | 1-10 uM | 140 | 1-100 uM |
| 39 | 1-1000 nM | 90 | 1-1000 nM | 141 | 1-100 uM |
| 40 | 1-1000 nM | 91 | 1-1000 nM | 142 | 1-100 uM |
| 41 | 1-10 uM | 92 | 1-1000 nM | 143 | 1-100 uM |
| 42 | 1-1000 nM | 93 | 1-1000 nM | 144 | 1-100 uM |
| 43 | 1-1000 nM | 94 | 1-1000 nM | 145 | 1-100 uM |
| 44 | 1-10 uM | 95 | 1-1000 nM | 146 | 1-100 uM |
| 45 | 1-100 uM | 96 | 1-1000 nM | 147 | 1-100 uM |
| 46 | 1-100 uM | 97 | 1-1000 nM | 148 | 1-100 uM |
| 47 | 1-100 uM | 98 | 1-1000 nM | 149 | 1-100 uM |
| 48 | 1-10 uM | 99 | 1-1000 nM | 150 | 1-100 uM |
| 49 | 1-1000 nM | 100 | 1-100 uM | 151 | 1-100 uM |
| 50 | 1-10 uM | 101 | 1-100 uM | S1 | 1-10 uM |
| 51 | 1-10 uM | 102 | 1-100 uM | S2 | 1-1000 nM |
| S3 | 1-1000 nM | S4 | 1-1000 nM | S5 | 1-1000 nM |
| S6 | 1-1000 nM | S7 | 1-10 uM | S8 | 1-1000 nM |
| S9 | 1-100 uM | S10 | 1-100 uM | S11 | 1-100 uM |
| S12 | 1-100 uM | S13 | 1-100 uM | S14 | 1-100 uM |
| S15 | 1-100 uM | S16 | 1-100 uM | S17 | 1-100 uM |
| S18 | 1-100 uM | S19 | 1-100 uM | S20 | 1-100 uM |

What is claimed is:

1. A method of inhibiting necrosis, comprising contacting cells determined to be in need thereof with an amide compound that is an inhibitor of cellular necrosis, of formula:

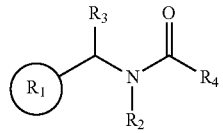

I wherein:
$R_1$ is substituted or unsubstituted phenyl;
$R_2$ is hydroxyl;
$R_3$ is H; and
$R_4$ is 1,1-dimethylpropyl, optionally fluorinated; or a pharmaceutically acceptable salt, hydrate or stereoisomer thereof.

2. The method of claim 1, wherein:
$R_1$ is phenyl.

3. The method of claim 1, wherein:
$R_1$ is fluoro-substituted phenyl.

4. The method of claim 1, wherein:
$R_4$ is 1,1-dimethylpropyl.

5. The method of claim 2, wherein:
$R_4$ is 1,1-dimethylpropyl.

6. The method of claim 3, wherein:
$R_4$ is 1,1-dimethylpropyl.

7. The method of claim 1, wherein:
$R_4$ is fluorinated 1,1-dimethylpropyl.

8. The method of claim 2, wherein:
$R_4$ is fluorinated 1,1-dimethylpropyl.

9. The method of claim 3, wherein:
$R_4$ is fluorinated 1,1-dimethylpropyl.

10. The method of claim 1, wherein:
$R_4$ is 1-dimethyl, 2-difluoropropyl.

11. The method of claim 2, wherein:
$R_4$ is 1-dimethyl, 2-difluoropropyl.

12. The method of claim 3, wherein:
$R_4$ is 1-dimethyl, 2-difluoropropyl.

13. The method of claim 1 wherein the compound has a formula of Table 1:

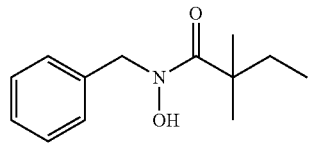

92

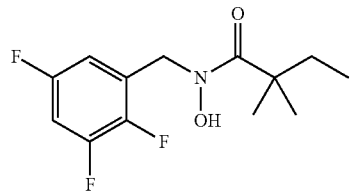

93

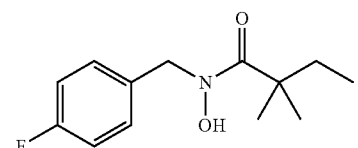

94

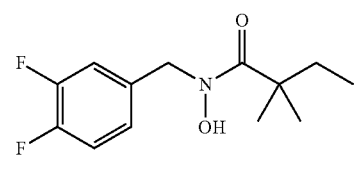

95

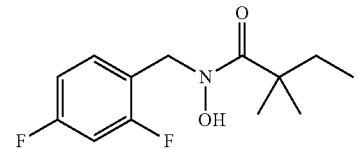

96

-continued

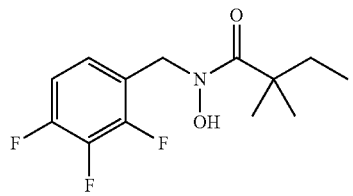
97

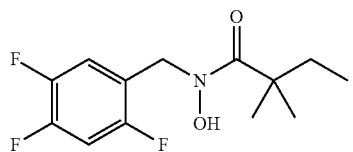
98

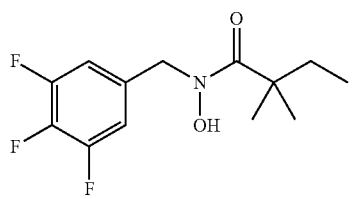
99

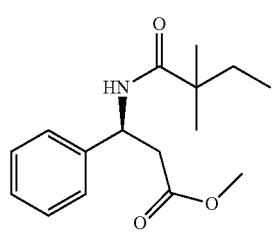
100

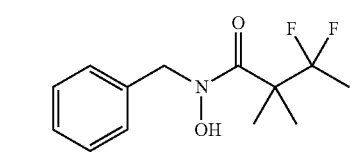
S6

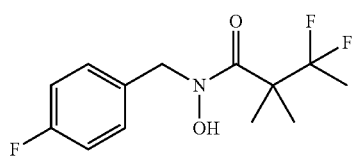
S9

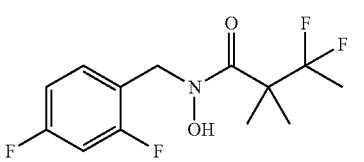
S10

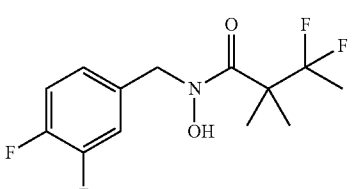
S11

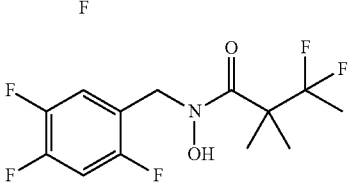
S12

-continued

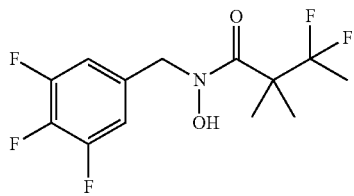
S13

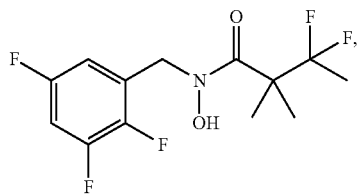
S14 or a pharmaceutically acceptable salt, hydrate or stereoisomer thereof.

14. The method of claim 1 wherein the compound has a formula:

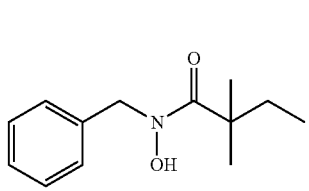
92 or a pharmaceutically acceptable salt, hydrate or stereoisomer thereof.

15. The method of claim 1 wherein the compound has a formula

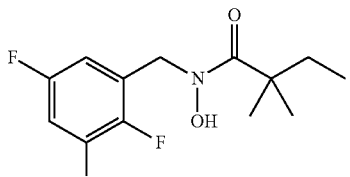
93 or a pharmaceutically acceptable salt, hydrate or stereoisomer thereof.

16. The method of claim 1 wherein the compound has a formula:

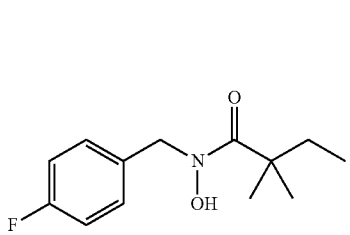
94 or a pharmaceutically acceptable salt, hydrate or stereoisomer thereof.

17. The method of claim 1 wherein the compound has a formula

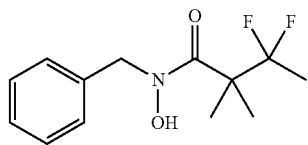

S6 or a pharmaceutically acceptable salt, hydrate or stereoisomer thereof.

18. The method of claim 1 wherein the compound has a formula:

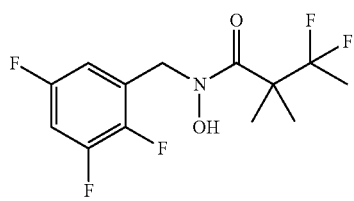

S14 or a pharmaceutically acceptable salt, hydrate or stereoisomer thereof.

19. The method of claim 1 wherein the compound has a formula

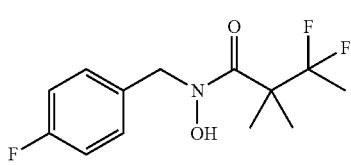

S9 or a pharmaceutically acceptable salt, hydrate or stereoisomer thereof.

20. The method of claim 1 wherein the compound has a formula

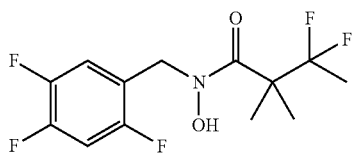

S12 or a pharmaceutically acceptable salt, hydrate or stereoisomer thereof.

* * * * *